(12) United States Patent
Chan Chun Kong et al.

(10) Patent No.: US 7,288,548 B2
(45) Date of Patent: Oct. 30, 2007

(54) SPIRO COMPOUNDS AND METHODS FOR THE MODULATION OF CHEMOKINE RECEPTOR ACTIVITY

(75) Inventors: Laval Chan Chun Kong, Kirkland (CA); Ming-Qiang Zhang, Cherry Hinton (GB); Christophe Moinet, Montreal (CA); Marc Courchesne, Laval (CA); Thumkunta Jagadeeswar Reddy, Pierrefonds (CA)

(73) Assignee: ViroChem Pharma, Inc., Laval, Quebec (CA)

( * ) Notice: Subject to any disclaimer, the term of this patent is extended or adjusted under 35 U.S.C. 154(b) by 284 days.

(21) Appl. No.: 10/937,880

(22) Filed: Sep. 10, 2004

(65) Prior Publication Data

US 2005/0070563 A1    Mar. 31, 2005

Related U.S. Application Data

(60) Provisional application No. 60/501,407, filed on Sep. 10, 2003.

(51) Int. Cl.
*A61K 31/438* (2006.01)
*C07D 471/10* (2006.01)

(52) U.S. Cl. .................. 514/278; 546/16; 544/124; 544/242; 514/232.8; 514/256

(58) Field of Classification Search ........... 514/278, 514/232.8, 256; 546/16; 544/124, 242
See application file for complete search history.

(56) References Cited

U.S. PATENT DOCUMENTS

2003/0166928 A1    9/2003   Schlienger

FOREIGN PATENT DOCUMENTS

| GB | 2 142 332 | 1/1995 |
|---|---|---|
| WO | WO9909984 | 3/1999 |
| WO | WO 0207790 | 5/2000 |
| WO | WO 0051607 | 9/2000 |
| WO | WO 0051608 | 9/2000 |
| WO | WO 0051609 | 9/2000 |
| WO | WO 0051610 | 9/2000 |
| WO | WO 0059502 | 10/2000 |
| WO | WO 01/30780 | 5/2001 |
| WO | WO 0234716 | 5/2002 |
| WO | WO 03-057698 | 7/2003 |
| WO | WO 2004058702 | 7/2004 |
| WO | WO 2004058763 | 7/2004 |

OTHER PUBLICATIONS

P.W. Smith et al. *J. Med. Chem.* 1995, 38, 3772-3779.
M.J. McKennon et al. *J.Org. Chem.* 1993, 58, 3568-3571.
P.A. Reddy et al. *J. Med. Chem.* 1996, 39, 1898-1906.
M.M. Mehrotra et al. *Bioorg. Med. Chem. Lett.* 2002, 12, 1103-1107.
Z. Ma et al. *Tet. Asymm.* 1997, 8, 883-887.
S. Karlsson et al. *Tet. Asymm.* 1999, 10, 2605-2616.
J.J. Hale et al. *Bioorg. Med. Chem. Lett.* 2001, 11, 1437-1440.
J.J. Hale et al. *Bioorg. Med. Chem. Lett.* 2001, 11, 2741-2745.
J.J. Hale et al. *Bioorg. Med. Chem. Lett.* 2002, 12, 2997-3000.
C.A. Willoughby et al. *Bioorg. Med. Chem. Lett.* 2003, 13, 427-431.
Int'l Search Report and the Written Opinion of the Int'l. Searching Authority, issued in PCT Application No. PCT/CA2004/001656 dated Jan. 31, 2005.

*Primary Examiner*—Charanjit S. Aulakh
(74) *Attorney, Agent, or Firm*—Millen, White, Zelano & Branigan, P.C.

(57) ABSTRACT

Compounds of formula I

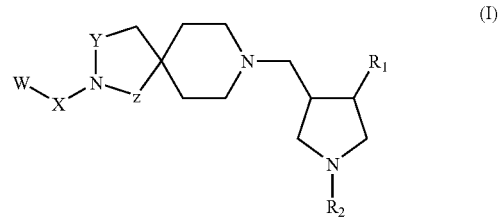

wherein X, Y, Z, W, $R_1$ and $R_2$ as defined herein, or pharmaceutically acceptable salts, hydrates or solvates thereof, are useful for the modulation of CCR5 chemokine receptor activity.

40 Claims, No Drawings

SPIRO COMPOUNDS AND METHODS FOR THE MODULATION OF CHEMOKINE RECEPTOR ACTIVITY

This application claims benefit of U.S. Provisional Application Ser. No. 60/501,407, filed Sep. 10, 2003, the entire disclosure of which is hereby incorporated by reference.

FIELD OF THE INVENTION

The present invention relates to novel spiro compounds and a method of modulating chemokine receptor activity using these compounds. The present invention is also directed to novel spiro compounds which are useful in the prevention or treatment of diseases associated with the modulation of CCR5 chemokine receptor activity. The present invention is further directed to a method of blocking cellular entry of HIV in a subject and to compositions using these compounds.

BACKGROUND OF THE INVENTION

Chemokines are chemotactic cytokines that are released by a wide variety of cells to attract macrophages, T cells, eosinophils, basophils and neutrophils to sites of inflammation and they also play a role in the maturation of cells of the immune system. Chemokines play an important role in immune and inflammatory responses in various diseases and disorders, including asthma, rhinitis and allergic diseases, as well as autoimmune pathologies such as rheumatoid arthritis and atherosclerosis. Chemokines are small 70 to 80 amino acid proteins with well-characterized three-dimensional structures, usually stabilized by two disulfide bridges. They are divided into four families on the basis of pattern of conserved cysteine residues. Chemokine receptors have been designated such as, CCR1, CCR2, CCR2A, CCR2B, CCR3, CCR4, CCR5, CCR6, CCR7, CCR8, CCR9, CCR10, CXCR1, CXCR2, CXCR3, and CXCR4 and therefore agents which modulate these receptors may be useful in the prevention and treatment of diseases as mentioned above.

One of them, the C-C chemokines family, includes potent chemoattractants of monocytes and lymphocytes such as RANTES (Regulated on Activation, Normal T Expressed and Secreted), eotaxin, MIP-1α and MIP-1β (Macrophage Inflammatory Proteins) and human monocyte chemotactic proteins 1-3 (MCP-1, MCP-2 and MCP-3). More specifically, C-C chemokine receptor 5 (CCR5), a β-chemokine receptor with a seven-transmembrane-protein structure, was found to serve as a coreceptor for non-syncytium-inducing or macrophage-tropic HIV-1 (R5 viruses). It was also established that CCR5 is the principal chemokine receptor required for the entry of HIV into the cell during primary infection. Therefore, interfering with the interaction between the viral receptor CCR5 and HIV can block HIV entry into the cell. It would therefore be useful to provide novel compounds which are modulators of chemokine receptor activity.

SUMMARY OF THE INVENTION

In one aspect, the present invention provides novel compounds represented by formula (I):

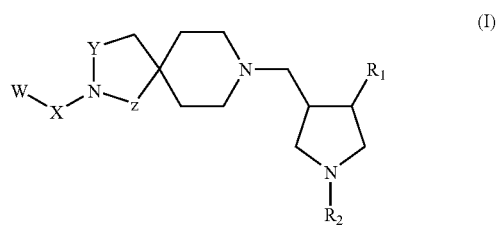

or pharmaceutically acceptable salts, hydrates or solvates thereof, wherein X, Y and Z are each independently chosen from $CH_2$, $C=O$ or $CR_3R_4$;

W is chosen from H, optionally substituted $C_{1-10}$ alkyl (e.g. $C_{1-6}$ alkyl), optionally substituted $C_{2-10}$ alkenyl (e.g. $C_{2-6}$ alkenyl), optionally substituted $C_{2-10}$ alkynyl (e.g. $C_{2-6}$ alkynyl), optionally substituted $C_{6-12}$ aryl, optionally substituted 3 to 10 membered heterocycle, optionally substituted $C_{6-12}$ aralkyl (e.g. $C_{7-12}$ aralkyl) or optionally substituted 3 to 10 membered heteroaralkyl (e.g. heteroaralkyl having a 3 to 9 membered heterocyclic group and a $C_{1-6}$ alkylene group);

$R_1$ is chosen from H, optionally substituted $C_{1-10}$ alkyl (e.g. $C_{1-6}$ alkyl), optionally substituted $C_{2-10}$ alkenyl (e.g. $C_{2-6}$ alkenyl), optionally substituted $C_{2-10}$ alkynyl (e.g. $C_{2-6}$ alkynyl), optionally substituted $C_{6-12}$ aryl, optionally substituted 3 to 10 membered heterocycle, optionally substituted $C_{6-12}$ aralkyl (e.g. $C_{7-12}$ aralkyl) or optionally substituted 3 to 10 membered heteroaralkyl (e.g. heteroaralkyl having a 3 to 9 membered heterocyclic group and a $C_{1-6}$ alkylene group);

$R_2$ is chosen from H or

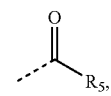

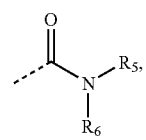

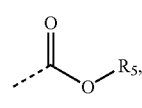

$R_3$ and $R_4$ are each independently chosen from H, optionally substituted $C_{1-10}$ alkyl (e.g. $C_{1-6}$ alkyl), optionally substituted $C_{2-10}$ alkenyl (e.g. $C_{2-6}$ alkenyl), optionally substituted $C_{2-10}$ alkynyl (e.g. $C_{2-6}$ alkynyl), or optionally substituted $C_{6-12}$ aryl;

$R_5$, $R_6$ and $R_7$ are each independently chosen from H, optionally substituted $C_{1-10}$ alkyl (e.g. $C_{1-6}$ alkyl), optionally substituted $C_{2-10}$ alkenyl (e.g. $C_{2-6}$ alkenyl), optionally substituted $C_{2-10}$ alkynyl (e.g. $C_{2-6}$ alkynyl), optionally substituted $C_{6-12}$ aryl, optionally substituted 3 to 10 membered heterocycle, optionally substituted $C_{6-12}$ aralkyl (e.g. $C_{7-12}$ aralkyl) or optionally substituted 3 to 10 membered heteroaralkyl (e.g. heteroaralkyl having a 3 to 9 membered heterocyclic group and a $C_{1-6}$ alkylene group); or $R_5$ and $R_6$ can be taken together to form an optionally substituted 3 to 10 membered heterocycle.

According to a further aspect, the present invention provides novel compounds represented by formula (I):

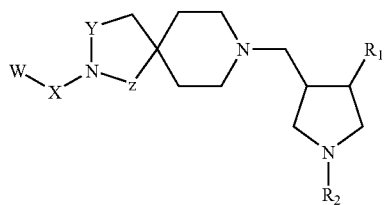

(I)

or pharmaceutically acceptable salts, hydrates or solvates thereof, wherein X, Y and Z are each independently chosen from $CH_2$, $C=O$ or $CR_3R_4$;

W is chosen from H, $C_{1-6}$ alkyl, $C_{6-12}$ aryl, 3 to 10 membered heterocycle, $C_{6-12}$ aralkyl or $C_{3-10}$ heteroaralkyl;

$R_1$ is chosen from H, $C_{1-6}$ alkyl, $C_{6-12}$ aryl, 3 to 10 membered heterocycle, $C_{6-12}$ aralkyl or $C_{3-10}$ heteroaralkyl;

$R_2$ is chosen from H or

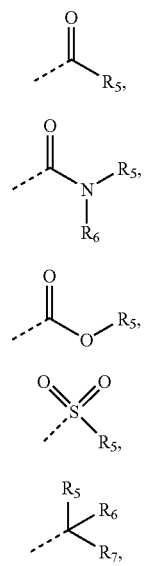

$R_3$ and $R_4$ are each independently chosen from H, $C_{1-6}$ alkyl or $C_{6-12}$ aryl;

$R_5$ is chosen from H, $C_{1-10}$ alkyl, $C_{6-12}$ aryl, 3 to 10 membered heterocycle, $C_{6-12}$ aralkyl or 3 to 10 membered heteroaralkyl and $R_6$ is chosen from H or $C_{1-10}$ alkyl or $R_5$ and $R_6$ can be taken together to form a 3 to 10 membered heterocycle;

$R_7$ is chosen from H, $C_{1-10}$ alkyl.

In another aspect, there is provided a method of modulating chemokine receptor activity in a subject comprising administering to the subject a therapeutically effective amount of a compound of formula (I) or composition of the invention.

In still another aspect, there is provided a method for prevention or treatment of certain inflammatory diseases, immunoregulatory diseases, organ transplantation reactions and in the prevention and treatment of infectious diseases such as HIV infections in a subject in need of such treatment comprising administering to the subject a therapeutically effective amount of a compound of formula (I) or composition of the invention.

In still another aspect, there is provided a method for the prevention or treatment of diseases associated with the modulation of CCR5 chemokine receptor activity in a subject in need of such treatment comprising administering to the subject a therapeutically effective amount of a compound of formula (I) or composition of the invention.

In still another aspect, there is provided a method for blocking cellular entry of HIV in a subject comprising administering to the subject in need thereof a therapeutically effective amount of a compound of formula (I) or composition of the invention to block HIV from cellular entry in said subject.

In still another aspect, there is provided a method for the prevention or treatment of diseases associated with the modulation of chemokine receptor activity in a subject in need of such treatment comprising administering to the subject a pharmaceutical combination comprising at least one compound of formula (I) and at least one further therapeutic agent.

In another aspect, there is provided a pharmaceutical formulation comprising the compound of the invention in combination with a pharmaceutically acceptable carrier or excipient.

In another aspect of the invention is the use of a compound according to formula (I), for the manufacture of a medicament for the prevention or treatment of diseases associated with the modulation of chemokine receptor activity.

DETAILED DESCRIPTION OF THE INVENTION

In one embodiment, compounds of the present invention comprise those wherein the following embodiments are present, either independently or in combination.

In one embodiment, the present invention provides novel compounds represented by formula (I):

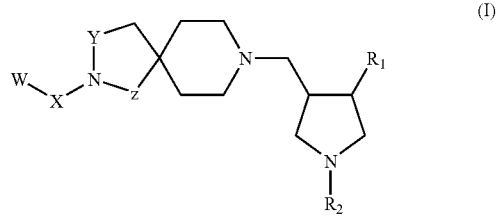

(I)

or pharmaceutically acceptable salts, hydrates or solvates thereof wherein X, Y, Z, W, $R_1$ and $R_2$ are defined above.

In one embodiment, the present invention provides novel compounds represented by formula (Ia):

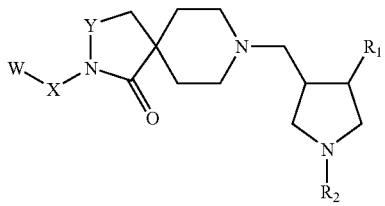

or pharmaceutically acceptable salts, hydrates or solvates thereof wherein X, Y, W, $R_1$ and $R_2$ are defined above.

In one embodiment, the present invention provides novel compounds represented by formula (Ib):

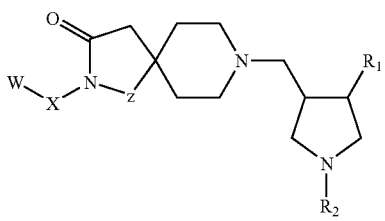

or pharmaceutically acceptable salts, hydrates or solvates thereof wherein X, Z, W, $R_1$ and $R_2$ are defined above.

In one embodiment, the present invention provides novel compounds represented by formula (Ic):

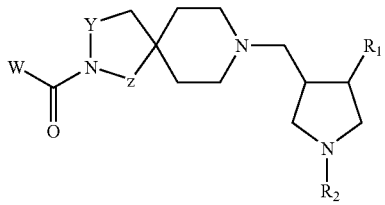

or pharmaceutically acceptable salts, hydrates or solvates thereof wherein Y, Z, W, $R_1$ and $R_2$ are defined above.

In one embodiment, the compounds of the present invention are represented by formula (Id):

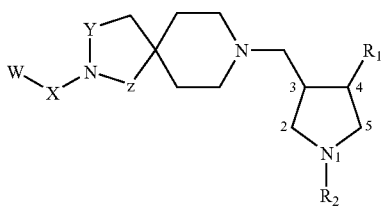

or pharmaceutically acceptable salts, hydrates or solvates thereof wherein X, Y, Z, W, $R_1$ and $R_2$ are defined above.

In one embodiment, the compounds of the present invention are in the (3R,4R)-diastereomer;

In one embodiment, the compounds of the present invention are in the (3S,4R)-diastereomer;
In one embodiment, the compounds of the present invention are in the (3R,4S)-diastereomer;
In one embodiment, the compounds of the present invention are in the (3S,4S)-diastereomer.

In one embodiment, W is chosen from optionally substituted $C_{6-12}$ aryl or optionally substituted 3 to 10 membered heterocycle.

In a further embodiment, W is optionally substituted $C_{6-12}$ aryl.

In a further embodiment, W is optionally substituted 3 to 10 membered heterocycle.

In further embodiments:
W is phenyl;
W is phenyl substituted with at least one halogen;
W is phenyl substituted with Br;
W is phenyl substituted with F;
W is phenyl substituted with Cl;
W is phenyl substituted with a $C_{1-3}$ alkoxy;
W is phenyl substituted with methoxy;
W is phenyl substituted with $SO_2C_{1-3}$alkyl;
W is phenyl substituted with methanesulfonyl;
W is phenyl substituted with difluoromethoxy;
W is phenyl substituted with trifluoromethoxy;
W is phenyl substituted with trifluoromethyl;
W is phenyl substituted with CN;
W is phenyl substituted with pyrrazoyl;
W is phenyl optionally substituted in the para (p) position.
W is pyridine.

In a further embodiment, $R_1$ is chosen from optionally substituted $C_{6-12}$ aryl.

In a further embodiment, $R_1$ is phenyl.

In a further embodiment, $R_2$ is:

wherein:
$R_5$ is methyl;
$R_5$ is ethyl;
$R_5$ is isopropyl;
$R_5$ is cyclopropyl;
$R_5$ is cyclobutyl;
$R_5$ is cyclopentyl;
$R_5$ is cyclohexyl;
$R_5$ is cycloheptyl;
$R_5$ is 4,4-difluorocyclohexyl;
$R_5$ is $CH_2$-cyclopropyl;
$R_5$ is $CH_2$-cyclobutyl;
$R_5$ is $CH_2$-cyclopentyl;
$R_5$ is $CH_2$-cyclohexyl.
$R_5$ is phenyl;
$R_5$ is phenyl substituted with at least one methyl;
$R_5$ is phenyl substituted with at least one halogen;
$R_5$ is phenyl substituted with at least one Cl;
$R_5$ is phenyl substituted with at least one Br;
$R_5$ is phenyl substituted with at least one F;
$R_5$ is phenyl substituted with at least one methoxy.
$R_5$ is benzyl;
$R_5$ is benzyl substituted with at least one methyl;
$R_5$ is benzyl substituted with at least one halogen;
$R_5$ is benzyl substituted with at least one Cl;

$R_5$ is benzyl substituted with at least one Br;
$R_5$ is benzyl substituted with at least one F;
$R_5$ is benzyl substituted with at least one methoxy.
$R_5$ is pyridine.
$R_5$ is furane.
$R_5$ is thiophene.

In a further embodiment, $R_2$ is:

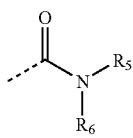

(III)

wherein:
$R_5$ is cyclopropyl, cyclopentyl, phenyl and $R_6$ is H;
$R_5$ and $R_6$ are methyl;
$R_5$ and $R_6$ are taken together to form a morpholine, a pyrrolidine, or a 3,3-difluoropyrrolidine.

In a further embodiment, $R_2$ is:

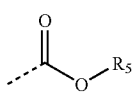

(IV)

wherein $R_5$ is methyl, ethyl, isopropyl, cyclopentyl, cyclohexyl and tert-butyl.

In a further embodiment, $R_2$ is:

(V)

wherein $R_5$ is ethyl, isopropyl, cyclopropyl and phenyl.

In a further embodiment, $R_2$ is:

(VI)

wherein:
$R_5$, $R_6$ and $R_7$ are H.
$R_5$ is isopropyl, cyclopropyl, cyclohexyl, tetrahydropyran, 4,4-difluorocyclohexyl, phenyl and $R_6$ and $R_7$ are H.
$R_5$ and $R_6$ are methyl and $R_7$ are H.

In a further embodiment, $R_3$ is chosen from H or $C_{1-10}$ alkyl.

In one embodiment, $R_3$ is H.

The compounds of the present inventions have at least two asymmetric centers at the C-3 and C-4. As 2 optical isomers can independently be obtained from each asymmetric center, it is intended that all the possible optical isomers and diastereomers in mixtures and as pure or partially purified compounds are included in this invention.

In one embodiment, the compounds of the present invention are the (+) diastereoisomers having a diastereoisomeric excess of 99%.

In one embodiment, the compounds of the present invention are the (+) diastereoisomers having a diastereoisomeric excess of 95%.

In one embodiment, the compounds of the present invention are the (+) diastereoisomers having a diastereoisomeric excess of 90%.

In one embodiment, the compounds of the present invention are the (−) diastereoisomers having a diastereoisomeric excess of 99%.

In one embodiment, the compounds of the present invention are the (−) diastereoisomers having a diastereoisomeric excess of 95%.

In one embodiment, the compounds of the present invention are the (−) diastereoisomers having a diastereoisomeric excess of 90%.

In one embodiment the compounds of the present invention comprise diastereomers where C-3 and C-4 substituents are in the trans configuration.

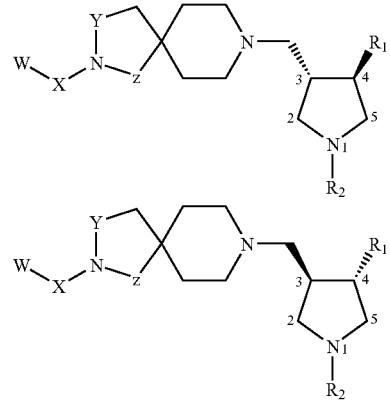

In one embodiment, there is provided a method of modulating chemokine receptor activity in a subject comprising administering to the subject a therapeutically effective amount of a compound of formula (I) or composition of the invention.

In another embodiment, there is provided a method for the prevention or treatment of diseases associated with the modulation of chemokine receptor activity in a subject in need of such treatment comprising administering to the subject a therapeutically effective amount of a compound of formula (I) or composition of the invention.

In a further embodiment, there is provided a method for prevention or treatment of certain inflammatory diseases, immunoregulatory diseases, organ transplantation reactions and in the prevention and treatment of infectious diseases such as HIV infections in a subject in need of such treatment comprising administering to the subject a therapeutically effective amount of a compound of formula (I) or composition of the invention.

In another embodiment, there is provided a method for the prevention or treatment of diseases associated with the modulation of CCR5 chemokine receptor activity in a subject in need of such treatment comprising administering to the subject a therapeutically effective amount of a compound of formula (I) or composition of the invention.

In still another aspect, there is provided a method for blocking cellular entry of HIV in a subject in need thereof comprising administering to the subject a therapeutically effective amount of a compound of formula (I) to block HIV from cellular entry in said subject.

In still another aspect, there is provided a method for prevention or treatment of HIV infections in a subject in need of such treatment comprising administering to the subject a therapeutically effective amount of a compound of formula (I) or composition of the invention.

In still another aspect, there is provided a method for delaying the onset of AIDS or treating AIDS in a subject in need of such treatment comprising administering to the subject a therapeutically effective amount of a compound of formula (I) or composition of the invention.

In a further embodiment, there is provided a method for the prevention or treatment of diseases associated with the modulation of chemokine receptor activity in a subject in need of such treatment comprising administering to the subject a pharmaceutical combination comprising at least one compound of formula (I) and at least one further therapeutic agent.

In a further embodiment, there is provided a method for the prevention or treatment of diseases associated with the modulation of CCR5 chemokine receptor activity in a subject in need of such treatment comprising administering to the subject a pharmaceutical combination comprising at least one compound of formula (I) and at least one further therapeutic agent.

In still another aspect, there is provided a method for blocking cellular entry of HIV in a subject or for the prevention or treatment of HIV infections in a subject in need of such treatment comprising administering to the subject a pharmaceutical combination comprising at least one compound of formula (I) and at least one further therapeutic agent.

In still another aspect, there is provided a method for delaying the onset of AIDS or treating AIDS in a subject in need of such treatment comprising administering to the subject a pharmaceutical combination comprising at least one compound of formula (I) and at least one further therapeutic agent.

In another embodiment, there is provided a combination useful for the prevention or treatment of diseases associated with the modulation of chemokine receptor activity which is a therapeutically effective amount of a compound of formula (I) and therapeutically effective amount of at least one further therapeutic agent.

In one embodiment, combinations of the present invention comprise those wherein the following embodiments are present, either independently or in combination.

In a further embodiment, the pharmaceutical combinations of this invention may contain at least one further therapeutic agent chosen from an agent used in inflammatory diseases, immunoregulatory diseases and in organ transplantation reactions.

In another embodiment, the pharmaceutical combination of this invention may contain at least one further therapeutic agent which is an antiviral agent.

In one embodiment, the pharmaceutical combination of this invention may contain at least one further antiviral agent which is chosen from nucleoside and nucleotide analog reverse transcriptase inhibitors, non-nucleoside reverse transcriptase inhibitors, protease inhibitors, attachment and fusion inhibitors, integrase inhibitors or maturation inhibitors.

In one embodiment, the pharmaceutical combinations of this invention may contain at least one other antiviral agent which is a nucleoside and nucleotide analog reverse transcriptase inhibitors chosen from 3TC (lamivudine, Epivir®), AZT (zidovudine, Retrovir®), Emtricitabine (Coviracil®, formerly FTC), d4T (2',3'-dideoxy-2',3'-didehydro-thymidine, stavudine and Zerit®), tenofovir (Viread®), 2',3'-dideoxyinosine (ddI, didanosine, Videx®), 2',3'-dideoxycytidine (ddC, zalcitabine, Hivid®), Combivir® (AZT/3TC or zidovudine/lamivudine combination), Trivizir® (AZT/3TC/abacavir or zidovudine/lamivudine/abacavir combination), abacavir (1592U89, Ziagen®), SPD-754, ACH-126,443 (Beta-L-Fd4C), Alovudine (MIV-310), DAPD (amdoxovir), Racivir, 9-[(2-hydroxymethyl)-1,3-dioxolan-4-yl]guanine or 2-amino-9-[(2-hydroxymethyl)-1,3-dioxolan-4-yl]adenine.

In another embodiment, the pharmaceutical combination of this invention may contain at least one other antiviral agent which is a non-nucleoside reverse transcriptase inhibitor chosen from Nevirapine (Viramune®, NVP, BI-RG-587), delavirdine (Rescriptor®, DLV), efavirenz (DMP 266, Sustiva®), (+)-Calanolide A, Capravirine (AG1549, formerly S-1153), DPCO83, MIV-150, TMC120, TMC125 or BHAP (delavirdine), calanolides or L-697,661 (2-Pyridinone 3benzoxazolMeNH derivative).

In another embodiment, the pharmaceutical combination of this invention may contain at least one other antiviral agent which is a protease inhibitor chosen from nelfinavir (Viracept®, NFV), amprenavir (141W94, Agenerase®), indinavir (MK-639, IDV, Crixivan®), saquinavir (Invirase®, Fortovase®, SQV), ritonavir (Norvir®, RTV), lopinavir (ABT-378, Kaletra®), Atazanavir (BMS232632), mozenavir (DMP-450), fosamprenavir (GW433908), R0033-4649, Tipranavir (PNU-140690), TMC114 or VX-385.

In another embodiment, the pharmaceutical combination of this invention may contain at least one other antiviral agent which is an attachment and fusion inhibitor chosen from T-20 (enfuvirtide, Fuzeon®), T-1249, Schering C(SCH-C), Schering D (SCH-D), FP21399, PRO-140, PRO542, PRO452, TNX-355, GW873140 (AK602), TAK-220, UK-427,857 or soluble CD4, CD4 fragments, CD4-hybrid molecules, BMS-806, BMS-488043, AMD070, AMD3100 or KRH-2731.

In another embodiment, the pharmaceutical combination of this invention may contain at least one other antiviral agent which is an integrase inhibitor chosen from S-1360, L-870,810, L-870,812 or C-2507.

In another embodiment, the pharmaceutical combination of this invention may contain at least one other antiviral agent which is a maturation inhibitor and is PA-457.

In another embodiment, the pharmaceutical combination of this invention may contain at least one other antiviral agent which is a zinc finger inhibitor and is azodicarbonamide (ADA).

In another embodiment, the pharmaceutical combination of this invention may contain at least one other antiviral agent which is an antisense drug and is HGTV43.

In another embodiment, the pharmaceutical combination of this invention may contain at least one other antiviral agent which is an immunomodulator, immune stimulator or cytokine chosen from interleukin-2 (IL-2, Aldesleukin, Proleukin), granulocyte macrophage colony stimulating factor (GM-CSF), erythropoietin, Multikine, Ampligen, thymomodulin, thymopentin, foscarnet, HE2000, Reticulose, Murabutide, Resveratrol, HRG214, HIV-1 Immunogen (Remune) or EP HIV-1090.

In another embodiment, the pharmaceutical combination of this invention may contain at least one other antiviral agent chosen from 2',3'-dideoxyadenosine, 3'-deoxythymidine, 2',3'-dideoxy-2',3'-didehydrocytidine and ribavirin; acyclic nucleosides such as acyclovir, ganciclovir; interferons such as alpha-, beta-and gamma-interferon; glucuronation inhibitors such as probenecid; or TIBO drugs, HEPT, TSAO derivatives.

The combinations referred to above may conveniently be presented for use in the form of a pharmaceutical formulation and thus pharmaceutical formulations comprising a combination as defined above together with a pharmaceutically acceptable carrier thereof comprises a further aspect of the invention.

The individual components of such combinations may be administered either sequentially or simultaneously in separate or combined pharmaceutical formulations.

In a further embodiment, the said compound of formula (I) and said therapeutic agent are administered sequentially.

In a further embodiment, the said compound of formula (I) and said therapeutic agent are administered simultaneously.

In one embodiment, the present invention further provides a pharmaceutical composition comprising at least one compound having the formula (I) or pharmaceutically acceptable salts or pharmaceutically acceptable hydrates or pharmaceutically acceptable solvates thereof and at least one pharmaceutically acceptable carrier or excipient.

In another embodiment, the invention provides the use of a compound having the formula (I) for the manufacture of a medicament for prevention and treatment of diseases associated with the modulation of CCR5 chemokine receptor activity in a host comprising administering a therapeutically effective amount of a compound of formula (I).

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

The term "alkyl" represents a linear, branched or cyclic hydrocarbon moiety having 1 to 10 carbon atoms, and is optionally substituted. For example, suitable substituents include halogen, amino, amidino, amido, azido, cyano, guanido, hydroxyl, nitro, nitroso, urea, $OS(O)_2R_{19}$ (wherein $R_{19}$ is selected from $C_{1-6}$ alkyl, $C_{6-12}$ aryl or 3 to 10 membered heterocycle), $OS(O)_2OR_{20}$ (wherein $R_{20}$ is selected from H, $C_{1-6}$ alkyl, $C_{6-12}$ aryl or 3 to 10 membered heterocycle), $S(O)_2OR_{21}$ (wherein $R_{21}$ is selected from H, $C_{1-6}$ alkyl, $C_{6-12}$ aryl or 3 to 10 membered heterocycle), $S(O)_{0-2}R_{22}$ (wherein $R_{22}$ is selected from H, $C_{1-6}$ alkyl, $C_{6-12}$ aryl or 3 to 10 membered heterocycle), $OP(O)OR_{23}OR_{24}$, $P(O)OR_{23}OR_{24}$ (wherein $R_{23}$ and $R_{24}$ are each independently selected from H or $C_{1-6}$ alkyl), $C(O)R_{25}$ (wherein $R_{25}$ is selected from H, $C_{1-6}$ alkyl, $C_{6-12}$ aryl or 3 to 10 membered heterocycle), $C(O)OR_{26}$ (wherein $R_{26}$ is selected from H, $C_{1-6}$ alkyl, $C_{6-12}$ aryl, $C_{6-12}$ aralkyl (e.g. $C_{7-12}$ aralkyl) or 3 to 10 membered heterocycle), $NR_{27}C(O)R_{28}$, $C(O)NR_{27}R_{28}$ (wherein $R_{27}$ is H or $C_{1-6}$ alkyl and $R_{28}$ is selected from H, $C_{1-6}$ alkyl, $C_{6-12}$ aryl, $C_{6-12}$ aralkyl (e.g. $C_{7-12}$ aralkyl) or 3 to 10 membered heterocycle, or $R_{27}$ and $R_{28}$ are taken together with the atoms to which they are attached to form a 3 to 10 membered heterocycle), $SO_2NR_{29}R_{30}$, $NR_{29}SO_2R_{30}$ (wherein $R_{29}$ and $R_{30}$ are each independently selected from the group consisting of H, $C_{1-6}$ alkyl, $C_{6-12}$ aryl, 3 to 10 membered heterocycle and $C_{6-12}$ aralkyl (e.g. $C_{7-12}$ aralkyl)), $C(R_{31})NR_{32}$ or $C(R_{31})NOR_{32}$ (wherein $R_{31}$, and $R_{32}$ are each independently selected from the group consisting of H, $C_{1-6}$ alkyl, or $C_{6-12}$ aryl).

Preferred substituents for the alkyl groups include halogen (Br, Cl, I or F), cyano, nitro, oxo, amino, COOH, COO—$C_{1-4}$ alkyl, CO—$C_{1-4}$ alkyl, and phenyl.

Examples include but are not limited to methyl, ethyl, propyl, isopropyl, butyl, isobutyl, sec-butyl, tert-butyl, pentyl, isopentyl, neopentyl, tert-pentyl, hexyl, isohexyl, neohexyl and cyclohexyl, which in each case are unsubstituted or optionally substituted one or more times by, for example, halogen (Br, Cl, I or F), cyano, nitro, oxo, amino, COOH, COO—$C_{1-4}$ alkyl, CO—$C_{1-4}$ alkyl, and/or phenyl.

The term alkyl is also meant to include alkyls in which one or more hydrogen atom is replaced by a halogen, ie. an alkylhalide. Examples include but are not limited to trifluoromethyl, difluoromethyl, fluoromethyl, trichloromethyl, dichloromethyl, chloromethyl, trifluoroethyl, difluoroethyl, fluoroethyl, trichloroethyl, dichloroethyl, chloroethyl, chlorofluoromethyl, chlorodifluoromethyl, dichlorofluoroethyl.

The term "alkenyl" refers to alkyl groups may have one or more double bonds in the chain. The term "alkynyl" refers to alkyl groups may have one or more triple bonds in their chain. The alkenyl and alkynyl groups can be optionally substituted as described above for the alkyl groups.

Preferred substituents for the alkenyl and alkynyl groups include halogen (Br, Cl, I or F), cyano, nitro, oxo, amino, COOH, COO—$C_{1-4}$ alkyl, CO—$C_{1-4}$ alkyl, and phenyl.

Examples of alkenyl and alkynyl groups include but are not limited to allyl, vinyl, acetylenyl, ethylenyl, propenyl, isopropenyl butenyl, isobutenyl, hexenyl, butadienyl, pentenyl, pentadienyl, hexenyl, hexadienyl, hexatrienyl, heptenyl, heptadienyl, heptatrienyl, octenyl, octadienyl, octatrienyl, octatetraenyl, propynyl, butynyl, pentynyl, hexynyl, cyclohexenyl and cyclohexdienyl, which in each case are unsubstituted or optionally substituted one or more times by, for example, halogen (Br, Cl, I or F), cyano, nitro, oxo, amino, COOH, COO—$C_{1-4}$ alkyl, CO—$C_{1-4}$ alkyl, and/or phenyl.

The term "alkoxyl" or "O—$C_{x-y}$ alkyl" (e.g., O—$C_{1-6}$ alkyl) represents an alkyl which is covalently bonded to the adjacent atom through an oxygen atom. Examples include but are not limited to methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, isohexyloxy and neohexyloxy. The alkoxy groups can be optionally substituted as described above for the alkyl groups.

Preferred substituents for the alkoxy groups include halogen (Br, Cl, I or F), cyano, nitro, oxo, amino, COOH, COO—$C_{1-4}$ alkyl, CO—$C_{1-4}$ alkyl, and phenyl.

The term "alkylamino" represents an alkyl which is covalently bonded to the adjacent atom through a nitrogen atom and may be monoalkylamino or dialkylamino, wherein the alkyl groups may be the same or different. Examples include but are not limited to methylamino, dimethylamino, ethylamino, diethylamino, methylethylamino, propylamino, isopropylamino, butylamino, isobutylamino, sec-butylamino, tert-butylamino, pentylamino, isopentylamino, neopentylamino, tert-pentylamino, hexylamino, isohexylamino and neohexylamino.

The term "alkyloxycarbonyl" represents an alkyloxy which is covalently bonded to the adjacent atom through carbonyl (C=O). Examples include but are not limited to methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, tert-pentyloxycarbonyl, hexyloxycarbonyl, isohexyloxycarbonyl and neohexyloxycarbonyl.

The term "amidino" represents —C(=NR$_8$)NR$_9$R$_{10}$, wherein R$_8$, R$_9$ and R$_{10}$ are each independently selected from H, C$_{1-6}$ alkyl, C$_{6-12}$ aryl or C$_{6-12}$ aralkyl (e.g. C$_{7-12}$ aralkyl), or R$_9$ and R$_{10}$ are taken together with the nitrogen to which they are attached to form a 3 to 10 membered heterocycle.

The term "amido" represents —CONH$_2$, —CONHR$_{11}$ and —CONR$_{11}$R$_{12}$ wherein R$_{11}$ and R$_{12}$ are each independently selected from C$_{1-6}$ alkyl, C$_{6-12}$ aryl, 3 to 10 membered heterocycle or C$_{6-12}$ aralkyl (e.g. C$_{7-12}$ aralkyl), or R$_{11}$ and R$_{12}$ are taken together with the nitrogen to which they are attached to form a 3 to 10 membered heterocycle.

The term "amino" represents a derivative of ammonia obtained by substituting one or more hydrogen atom and include —NH$_2$, —NHR$_{13}$ and —NR$_{13}$R$_{14}$, wherein R$_{13}$ and R$_{14}$ are each independently selected from C$_{1-6}$ alkyl, C$_{6-12}$ aryl or C$_{6-12}$ aralkyl (e.g. C$_{7-12}$ aralkyl), or R$_{13}$ and R$_{14}$ are taken together with the nitrogen to which they are attached to form a 3 to 10 membered heterocycle.

The term "aryl" represents a carbocyclic moiety containing at least one benzenoid-type ring (ie. may be monocyclic or polycyclic), and which may be optionally substituted with one or more substituents. For example, suitable substituents include halogen, amino, amidino, amido, azido, cyano, guanido, hydroxyl, nitro, nitroso, urea, OS(O)$_2$R$_{19}$ (wherein R$_{19}$ is selected from C$_{1-6}$ alkyl, C$_{6-12}$ aryl or 3 to 10 membered heterocycle), OS(O)$_2$OR$_{20}$ (wherein R$_{20}$ is selected from H, C$_{1-6}$ alkyl, C$_{6-12}$ aryl or 3 to 10 membered heterocycle), S(O)$_2$OR$_{21}$ (wherein R$_{21}$ is selected from H, C$_{1-6}$ alkyl, C$_{6-12}$ aryl or 3 to 10 membered heterocycle), S(O)$_{0-2}$R$_{22}$ (wherein R$_{22}$ is selected from H, C$_{1-6}$ alkyl, C$_{6-12}$ aryl or 3 to 10 membered heterocycle), OP(O)OR$_{23}$OR$_{24}$, P(O)OR$_{23}$OR$_{24}$ (wherein R$_{23}$ and R$_{24}$ are each independently selected from H or C$_{1-6}$ alkyl), C(O)R$_{25}$ (wherein R$_{25}$ is selected from H, C$_{1-6}$ alkyl, C$_{6-12}$ aryl or 3 to 10 membered heterocycle), C(O)OR$_{26}$ (wherein R$_{26}$ is selected from H, C$_{1-6}$ alkyl, C$_{6-12}$ aryl, C$_{6-12}$ aralkyl (e.g. C$_{7-12}$ aralkyl) or 3 to 10 membered heterocycle), NR$_{27}$C(O)R$_{28}$, C(O)NR$_{27}$R$_{28}$ (wherein R$_{27}$ is H or C$_{1-6}$ alkyl and R$_{28}$ is selected from H, C$_{1-6}$ alkyl, C$_{6-12}$ aryl, C$_{6-12}$ aralkyl (e.g. C$_{7-12}$ aralkyl) or 3 to 10 membered heterocycle, or R$_{27}$ and R$_{28}$ are taken together with the atoms to which they are attached to form a 3 to 10 membered heterocycle), SO$_2$NR$_{29}$R$_{30}$, NR$_{29}$SO$_2$R$_{30}$ (wherein R$_{29}$ and R$_{30}$ are each independently selected from the group consisting of H, C$_{1-6}$ alkyl, C$_{6-12}$ aryl, 3 to 10 membered heterocycle and C$_{6-12}$ aralkyl (e.g. C$_{7-12}$ aralkyl)), C(R$_{31}$)NR$_{32}$ or C(R$_{31}$)NOR$_{32}$ (wherein R$_{31}$ and R$_{32}$ are each independently selected from the group consisting of H, C$_{1-6}$ alkyl, or C$_{6-12}$ aryl).

Preferred substituents for the aryl groups include halogen (Br, Cl, I or F), cyano, nitro, oxo, amino, C$_{1-4}$ alkyl (e.g., CH$_3$, C$_2$H$_5$, isopropyl), C$_{1-4}$ alkoxy (e.g., OCH$_3$, OC$_2$H$_5$), halogenated C$_{1-4}$ alkyl (e.g., CF$_3$, CHF$_2$), halogenated C$_{1-4}$ alkoxy (e.g., OCF$_3$, OC$_2$F$_5$), COOH, COO—C$_{1-4}$ alkyl, CO—C$_{1-4}$ alkyl, C$_{1-4}$ alkyl-S— (e.g., CH$_3$S, C$_2$H$_5$S), halogenated C$_{1-4}$ alkyl-S— (e.g., CF$_3$S, C$_2$F$_5$S), benzyloxy, and pyrazolyl.

Examples include but are not limited to phenyl, tolyl, dimethylphenyl, aminophenyl, anilinyl, naphthyl, anthryl, phenanthryl or biphenyl, which in each case is unsubstituted or substituted one or more times by, for example, halogen (Br, Cl, I or F), cyano, nitro, oxo, amino, C$_{1-4}$ alkyl (e.g., CH$_3$, C$_2$H$_5$, isopropyl), C$_{1-4}$ alkoxy (e.g., OCH$_3$, OC$_2$H$_5$), halogenated C$_{1-4}$ alkyl (e.g., CF$_3$, CHF$_2$), halogenated C$_{1-4}$ alkoxy (e.g., OCF$_3$, OC$_2$F$_5$), COOH, COO—C$_{1-4}$ alkyl, COO—C$_{1-4}$ alkyl, C$_{1-4}$ alkyl-S— (e.g., CH$_3$S, C$_2$H$_5$S), halogenated C$_{1-4}$ alkyl-S— (e.g., CF$_3$S, C$_2$F$_5$S), benzyloxy, and pyrazolyl.

The term "aryloxy" represents an aryl which is covalently bonded to the adjacent atom through an oxygen atom. The aryloxy groups can be optionally substituted as described above for the aryl groups.

Preferred substituents for the aryloxy groups include halogen (Br, Cl, I or F), cyano, nitro, oxo, amino, C$_{1-4}$ alkyl (e.g., CH$_3$, C$_2$H$_5$, isopropyl), C$_{1-4}$ alkoxy (e.g., OCH$_3$, OC$_2$H$_5$), halogenated C$_{1-4}$ alkyl (e.g., CF$_3$, CHF$_2$), halogenated C$_{1-4}$ alkoxy (e.g., OCF$_3$, OC$_2$F$_5$), COOH, COO—C$_{1-4}$ alkyl, CO—C$_{1-4}$ alkyl, C$_{1-4}$ alkyl-S— (e.g., CH$_3$S, C$_2$H$_5$S), halogenated C$_{1-4}$ alkyl-S— (e.g., CF$_3$S, C$_2$F$_5$S), benzyloxy, and pyrazolyl.

Examples of aryloxy include but are not limited to phenoxy and naphthyloxy, which in each case is unsubstituted or substituted one or more times by, for example, halogen (Br, Cl, I or F), cyano, nitro, oxo, amino, C$_{1-4}$ alkyl (e.g., CH$_3$, C$_2$H$_5$, isopropyl), C$_{1-4}$ alkoxy (e.g., OCH$_3$, OC$_2$H$_5$), halogenated C$_{1-4}$ alkyl (e.g., CF$_3$, CHF$_2$), halogenated C$_{1-4}$ alkoxy (e.g., OCF$_3$, OC$_2$F$_5$), COOH, COO—C$_{1-4}$ alkyl, CO—C$_{1-4}$ alkyl, C$_{1-4}$ alkyl-S— (e.g., CH$_3$S, C$_2$H$_5$S), halogenated C$_{1-4}$ alkyl-S— (e.g., CF$_3$S, C$_2$F$_5$S), benzyloxy, and pyrazolyl.

The term "aralkyl" represents an aryl group attached to the adjacent atom by a C$_{1-6}$alkyl. The arylalkyl groups can be optionally substituted as described above for the aryl groups.

Preferred substituents for the arylalkyl groups include halogen (Br, Cl, I or F), cyano, nitro, oxo, amino, C$_{1-4}$ alkyl (e.g., CH$_3$, C$_2$H$_5$, isopropyl), C$_{1-4}$ alkoxy (e.g., OCH$_3$, OC$_2$H$_5$), halogenated C$_{1-4}$ alkyl (e.g., CF$_3$, CHF$_2$), halogenated C$_{1-4}$ alkoxy (e.g., OCF$_3$, OC$_2$F$_5$), COOH, COO—C$_{1-4}$ alkyl, CO—C$_{1-4}$ alkyl, C$_{1-4}$ alkyl-S— (e.g., CH$_3$S, C$_2$H$_5$S), halogenated C$_{1-4}$ alkyl-S— (e.g., CF$_3$S, C$_2$F$_5$S), benzyloxy, and pyrazolyl.

Examples of arylalkyl include but are not limited to benzyl, benzhydryl, trityl, phenethyl, 3-phenylpropyl, 2-phenylpropyl, 4-phenylbutyl and naphthylmethyl, which in each case is unsubstituted or substituted one or more times by, for example, halogen (Br, Cl, I or F), cyano, nitro, oxo, amino, C$_{1-4}$ alkyl (e.g., CH$_3$, C$_2$H$_5$, isopropyl), C$_{1-4}$ alkoxy (e.g., OCH$_3$, OC$_2$H$_5$), halogenated C$_{1-4}$ alkyl (e.g., CF$_3$, CHF$_2$), halogenated C$_{1-4}$ alkoxy (e.g., OCF$_3$, OC$_2$F$_5$), COOH, COO—C$_{1-4}$ alkyl, CO—C$_{1-4}$ alkyl, C$_{1-4}$ alkyl-S— (e.g., CH$_3$S, C$_2$H$_5$S), halogenated C$_{1-4}$ alkyl-S— (e.g., CF$_3$S, C$_2$F$_5$S), benzyloxy, and pyrazolyl.

The term "aralkyloxy" represents an aralkyl which is covalently bonded to the adjacent atom through an oxygen atom. The arylalkyloxy groups can be optionally substituted as described above for the aryl groups.

Preferred substituents for the arylalkyloxy groups include halogen (Br, Cl, I or F), cyano, nitro, oxo, amino, C$_{1-4}$ alkyl (e.g., CH$_3$, C$_2$H$_5$, isopropyl), C$_{1-4}$ alkoxy (e.g., OCH$_3$, OC$_2$H$_5$), halogenated C$_{1-4}$ alkyl (e.g., CF$_3$, CHF$_2$), halogenated C$_{1-4}$ alkoxy (e.g., OCF$_3$, OC$_2$F$_5$), COOH, COO—C$_{1-4}$ alkyl, CO—C$_{1-4}$ alkyl, C$_{1-4}$ alkyl-S— (e.g., CH$_3$S, C$_2$H$_5$S), halogenated C$_{1-4}$ alkyl-S— (e.g., CF$_3$S, C$_2$F$_5$S), benzyloxy, and pyrazolyl.

Examples of arylalkyloxy include but are not limited to benzyloxy, benzhydryloxy, trityloxy, phenethyloxy, 3-phenylpropyloxy, 2-phenylpropyloxy, 4-phenylbutyloxy and naphthylmethoxy, which in each case is unsubstituted or substituted one or more times by, for example, halogen (Br, Cl, I or F), cyano, nitro, oxo, amino, C$_{1-4}$ alkyl (e.g., CH$_3$, $C_2H_5$, isopropyl), $C_{1-4}$ alkoxy (e.g., $OCH_3$, $OC_2H_5$), halogenated $C_{1-4}$ alkyl (e.g., $CF_3$, $CHF_2$), halogenated $C_{1-4}$ alkoxy (e.g., $OCF_3$, $OC_2F_5$), COOH, COO—$C_{1-4}$ alkyl, CO—$C_{1-4}$ alkyl, $C_{1-4}$ alkyl-S— (e.g., $CH_3S$, $C_2H_5S$), halogenated $C_{1-4}$ alkyl-S— (e.g., $CF_3S$, $C_2F_5S$), benzyloxy, and pyrazolyl.

The term "guanidino" represents $NR_{15}C(=NR_{16})NR_{17}R_{18}$ wherein $R_{15}$, $R_{16}$, $R_{17}$ and $R_{18}$ are each independently selected from H, $C_{1-6}$ alkyl, $C_{6-12}$ aryl or $C_{6-12}$ aralkyl (e.g. $C_{7-12}$ aralkyl), or $R_{17}$ and $R_{18}$ are taken together with the nitrogen to which they are attached to form a 3 to 10 membered heterocycle.

The term "urea" represents —$N(R_{31})CONR_{32}R_{33}$ wherein $R_{31}$ is H or $C_{1-6}$ alkyl and wherein $R_{32}$ and $R_{33}$ are each independently selected from the group consisting of H, $C_{1-6}$ alkyl, $C_{6-12}$ aryl, 3 to 10 membered heterocycle and $C_{6-12}$ aralkyl (e.g. $C_{7-12}$ aralkyl), or $R_{32}$ and $R_{33}$ are taken together with the nitrogen to which they are attached to form a 3 to 10 membered heterocycle.

The term "halogen" is specifically a fluoride atom, chloride atom, bromide atom or iodide atom.

The term "heterocycle" represents an optionally substituted saturated, unsaturated or aromatic cyclic moiety wherein said cyclic moiety is interrupted by at least one heteroatom selected from oxygen (O), sulfur (S) or nitrogen (N). Heterocycles may be monocyclic or polycyclic rings. Suitable substituents, for example, include halogen, amino, amidino, amido, azido, cyano, guanido, hydroxyl, nitro, nitroso, urea, $OS(O)_2R_{19}$ (wherein $R_{19}$ is selected from $C_{1-6}$ alkyl, $C_{6-12}$ aryl or 3 to 10 membered heterocycle), $OS(O)_2OR_{20}$ (wherein $R_{20}$ is selected from H, $C_{1-6}$ alkyl, $C_{6-12}$ aryl or 3 to 10 membered heterocycle), $S(O)_2OR_{21}$ (wherein $R_{21}$ is selected from H, $C_{1-6}$ alkyl, $C_{6-12}$ aryl or 3 to 10 membered heterocycle), $S(O)_{0-2}R_{22}$ (wherein $R_{22}$ is selected from H, $C_{1-6}$ alkyl, $C_{6-12}$ aryl or 3 to 10 membered heterocycle), $OP(O)OR_{23}OR_{24}$, $P(O)OR_{23}OR_{24}$ (wherein $R_{23}$ and $R_{24}$ are each independently selected from H or $C_{1-6}$ alkyl), $C(O)R_{25}$ (wherein $R_{25}$ is selected from H, $C_{1-6}$ alkyl, $C_{6-12}$ aryl or 3 to 10 membered heterocycle), $C(O)OR_{26}$ (wherein $R_{26}$ is selected from H, $C_{1-6}$ alkyl, $C_{6-12}$ aryl, $C_{6-12}$ aralkyl (e.g. $C_{7-12}$ aralkyl) or 3 to 10 membered heterocycle), $NR_{27}C(O)R_{28}$, $C(O)NR_{27}R_{28}$ (wherein $R_{27}$ is H or $C_{1-6}$ alkyl and $R_{28}$ is selected from H, $C_{1-6}$ alkyl, $C_{6-12}$ aryl, $C_{6-12}$ aralkyl (e.g. $C_{7-12}$ aralkyl) or 3 to 10 membered heterocycle, or $R_{27}$ and $R_{28}$ are taken together with the atoms to which they are attached to form a 3 to 10 membered heterocycle), $SO_2NR_{29}R_{30}$, $NR_{29}SO_2R_{30}$ (wherein $R_{29}$ and $R_{30}$ are each independently selected from the group consisting of H, $C_{1-6}$ alkyl, $C_{6-12}$ aryl, 3 to 10 membered heterocycle and $C_{6-12}$ aralkyl (e.g. $C_{7-12}$ aralkyl)), $C(R_{31})NR_{32}$ or $C(R_{31})NOR_{32}$ (wherein $R_{31}$ and $R_{32}$ are each independently selected from the group consisting of H, $C_{1-6}$ alkyl, or $C_{6-12}$ aryl).

Preferred substituents for the heterocycle groups include halogen (Br, Cl, I or F), cyano, nitro, oxo, amino, $C_{1-4}$ alkyl (e.g., $CH_3$, $C_2H_5$, isopropyl), $C_{1-4}$ alkoxy (e.g., $OCH_3$, $OC_2H_5$), halogenated $C_{1-4}$ alkyl (e.g., $CF_3$, $CHF_2$), halogenated $C_{1-4}$ alkoxy (e.g., $OCF_3$, $OC_2F_5$), COOH, COO—$C_{1-4}$ alkyl, CO—$C_{1-4}$ alkyl, $C_{1-4}$ alkyl-S— (e.g., $CH_3S$, $C_2H_5S$), halogenated $C_{1-4}$ alkyl-S— (e.g., $CF_3S$, $C_2F_5S$), benzyloxy, and pyrazolyl.

Examples of heterocycles include but are not limited to azepinyl, aziridinyl, azetyl, azetidinyl, diazepinyl, dithiadiazinyl, dioxazepinyl, dioxolanyl, dithiazolyl, furanyl, isooxazolyl, isothiazolyl, imidazolyl, morpholinyl, morpholino, oxetanyl, oxadiazolyl, oxiranyl, oxazinyl, oxazolyl, piperazinyl, pyrazinyl, pyridazinyl, pyrimidinyl, piperidyl, piperidino, pyridyl, pyranyl, pyrazolyl, pyrrolyl, pyrrolidinyl, thiatriazolyl, tetrazolyl, thiadiazolyl, triazolyl, thiazolyl, thienyl, tetrazinyl, thiadiazinyl, triazinyl, thiazinyl, thiopyranyl furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl and pyridopyrimidinyl, which in each case is unsubstituted or substituted one or more times by, for example, halogen (Br, Cl, I or F), cyano, nitro, oxo, amino, $C_{1-4}$ alkyl (e.g., $CH_3$, $C_2H_5$, isopropyl), $C_{1-4}$ alkoxy (e.g., $OCH_3$, $OC_2H_5$), halogenated $C_{1-4}$ alkyl (e.g., $CF_3$, $CHF_2$), halogenated $C_{1-4}$ alkoxy (e.g., $OCF_3$, $OC_2F_5$), COOH, COO—$C_{1-4}$ alkyl, CO—$C_{1-4}$ alkyl, $C_{1-4}$ alkyl-S— (e.g., $CH_3S$, $C_2H_5S$), halogenated $C_{1-4}$ alkyl-S— (e.g., $CF_3S$, $C_2F_5S$), benzyloxy, and pyrazolyl.

The term "heteroaralkyl" represents a heterocycle group attached to the adjacent atom by a $C_{1-6}$ alkyl. The heteroaralkyl groups can be optionally substituted as described above for the heteroaryl groups.

Preferred substituents for the heteroarylalkyl groups include halogen (Br, Cl, I or F), cyano, nitro, oxo, amino, $C_{1-4}$ alkyl (e.g., $CH_3$, $C_2H_5$, isopropyl), $C_{1-4}$ alkoxy (e.g., $OCH_3$, $OC_2H_5$), halogenated $C_{1-4}$ alkyl (e.g., $CF_3$, $CHF_2$), halogenated $C_{1-4}$ alkoxy (e.g., $OCF_3$, $OC_2F_5$), COOH, COO—$C_{1-4}$ alkyl, CO—$C_{1-4}$ alkyl, $C_{1-4}$ alkyl-S— (e.g., $CH_3S$, $C_2H_5S$), halogenated $C_{1-4}$ alkyl-S— (e.g., $CF_3S$, $C_2F_5S$), benzyloxy, and pyrazolyl.

The term "independently" means that a substituent can be the same or a different definition for each item.

The term "optionally substituted" means that respective group can optionally be substituted by one or more halogen, amino, amidino, amido, azido, cyano, guanido, hydroxyl, nitro, nitroso, urea, $OS(O)_2R_{19}$ (wherein $R_{19}$ is selected from $C_{1-6}$ alkyl, $C_{6-12}$ aryl or 3 to 10 membered heterocycle), $OS(O)_2OR_{20}$ (wherein $R_{20}$ is selected from H, $C_{1-6}$ alkyl, $C_{6-12}$ aryl or 3 to 10 membered heterocycle), $S(O)_2OR_{21}$ (wherein $R_{21}$ is selected from H, $C_{1-6}$ alkyl, $C_{6-12}$ aryl or 3 to 10 membered heterocycle), $S(O)_{0-2}R_{22}$ (wherein $R_{22}$ is selected from H, $C_{1-6}$ alkyl, $C_{6-12}$ aryl or 3 to 10 membered heterocycle), $OP(O)OR_{23}OR_{24}$, $P(O)OR_{23}OR_{24}$ (wherein $R_{23}$ and $R_{24}$ are each independently selected from H or $C_{1-6}$ alkyl), $C_{1-6}$ alkyl, $C_{6-12}$ aralkyl (e.g. $C_{7-12}$ aralkyl), $C_{6-12}$ aryl, $C_{1-6}$alkoxy, $C_{6-12}$aralkyloxy (e.g. $C_{7-12}$ aralkyloxy), $C_{6-12}$aryloxy, 3 to 10 membered heterocycle, $C(O)R_{25}$ (wherein $R_{25}$ is selected from H, $C_{1-6}$ alkyl, $C_{6-12}$ aryl or 3 to 10 membered heterocycle), $C(O)OR_{26}$ (wherein $R_{26}$ is selected from H, $C_{1-6}$ alkyl, $C_{6-12}$ aryl, $C_{6-12}$ aralkyl (e.g. $C_{7-12}$ aralkyl) or 3 to 10 membered heterocycle) $NR_{27}C(O)R_{28}$ (wherein $R_{27}$ is H or $C_{1-6}$alkyl and $R_{28}$ is selected from H, $C_{1-6}$alkyl, $C_{6-12}$ aryl, $C_{6-12}$aralkyl (e.g. $C_{7-12}$ aralkyl) or 3 to 10 membered heterocycle, or $R_{27}$ and $R_{28}$ are taken together with the atoms to which they are attached to form a 3 to 10 membered heterocycle) or $SO_2NR_{29}R_{30}$ (wherein $R_{29}$ and $R_{30}$ are each independently selected from the group consisting of H, $C_{1-6}$ alkyl, $C_{6-12}$ aryl, 3 to 10 membered heterocycle and $C_{6-12}$ aralkyl (e.g. $C_{7-12}$ aralkyl)), $C(R_{31})$ $NR_{32}$ or $C(R_{31})NOR_{32}$ (wherein $R_{31}$ and $R_{32}$ are each independently selected from the group consisting of H, $C_{1-6}$ alkyl, or $C_{6-12}$ aryl).

"Oxidation levels": When there is a sulfur atom present, the sulfur atom can be at different oxidation levels, ie. S, SO or $SO_2$. All such oxidation levels are within the scope of the present invention. When there is a nitrogen atom present, the nitrogen atom can be at different oxidation levels, ie. N or NO. All such oxidation levels are within the scope of the present invention.

There is also provided "enantiomers" and "diastereoisomers" of the present invention. It will be appreciated that the compounds in accordance with the present invention can contain one or more chiral centers. The compounds in accordance with the present invention may thus exist in the form of two different optical isomers, that is (+) or (−) enantiomers or in the form of different diastereoisomers. All such enantiomers, diastereoisomers and mixtures thereof, including racemic or other ratio mixtures of individual enantiomers and diastereoisomers, are included within the scope of the invention. The single diastereoisomers can be obtained by methods well known to those of ordinary skill in the art, such as HPLC, crystallization and chromatography. The single enantiomer can be obtained by methods well known to those of ordinary skill in the art, such as chiral HPLC, enzymatic resolution and chiral auxiliary derivatization.

The optical purity is numerically equivalent to the "enantiomeric excess". The term "enantiomeric excess" is defined in percentage (%) value as follows: [mole fraction (major enantiomer) mole fraction (minor enantiomer)]×100. An example of enantiomeric excess of 99% represents a ratio of 99.5% of one enantiomer and 0.5% of the opposite enantiomer.

There is also provided "pharmaceutically acceptable hydrates" of the compounds of the present invention. "Hydrates" exist when the compound of the invention incorporates water. The hydrate may contain one or more molecule of water per molecule of compound of the invention. Illustrative non-limiting examples include monohydrate, dihydrate, trihydrate and tetrahydrate. The hydrate may contain one or more molecule of compound of the invention per molecule of water. An illustrative non-limiting example includes semi-hydrate. In one embodiment, the water may be held in the crystal in various ways and thus, the water molecules may occupy lattice positions in the crystal, or they may form bonds with salts of the compounds as described herein. The hydrate must be "acceptable" in the sense of not being deleterious to the recipient thereof. The hydration may be assessed by methods known in the art such as Loss on Drying techniques (LOD) and Karl Fisher titration.

There is also provided "pharmaceutically acceptable salts" of the compounds of the present invention. By the term "pharmaceutically acceptable salts" of compounds are meant those derived from pharmaceutically acceptable inorganic and organic acids and bases. Examples of suitable acids include but are not limited to hydrochloric, hydrobromic, sulphuric, nitric, perchloric, fumaric, maleic, phosphoric, glycollic, lactic, salicylic, succinic, toleune-p-sulphonic, tartaric, acetic, trifluoroacetic, citric, methanesulphonic, formic, benzoic, malonic, naphthalene-2-sulphonic and benzenesulphonic acids. Other acids such as oxalic, while not in themselves pharmaceutically acceptable, may be useful as intermediates in obtaining the compounds of the invention and their pharmaceutically acceptable acid addition salts.

Salts derived from appropriate bases include alkali metal, alkaline earth metal or ammonium salts. The salt(s) must be "acceptable" in the sense of not being deleterious to the recipient thereof. Non-limiting examples of such salts known by those of ordinary skill in the art include without limitation calcium, potassium, sodium, choline, ethylenediamine, tromethamine, arginine, glycinelycine, lycine, magnesium and meglumine.

There is also provided a "pharmaceutically acceptable solvates" of the compounds of the present invention. The term "solvate" means that the compound of the invention incorporates one or more pharmaceutically acceptable solvent. The solvate may contain one or more molecule of solvent per molecule of compound of the invention or may contain one or more molecule of compound of the invention per molecule of solvent. In one embodiment, the solvent may be held in the crystal in various ways and thus, the solvent molecule may occupy lattice positions in the crystal, or they may form bonds with salts of the compounds as described herein. The solvate(s) must be "acceptable" in the sense of not being deleterious to the recipient thereof. The solvation may be assessed by methods known in the art such as Loss on Drying techniques (LOD).

Reference hereinafter to a compound according to the invention includes compounds of the general formula (I) and their pharmaceutically acceptable salts, hydrates and solvates.

"Polymorphs": It will be appreciated by those skilled in the art that the compounds in accordance with the present invention can exist in several different crystalline forms due to a different arrangement of molecules in the crystal lattice. This may include solvate or hydrate (also known as pseudopolymorphs) and amorphous forms. All such crystalline forms and polymorphs are included within the scope of the invention. The polymorphs may be characterized by methods well known in the art. Examples of analytical procedures that may be used to determine whether polymorphism occurs include: melting point (including hot-stage microscopy), infrared (not in solution), X-ray powder diffraction, thermal analysis methods (e.g. differential scanning calorimetry (DSC), differential thermal analysis (DTA), thermogravimetric analysis (TGA)), Raman spectroscopy, comparative intrinsic dissolution rate, scanning electron microscopy (SEM).

In one aspect, the present invention provides novel compounds including:

Compound 1 3-(RS)-[2-(4-Bromo-benzyl)-1-oxo-2,8-diaza-spiro[4.5]dec-8-ylmethyl]-4-(SR)-phenylpyrrolidine-1-carboxylic acid tert-butyl ester Compound 2 8-(1-Benzoyl-4-(SR)-phenylpyrrolidin-3-(RS)-ylmethyl)-2-(4-bromo-benzyl)-2,8-diaza-spiro[4.5]decan-1-one hydrochloride Compound 3 2-(4-Bromobenzyl)-8-(4-(SR)-phenylpyrrolidin-3-(RS)-ylmethyl)-2,8-diaza-spiro[4.5]decan-1-one Compound 4 3-(RS)-[2-(4-Bromobenzyl)-3-oxo-2,8-diaza-spiro[4.5]dec-8-ylmethyl]-4-(SR)-phenylpyrrolidine-1-carboxylic acid tert-butyl ester Compound 5 2-(4-Bromobenzyl)-8-(4-(SR)-phenyl-1-phenylacetyl-pyrrolidin-3-(RS)-ylmethyl)-2,8-diaza-spiro[4.5]decan-1-one hydrochloride Compound 6 3-(RS)-[2-(4-Methanesulfonylbenzyl)-1-oxo-2,8-diaza-spiro[4.5]dec-8-ylmethyl]-4-(SR)-phenylpyrrolidine-1-carboxylic acid tert-butyl ester Compound 7 3-(RS)-[2-(4-Methoxybenzyl)-1-oxo-2,8-diaza-spiro[4.5]dec-8-ylmethyl]-4-(SR)-phenylpyrrolidine-1-carboxylic acid tert-butyl ester Compound 8 8-(1-Acetyl-4-(SR)-phenylpyrrolidin-3-(RS)-ylmethyl)-2-(4-bromobenzyl)-2,8-diaza-spiro[4.5]decan-1-one hydrochloride Compound 9 2-(4-Bromobenzyl)-8-(1-cyclopropanecarbonyl-4-(SR)-phenylpyrrolidin-3-(RS)-ylmethyl)-2,8-diaza-spiro[4.5]decan-1-one hydrochloride Compound 10 2-(4-Bromobenzyl)-8-(1-isobutyryl-4-(SR)-phenylpyrrolidin-3-(RS)-ylmethyl)-2,8-diaza-spiro[4.5]decan-1-one hydrochloride Compound 11 2-(4-Bromobenzyl)-8-[1-(3-methyl-butyryl)-4-(SR)-phenylpyrrolidin-3-(RS)-ylmethyl]-2,8-diaza-spiro[4.5]decan-1-one hydrochloride Compound 12 2-(4-Bromobenzyl)-8-[1-(2-chloro-benzoyl)-4-(SR)-phenylpyrrolidin-3-(RS)-ylmethyl]-2,8-diaza-spiro[4.5]decan-1-one hydrochloride Compound 13 2-(4-Bromobenzyl)-8-[1-(2-methoxybenzoyl)-4-(SR)-phenylpyrrolidin-3-(RS)-ylmethyl]-2,8-diaza-spiro[4.5]decan-1-one hydrochloride Compound 14 2-(4-Bromobenzyl)-8-[4-(SR)-phenyl-1-(pyridine-2-carbonyl)-pyrrolidin-3-(RS)-ylmethyl]-2,8-diaza-spiro[4.5]decan-1-one dihydrochloride Compound 15 2-(4-Bromobenzyl)-8-[1-(3-chlorobenzoyl)-4-(SR)-phenylpyrrolidin-3-(RS)-ylmethyl]-2,8-diaza-spiro[4.5]decan-1-one hydrochloride Compound 16 2-(4-Bromobenzyl)-8-[1-(3-methoxybenzoyl)-4-(SR)-phenylpyrrolidin-3-(RS)-ylmethyl]-2,8-diaza-spiro[4.5]decan-1-one hydrochloride Compound 17 2-(4-Bromobenzyl)-8-[4-(SR)-phenyl-1-(pyridine-3-carbonyl)-pyrrolidin-3-(RS)-ylmethyl]-2,8-diaza-spiro[4.5]decan-1-one dihydrochloride Compound 18 2-(4-Bromobenzyl)-8-[1-(4-chlorobenzoyl)-4-(SR)-phenyl-pyrrolidin-3-(RS)-ylmethyl]-2,8-diaza-spiro[4.5]decan-1-one hydrochloride Compound 19 2-(4-Bromobenzyl)-8-[1-(4-methoxybenzoyl)-4-(SR)-phenylpyrrolidin-3-(RS)-ylmethyl]-2,8-diaza-spiro[4.5]decan-1-one hydrochloride Compound 20 2-(4-Bromobenzyl)-8-[4-(SR)-phenyl-1-(pyridine-4-carbonyl)-pyrrolidin-3-(RS)-ylmethyl]-2,8-diaza-spiro[4.5]decan-1-one dihydrochloride Compound 21 2-(4-Bromobenzyl)-8-[1-(3,4-dichlorobenzoyl)-4-(SR)-phenylpyrrolidin-3-(RS)-ylmethyl]-2,8-diaza-spiro[4.5]decan-1-one hydrochloride Compound 22 2-(4-Bromobenzyl)-8-[1-(3,4-dimethoxybenzoyl)-4-(SR)-phenylpyrrolidin-3-(RS)-ylmethyl]-2,8-diaza-spiro[4.5]decan-1-one hydrochloride Compound 23 2-(4-Bromobenzyl)-8-{1-[2-(2-chlorophenyl)-acetyl]-4-(SR)-phenylpyrrolidin-3-(RS)-ylmethyl}-2,8-diaza-spiro[4.5]decan-1-one hydrochloride Compound 24 2-(4-Bromobenzyl)-8-{1-[2-(2-methoxyphenyl)-acetyl]-4-(SR)-phenylpyrrolidin-3-(RS)-ylmethyl}-2,8-diaza-spiro[4.5]decan-1-one hydrochloride Compound 25 2-(4-Bromobenzyl)-8-{1-[2-(3-chlorophenyl)-acetyl]-4-(SR)-phenylpyrrolidin-3-(RS)-ylmethyl}-2,8-diaza-spiro[4.5]decan-1-one hydrochloride Compound 26 2-(4-Bromo-benzyl)-8-{1-[2-(3-methoxyphenyl)-acetyl]-4-(SR)-phenyl-pyrrolidin-3-(RS)-ylmethyl}-2,8-diaza-spiro[4.5]decan-1-one hydrochloride Compound 27 2-(4-Bromobenzyl)-8-[4-(SR)-phenyl-1-(2-pyridin-3-yl-acetyl)-pyrrolidin-3-(RS)-ylmethyl]-2,8-diaza-spiro[4.5]decan-1-one dihydrochloride Compound 28 2-(4-Bromobenzyl)-8-{1-[2-(4-methoxyphenyl)-acetyl]-4-(SR)-phenylpyrrolidin-3-(RS)-ylmethyl}-2,8-diaza-spiro[4.5]decan-1-one hydrochloride Compound 29 2-(4-Bromobenzyl)-8-{1-[2-(3,4-dichlorophenyl)-acetyl]-4-(SR)-phenylpyrrolidin-3-(RS)-ylmethyl}-2,8-diaza-spiro[4.5]decan-1-one hydrochloride Compound 30 2-(4-Bromobenzyl)-8-[4-(SR)-phenyl-1-(tetrahydro-pyran-4-carbonyl)-pyrrolidin-3-(RS)-ylmethyl]-2,8-diaza-spiro[4.5]decan-1-one hydrochloride Compound 31 2-(4-Bromobenzyl)-8-(1-cyclopentanecarbonyl-4-(SR)-phenyl-pyrrolidin-3-(RS)-ylmethyl)-2,8-diaza-spiro[4.5]decan-1-one hydrochloride Compound 32 2-(4-Bromobenzyl)-8-(1-cyclobutanecarbonyl-4-(SR)-phenyl-pyrrolidin-3-(RS)-ylmethyl)-2,8-diaza-spiro[4.5]decan-1-one hydrochloride Compound 33 2-(4-Bromobenzyl)-8-(1-cycloheptanecarbonyl-4-(SR)-phenyl-pyrrolidin-3-(RS)-ylmethyl)-2,8-diaza-spiro[4.5]decan-1-one hydrochloride Compound 34 2-(4-Bromobenzyl)-8-[1-(2-cyclohexyl-acetyl)-4-(SR)-phenylpyrrolidin-3-(RS)-ylmethyl]-2,8-diaza-spiro[4.5]decan-1-one hydrochloride Compound 35 2-(4-Bromobenzyl)-8-[1-(2-cyclopentyl-acetyl)-4-(SR)-phenylpyrrolidin-3-(RS)-ylmethyl]-2,8-diaza-spiro[4.5]decan-1-one hydrochloride Compound 36 2-(4-Bromobenzyl)-8-[1-(furan-2-carbonyl)-4-(SR)-phenylpyrrolidin-3-(RS)-ylmethyl]-2,8-diaza-spiro[4.5]decan-1-one hydrochloride Compound 37 2-(4-Bromobenzyl)-8-[1-(2-ethyl-butyryl)-4-(SR)-phenylpyrrolidin-3-(RS)-ylmethyl]-2,8-diaza-spiro[4.5]decan-1-one hydrochloride Compound 38 2-(4-Bromobenzyl)-8-[4-(SR)-phenyl-1-(thiophene-2-carbonyl)-pyrrolidin-3-(RS)-ylmethyl]-2,8-diaza-spiro[4.5]decan-1-one hydrochloride Compound 39 2-(4-Bromobenzyl)-8-{1-[2-(3,4-dimethoxyphenyl)-acetyl]-4-(SR)-phenylpyrrolidin-3-(RS)-ylmethyl}-2,8-diaza-spiro[4.5]decan-1-one hydrochloride Compound 40 2-(4-Bromobenzyl)-8-(1-cyclohexanecarbonyl-4-(SR)-phenylpyrrolidin-3-(RS)-ylmethyl)-2,8-diaza-spiro[4.5]decan-1-one hydrochloride Compound 41 2-(4-Bromobenzyl)-8-[4-(SR)-phenyl-1-(3-phenyl-propionyl)-pyrrolidin-3-(RS)-ylmethyl]-2,8-diaza-spiro[4.5]decan-1-one hydrochloride Compound 42 2-(4-Methoxybenzyl)-8-(4-(SR)-phenylpyrrolidin-3-(RS)-ylmethyl)-2,8-diaza-spiro[4.5]decan-1-one Compound 43 2-(4-Methanesulfonylbenzyl)-8-(4-(SR)-phenylpyrrolidin-3-(RS)-ylmethyl)-2,8-diaza-spiro[4.5]decan-1-one Compound 44 2-(4-Bromobenzyl)-8-[1-(2-cyclopropyl-acetyl)-4-(SR)-phenylpyrrolidin-3-(RS)-ylmethyl]-2,8-diaza-spiro[4.5]decan-1-one hydrochloride Compound 45 8-(1-Acetyl-4-(SR)-phenylpyrrolidin-3-(RS)-ylmethyl)-2-(4-methoxybenzyl)-2,8-diaza-spiro[4.5]decan-1-one hydrochloride Compound 46 2-(4-Methoxybenzyl)-8-(4-(SR)-phenyl-1-propionyl-pyrrolidin-3-(RS)-ylmethyl)-2,8-diaza-spiro[4.5]decan-1-one hydrochloride Compound 47 8-[1-(2-Methoxy-acetyl)-4-(SR)-phenylpyrrolidin-3-(RS)-ylmethyl]-2-(4-methoxybenzyl)-2,8-diaza-spiro[4.5]decan-1-one hydrochloride Compound 48 2-(4-Methoxybenzyl)-8-[1-(3-methoxypropionyl)-4-(SR)-phenylpyrrolidin-3-(RS)-ylmethyl]-2,8-diaza-spiro[4.5]decan-1-one hydrochloride Compound 49 8-(1-Cyclopropanecarbonyl-4-(SR)-phenylpyrrolidin-3-(RS)-ylmethyl)-2-(4-methoxy-benzyl)-2,8-diaza-spiro[4.5]decan-1-one hydrochloride Compound 50 8-(1-Cyclobutanecarbonyl-4-(SR)-phenylpyrrolidin-3-(RS)-ylmethyl)-2-(4-methoxybenzyl)-2,8-diaza-spiro[4.5]decan-1-one hydrochloride Compound 51 8-(1-Cyclopentanecarbonyl-4-(SR)-phenylpyrrolidin-3-(RS)-ylmethyl)-2-(4-methoxybenzyl)-2,8-diaza-spiro[4.5]decan-1-one hydrochloride Compound 52 8-(1-Cyclohexanecarbonyl-4-(SR)-phenylpyrrolidin-3-(RS)-ylmethyl)-2-(4-methoxybenzyl)-2,8-diaza-spiro[4.5]decan-1-one hydrochloride Compound 53 8-(1-Cycloheptanecarbonyl-4-(SR)-phenylpyrrolidin-3-(RS)-ylmethyl)-2-(4-methoxybenzyl)-2,8-diaza-spiro[4.5]decan-1-one hydrochloride Compound 54 2-(4-Methoxybenzyl)-8-[4-(SR)-phenyl-1-(tetrahydro-pyran-4-carbonyl)-pyrrolidin-3-(RS)-ylmethyl]-2,8-diaza-spiro[4.5]decan-1-one hydrochloride Compound 55 8-[1-(2-Cyclopropyl-acetyl)-4-(SR)-phenylpyrrolidin-3-(RS)-ylmethyl]-2-(4-methoxybenzyl)-2,8-diaza-spiro[4.5]decan-1-one hydrochloride Compound 56 8-[1-(2-Cyclopentyl-acetyl)-4-(SR)-phenylpyrrolidin-3-(RS)-ylmethyl]-2-(4-methoxybenzyl)-2,8-diaza-spiro[4.5]decan-1-one hydrochloride Compound 57 8-[1-(2-Cyclohexyl-acetyl)-4-(SR)-phenylpyrrolidin-3-(RS)-ylmethyl]-2-(4-methoxybenzyl)-2,8-diaza-spiro[4.5]decan-1-one hydrochloride Compound 58 8-(1-Isobutyryl-4-(SR)-phenylpyrrolidin-3-(RS)-ylmethyl)-2-(4-methoxybenzyl)-2,8-diaza-spiro[4.5]decan-1-one hydrochloride Compound 59 2-(4-Methoxybenzyl)-8-[1-(3-methyl-butyryl)-4-(SR)-phenylpyrrolidin-3-(RS)-ylmethyl]-2,8-diaza-spiro[4.5]decan-1-one hydrochloride Compound 60 8-[1-(2-Ethyl-butyryl)-4-(SR)-phenylpyrrolidin-3-(RS)-ylmethyl]-2-(4-methoxybenzyl)-2,8-diaza-spiro[4.5]decan-1-one hydrochloride Compound 61 8-[1-(2-Chlorobenzoyl)-4-(SR)-phenylpyrrolidin-3-(RS)-ylmethyl]-2-(4-methoxybenzyl)-2,8-diaza-spiro[4.5]decan-1-one hydrochloride Compound 62 8-[1-(2,6-Dichlorobenzoyl)-4-(SR)-phenylpyrrolidin-3-(RS)-ylmethyl]-2-(4-methoxybenzyl)-2,8-diaza-spiro[4.5]decan-1-one hydrochloride Compound 63 8-[1-(2-Methoxybenzoyl)-4-(SR)-phenylpyrrolidin-3-(RS)-ylmethyl]-2-(4-methoxybenzyl)-2,8-diaza-spiro[4.5]decan-1-one hydrochloride Compound 64 2-(4-Methoxybenzyl)-8-[4-(SR)-phenyl-1-(pyridine-2-carbonyl)-pyrrolidin-3-(RS)-ylmethyl]-2,8-diaza-spiro[4.5]decan-1-one dihydrochloride Compound 65 8-[1-(2-Fluorobenzoyl)-4-(SR)-phenylpyrrolidin-3-(RS)-ylmethyl]-2-(4-methoxybenzyl)-2,8-diaza-spiro[4.5]decan-1-one hydrochloride Compound 66 2-(4-Methoxybenzyl)-8-[1-(2-methylbenzoyl)-4-(SR)-phenylpyrrolidin-3-(RS)-ylmethyl]-2,8-diaza-spiro[4.5]decan-1-one hydrochloride Compound 67 2-(4-Methoxybenzyl)-8-[4-(SR)-phenyl-1-(pyridine-3-carbonyl)-pyrrolidin-3-(RS)-ylmethyl]-2,8-diaza-spiro[4.5]decan-1-one dihydrochloride Compound 68 2-(4-Methoxybenzyl)-8-[4-(SR)-phenyl-1-(pyridine-4-carbonyl)-pyrrolidin-3-(RS)-ylmethyl]-2,8-diaza-spiro[4.5]decan-1-one dihydrochloride Compound 69 8-[1-(Furan-2-carbonyl)-4-(SR)-phenylpyrrolidin-3-(RS)-ylmethyl]-2-(4-methoxybenzyl)-2,8-diaza-spiro[4.5]decan-1-one hydrochloride Compound 70 2-(4-Methoxybenzyl)-8-[4-(SR)-phenyl-1-(thiophene-2-carbonyl)-pyrrolidin-3-(RS)-ylmethyl]-2,8-diaza-spiro[4.5]decan-1-one hydrochloride Compound 71 8-(1-Acetyl-4-(SR)-phenylpyrrolidin-3-(RS)-ylmethyl)-2-(4-methanesulfonylbenzyl)-2,8-diaza-spiro[4.5]decan-1-one hydrochloride Compound 72 2-(4-Methanesulfonylbenzyl)-8-(4-(SR)-phenyl-1-propionyl-pyrrolidin-3-(RS)-ylmethyl)-2,8-diaza-spiro[4.5]decan-1-one hydrochloride Compound 73 2-(4-Methanesulfonylbenzyl)-8-[1-(2-methoxy-acetyl)-4-(SR)-phenylpyrrolidin-3-(RS)-ylmethyl]-2,8-diaza-spiro[4.5]decan-1-one hydrochloride Compound 74 2-(4-Methanesulfonylbenzyl)-8-[1-(3-methoxy-propionyl)-4-(SR)-phenylpyrrolidin-3-(RS)-ylmethyl]-2,8-diaza-spiro[4.5]decan-1-one hydrochloride Compound 75 8-(1-Cyclopropanecarbonyl-4-(SR)-phenylpyrrolidin-3-(RS)-ylmethyl)-2-(4-methanesulfonylbenzyl)-2,8-diaza-spiro[45]decan-1-one hydrochloride Compound 76 8-(1-Cyclobutanecarbonyl-4-(SR)-phenylpyrrolidin-3-(RS)-ylmethyl)-2-(4-methanesulfonylbenzyl)-2,8-diaza-spiro[4.5]decan-1-one hydrochloride Compound 77 8-(1-Cyclopentanecarbonyl-4-(SR)-phenylpyrrolidin-3-(RS)-ylmethyl)-2-(4-methanesulfonylbenzyl)-2,8-diaza-spiro[4.5]decan-1-one hydrochloride Compound 78 8-(1-Cyclohexanecarbonyl-4-(SR)-phenylpyrrolidin-3-(RS)-ylmethyl)-2-(4-methanesulfonylbenzyl)-2,8-diaza-spiro[4.5]decan-1-one hydrochloride Compound 79 8-(1-Cycloheptanecarbonyl-4-(SR)-phenylpyrrolidin-3-(RS)-ylmethyl)-2-(4-methanesulfonylbenzyl)-2,8-diaza-spiro[4.5]decan-1-one hydrochloride Compound 80 8-[1-(2-Cyclopropyl-acetyl)-4-(SR)-phenylpyrrolidin-3-(RS)-ylmethyl]-2-(4-methanesulfonylbenzyl)-2,8-diaza-spiro[4.5]decan-1-one hydrochloride Compound 81 8-[1-(2-Cyclopentyl-acetyl)-4-(SR)-phenylpyrrolidin-3-(RS)-ylmethyl]-2-(4-methanesulfonylbenzyl)-2,8-diaza-spiro[4.5]decan-1-one hydrochloride Compound 82 8-[1-(2-Cyclohexyl-acetyl)-4-(SR)-phenylpyrrolidin-3-(RS)-ylmethyl]-2-(4-methanesulfonylbenzyl)-2,8-diaza-spiro[4.5]decan-1-one hydrochloride Compound 83 8-(1-Isobutyryl-4-(SR)-phenylpyrrolidin-3-(RS)-ylmethyl)-2-(4-methanesulfonylbenzyl)-2,8-diaza-spiro[4.5]decan-1-one hydrochloride Compound 84 2-(4-Methanesulfonylbenzyl)-8-[1-(3-methyl-butyryl)-4-(SR)-phenylpyrrolidin-3-(RS)-ylmethyl]-2,8-diaza-spiro[4.5]decan-1-one hydrochloride Compound 85 8-[1-(2-Ethyl-butyryl)-4-(SR)-phenylpyrrolidin-3-(RS)-ylmethyl]-2-(4-methanesulfonylbenzyl)-2,8-diaza-spiro[4.5]decan-1-one hydrochloride Compound 86 8-[1-(2-Chlorobenzoyl)-4-(SR)-phenylpyrrolidin-3-(RS)-ylmethyl]-2-(4-methanesulfonylbenzyl)-2,8-diaza-spiro[4.5]decan-1-one hydrochloride Compound 87 8-[1-(2,6-Dichlorobenzoyl)-4-(SR)-phenylpyrrolidin-3-(RS)-ylmethyl]-2-(4-methanesulfonylbenzyl)-2,8-diaza-spiro[4.5]decan-1-one hydrochloride Compound 88 2-(4-Methanesulfonylbenzyl)-8-[1-(2-methoxybenzoyl)-4-(SR)-phenylpyrrolidin-3-(RS)-ylmethyl]-2,8-diaza-spiro[4.5]decan-1-one hydrochloride Compound 89 2-(4-Methanesulfonylbenzyl)-8-[4-(SR)-phenyl-1-(pyridine-2-carbonyl)-pyrrolidin-3-(RS)-ylmethyl]-2,8-diaza-spiro[4.5]decan-1-one dihydrochloride Compound 90 8-[1-(2-Fluorobenzoyl)-4-(SR)-phenylpyrrolidin-3-(RS)-ylmethyl]-2-(4-methanesulfonylbenzyl)-2,8-diaza-spiro[4.5]decan-1-one hydrochloride Compound 91 2-(4-Methanesulfonylbenzyl)-8-[1-(2-methylbenzoyl)-4-(SR)-phenylpyrrolidin-3-(RS)-ylmethyl]-2,8-diaza-spiro[4.5]decan-1-one hydrochloride Compound 92 2-(4-Methanesulfonylbenzyl)-8-[4-(SR)-phenyl-1-(pyridine-3-carbonyl)-pyrrolidin-3-(RS)-ylmethyl]-2,8-diaza-spiro[4.5]decan-1-one dihydrochloride Compound 93 2-(4-Methanesulfonylbenzyl)-8-[4-(SR)-phenyl-1-(pyridine-4-carbonyl)-pyrrolidin-3-(RS)-ylmethyl]-2,8-diaza-spiro[4.5]decan-1-one dihydrochloride Compound 94 8-[1-(Furan-2-carbonyl)-4-(SR)-phenylpyrrolidin-3-(RS)-ylmethyl]-2-(4-methanesulfonylbenzyl)-2,8-diaza-spiro[4.5]decan-1-one hydrochloride Compound 95 2-(4-Methanesulfonylbenzyl)-8-[4-(SR)-phenyl-1-(thiophene-2-carbonyl)-pyrrolidin-3-(RS)-ylmethyl]-2,8-diaza-spiro[4.5]decan-1-one hydrochloride Compound 96 8-(1-Benzenesulfonyl-4-(SR)-phenylpyrrolidin-3-((RS)-ylmethyl)-2-(4-bromobenzyl)-2,8-diazaspiro[4.5]decan-1-one hydrochloride Compound 97 3-((RS)-[2-(4-Bromobenzyl)-1-oxo-2,8-diaza-spiro[4.5]dec-8-ylmethyl]-4-(SR)-phenyl-pyrrolidine-1-carboxylic acid phenylamide hydrochloride Compound 98 8-(1-Benzyl-4-(SR)-phenylpyrrolidin-3-((RS)-ylmethyl)-2-(4-bromobenzyl)-2,8-diaza-spiro[4.5]decan-1-one dihydrochloride Compound 99 2-(4-Bromobenzyl)-8-(1-cyclohexylmethyl-4-(SR)-phenylpyrrolidin-3-((RS)-ylmethyl)-2,8-diazaspiro[4.5]decan-1-one dihydrochloride Compound 100 (3S,4S)-3-[2-(4-Bromo-benzyl)-1-oxo-2,8-diaza-spiro[4.5]dec-8-ylmethyl]-4-phenyl-pyrrolidine-1-carboxylic acid tert-butyl ester Compound 101 2-(4-Bromo-benzyl)-8-((3R,4S)-4-phenylpyrrolidin-3-ylmethyl)-2,8-diaza-spiro[4.5]decan-1-one Compound 102 8-((3S,4S)-1-Acetyl-4-phenyl-pyrrolidin-3-ylmethyl)-2-(4-bromo-benzyl)-2,8-diaza-spiro[4.5]decan-1-one hydrochloride Compound 103 2-(4-Bromo-benzyl)-8-((3S,4S)-1-cyclopropanecarbonyl-4-phenyl-pyrrolidin-3-ylmethyl)-2,8-diaza-spiro[4.5]decan-1-one hydrochloride Compound 104 2-(4-Bromo-benzyl)-8-[(3S,4S)-1-(2-cyclopropyl-acetyl)-4-phenyl-pyrrolidin-3-ylmethyl]-2,8-diaza-spiro[4.5]decan-1-one hydrochloride Compound 105 2-(4-Bromo-benzyl)-8-[(3S,4S)-4-phenyl-1-(tetrahydro-pyran-4-carbonyl)-pyrrolidin-3-ylmethyl]-2,8-diaza-spiro[4.5]decan-1-one hydrochloride Compound 106 2-(4-Bromo-benzyl)-8-[(3S,4S)-1-(2-chloro-benzoyl)-4-phenyl-pyrrolidin-3-ylmethyl]-2,8-diaza-spiro[4.5]decan-1-one hydrochloride Compound 107 2-(4-Bromo-benzyl)-8-[(3S,4S)-1-(2-methoxy-benzoyl)-4-phenyl-pyrrolidin-3-ylmethyl]-2,8-diaza-spiro[4.5]decan-1-one hydrochloride Compound 108 2-(4-Bromo-benzyl)-8-[(3S,4S)-4-phenyl-1-(pyridine-3-carbonyl)-pyrrolidin-3-ylmethyl]-2,8-diaza-spiro[4.5]decan-1-one dihydrochloride Compound 109 2-(4-Bromo-benzyl)-8-{(3S,4S)-1-[2-(3,4-dichloro-phenyl)-acetyl]-4-phenyl-pyrrolidin-3-ylmethyl}-2,8-diaza-spiro[4.5]decan-1-one hydrochloride Compound 110 (3S,4S)-3-[2-(4-Methoxy-benzyl)-1-oxo-2,8-diaza-spiro[4.5]dec-8-ylmethyl]-4-phenyl-pyrrolidine-1-carboxylic acid tert-butyl ester Compound 111 2-(4-Methoxy-benzyl)-8-((3R,4S)-4-phenyl-pyrrolidin-3-ylmethyl)-2,8-diaza-spiro[4.5]decan-1-one Compound 112 8-((3S,4S)-1-Acetyl-4-phenyl-pyrrolidin-3-ylmethyl)-2-(4-methoxy-benzyl)-2,8-diaza-spiro[4.5]decan-1-one hydrochloride Compound 113 2-(4-Methoxy-benzyl)-8-((3S,4S)-4-phenyl-1-propionyl-pyrrolidin-3-ylmethyl)-2,8-diaza-spiro[4.5]decan-1-one hydrochloride Compound 114 8-[(3S,4S)-1-(2-Methoxy-acetyl)-4-phenyl-pyrrolidin-3-ylmethyl]-2-(4-methoxy-benzyl)-2,8-diaza-spiro[4.5]decan-1-one hydrochloride Compound 115 8-((3S,4S)-1-Isobutyryl-4-phenyl-pyrrolidin-3-ylmethyl)-2-(4-methoxy-benzyl)-2,8-diaza-spiro[4.5]decan-1-one hydrochloride Compound 116 8-((3S,4S)-1-Cyclopropanecarbonyl-4-phenyl-pyrrolidin-3-ylmethyl)-2-(4-methoxy-benzyl)-2,8-diaza-spiro[4.5]decan-1-one hydrochloride Compound 117 8-[(3S,4S)-1-(2-Cyclopropyl-acetyl)-4-phenyl-pyrrolidin-3-ylmethyl]-2-(4-methoxy-benzyl)-2,8-diaza-spiro[4.5]decan-1-one hydrochloride Compound 118 2-(4-Methoxy-benzyl)-8-[(3S,4S)-4-phenyl-1-(tetrahydro-pyran-4-carbonyl)-pyrrolidin-3-ylmethyl]-2,8-diaza-spiro[4.5]decan-1-one hydrochloride Compound 119 8-[(3S,4S)-1-(4,4-Difluoro-cyclohexanecarbonyl)-4-phenyl-pyrrolidin-3-ylmethyl]-2-(4-methoxy-benzyl)-2,8-diaza-spiro[4.5]decan-1-one hydrochloride Compound 120 8-[(3S,4S)-1-(2-Chloro-benzoyl)-4-phenyl-pyrrolidin-3-ylmethyl]-2-(4-methoxy-benzyl)-2,8-diaza-spiro[4.5]decan-1-one hydrochloride Compound 121 8-[(3S,4S)-1-(2-Fluoro-benzoyl)-4-phenyl-pyrrolidin-3-ylmethyl]-2-(4-methoxy-benzyl)-2,8-diaza-spiro[4.5]decan-1-one hydrochloride Compound 122 2-(4-Methoxy-benzyl)-8-[(3S,4S)-4-phenyl-1-(pyrimidine-5-carbonyl)-pyrrolidin-3-ylmethyl]-2,8-diaza-spiro[4.5]decan-1-one trihydrochloride Compound 123 8-[(3S,4S)-1-(4,6-Dimethyl-pyrimidine-5-carbonyl)-4-phenyl-pyrrolidin-3-ylmethyl]-2-(4-methoxy-benzyl)-2,8-diaza-spiro[4.5]decan-1-one trihydrochloride Compound 124 (3S,4S)-3-[2-(4-Methanesulfonyl-benzyl)-1-oxo-2,8-diaza-spiro[4.5]dec-8-ylmethyl]-4-phenyl-pyrrolidine-1-carboxylic acid tert-butyl ester Compound 125 2-(4-Methanesulfonyl-benzyl)-8-((3R,4S)-4-phenyl-pyrrolidin-3-ylmethyl)-2,8-diaza-spiro[4.5]decan-1-one Compound 126 8-((3S,4S)-1-Acetyl-4-phenyl-pyrrolidin-3-ylmethyl)-2-(4-methanesulfonyl-benzyl)-2,8-diaza-spiro[4.5]decan-1-one hydrochloride Compound 127 2-(4-Methanesulfonyl-benzyl)-8-((3S,4S)-4-phenyl-1-propionyl-pyrrolidin-3-ylmethyl)-2,8-diaza-spiro[4.5]decan-1-one hydrochloride Compound 128 8-((3S,4S)-1-Isobutyryl-4-phenyl-pyrrolidin-3-ylmethyl)-2-(4-methanesulfonyl-benzyl)-2,8-diaza-spiro[4.5]decan-1-one hydrochloride Compound 129 8-((3S,4S)-1-Cyclopentanecarbonyl-4-phenyl-pyrrolidin-3-ylmethyl)-2-(4-methanesulfonyl-benzyl)-2,8-diaza-spiro[4.5]decan-1-one hydrochloride Compound 130 8-((3S,4S)-1-Cyclopropanecarbonyl-4-phenyl-pyrrolidin-3-ylmethyl)-2-(4-methanesulfonyl-benzyl)-2,8-diaza-spiro[4.5]decan-1-one hydrochloride Compound 131 8-[(3S,4S)-1-(2-Cyclopropyl-acetyl)-4-phenyl-pyrrolidin-3-ylmethyl]-2-(4-methanesulfonyl-benzyl)-2,8-diaza-spiro[4.5]decan-1-one hydrochloride Compound 132 8-[(3S,4S)-1-(4,4-Difluoro-cyclohexanecarbonyl)-4-phenyl-pyrrolidin-3-ylmethyl]-2-(4-methanesulfonyl-benzyl)-2,8-diaza-spiro[4.5]decan-1-one hydrochloride Compound 133 2-(4-Methanesulfonyl-benzyl)-8-[(3S,4S)-4-phenyl-1-(pyridine-3-carbonyl)-pyrrolidin-3-ylmethyl]-2,8-diaza-spiro[4.5]decan-1-one dihydrochloride Compound 134 2-(4-Methanesulfonyl-benzyl)-8-[(3S,4S)-4-phenyl-1-(pyrimidine-5-carbonyl)-pyrrolidin-3-ylmethyl]-2,8-diaza-spiro[4.5]decan-1-one trihydrochloride Compound 135 8-[(3S,4S)-1-(4,6-Dimethyl-pyrimidine-5-carbonyl)-4-phenyl-pyrrolidin-3-ylmethyl]-2-(4-methanesulfonyl-benzyl)-2,8-diaza-spiro[4.5]decan-1-one trihydrochloride Compound 136 8-[(3S,4S)-1-(2-Chloro-benzoyl)-4-phenyl-pyrrolidin-3-ylmethyl]-2-(4-methanesulfonyl-benzyl)-2,8-diaza-spiro[4.5]decan-1-one hydrochloride Compound 137 8-[(3S,4S)-1-(2-Fluoro-benzoyl)-4-phenyl-pyrrolidin-3-ylmethyl]-2-(4-methanesulfonyl-benzyl)-2,8-diaza-spiro[4.5]decan-1-one hydrochloride Compound 138 (3S,4S)-3-[2-(4-Methoxy-benzyl)-3-oxo-2,8-diaza-spiro[4.5]dec-8-ylmethyl]-4-phenyl-pyrrolidine-1-carboxylic acid tert-butyl ester Compound 139 2-(4-Methoxy-benzyl)-8-((3R,4S)-4-phenyl-pyrrolidin-3-ylmethyl)-2,8-diaza-spiro[4.5]decan-3-one Compound 140 8-((3S,4S)-1-Isobutyryl-4-phenyl-pyrrolidin-3-ylmethyl)-2-(4-methoxy-benzyl)-2,8-diaza-spiro[4.5]decan-3-one hydrochloride Compound 141 8-((3S,4S)-1-Cyclopropanecarbonyl-4-phenyl-pyrrolidin-3-ylmethyl)-2-(4-methoxy-benzyl)-2,8-diaza-spiro[4.5]decan-3-one hydrochloride Compound 142 8-[(3S,4S)-1-(2-Cyclopropyl-acetyl)-4-phenyl-pyrrolidin-3-ylmethyl]-2-(4-methoxy-benzyl)-2,8-diaza-spiro[4.5]decan-3-one hydrochloride Compound 143 (3S,4S)-3-[2-(4-Methanesulfonyl-benzyl)-3-oxo-2,8-diaza-spiro[4.5]dec-8-ylmethyl]-4-phenyl-pyrrolidine-1-carboxylic acid tert-butyl ester Compound 144 2-(4-Methanesulfonyl-benzyl)-8-((3R,4S)-4-phenyl-pyrrolidin-3-ylmethyl)-2,8-diaza-spiro[4.5]decan-3-one Compound 145 8-((3S,4S)-1-Isobutyryl-4-phenyl-pyrrolidin-3-ylmethyl)-2-(4-methanesulfonyl-benzyl)-2,8-diaza-spiro[4.5]decan-3-one hydrochloride Compound 146 8-((3S,4S)-1-Cyclopropanecarbonyl-4-phenyl-pyrrolidin-3-ylmethyl)-2-(4-methanesulfonyl-benzyl)-2,8-diaza-spiro[4.5]decan-3-one hydrochloride Compound 147 8-[(3S,4S)-1-(2-Cyclopropyl-acetyl)-4-phenyl-pyrrolidin-3-ylmethyl]-2-(4-methanesulfonyl-benzyl)-2,8-diaza-spiro[4.5]decan-3-one hydrochloride Compound 148 2-(4-Bromo-benzyl)-8-((3S,4S)-4-phenyl-1-propionyl-pyrrolidin-3-ylmethyl)-2,8-diaza-spiro[4.5]decan-1-one hydrochloride Compound 149 2-(4-Methanesulfonyl-benzyl)-8-[(3S,4S)-4-phenyl-1-(tetrahydro-pyran-4-carbonyl)-pyrrolidin-3-ylmethyl]-2,8-diaza-spiro[4.5]decan-1-one hydrochloride Compound 150 8-((3S,4S)-1-Ethanesulfonyl-4-phenyl-pyrrolidin-3-ylmethyl)-2-(4-methoxy-benzyl)-2,8-diaza-spiro[4.5]decan-1-one hydrochloride Compound 151 2-(4-Methoxy-benzyl)-8-[(3S,4S)-4-phenyl-1-(propane-2-sulfonyl)-pyrrolidin-3-ylmethyl]-2,8-diaza-spiro[4.5]decan-1-one hydrochloride Compound 152 8-((3S,4S)-1-Cyclopropanesulfonyl-4-phenyl-pyrrolidin-3-ylmethyl)-2-(4-methoxy-benzyl)-2,8-diaza-spiro[4.5]decan-1-one hydrochloride Compound 153 8-((3S,4S)-1-Ethanesulfonyl-4-phenyl-pyrrolidin-3-ylmethyl)-2-(4-methanesulfonyl-benzyl)-2,8-diaza-spiro[4.5]decan-1-one hydrochloride Compound 154 2-(4-Methanesulfonyl-benzyl)-8-[(3S,4S)-4-phenyl-1-(propane-2-sulfonyl)-pyrrolidin-3-ylmethyl]-2,8-diaza-spiro[4.5]decan-1-one hydrochloride Compound 155 8-((3S,4S)-1-Cyclopropanesulfonyl-4-phenyl-pyrrolidin-3-ylmethyl)-2-(4-methanesulfonyl-benzyl)-2,8-diaza-spiro[4.5]decan-1-one hydrochloride Compound 156 8-((3S,4S)-1-Cyclopentanesulfonyl-4-phenyl-pyrrolidin-3-ylmethyl)-2-(4-methanesulfonyl-benzyl)-2,8-diaza-spiro[4.5]decan-1-one hydrochloride Compound 157 2-(4-Methoxy-benzyl)-8-[(3S,4S)-1-(morpholine-4-carbonyl)-4-phenyl-pyrrolidin-3-ylmethyl]-2,8-diaza-spiro[4.5]decan-1-one hydrochloride Compound 158 (3S,4S)-3-[2-(4-Methoxy-benzyl)-1-oxo-2,8-diaza-spiro[4.5]dec-8-ylmethyl]-4-phenyl-pyrrolidine-1-carboxylic acid dimethylamide hydrochloride Compound 159 2-(4-Methoxy-benzyl)-8-[(3S,4S)-4-phenyl-1-(pyrrolidine-1-carbonyl)-pyrrolidin-3-ylmethyl]-2,8-diaza-spiro[4.5]decan-1-one hydrochloride Compound 160 8-[(3S,4S)-1-(3,3-Difluoro-pyrrolidine-1-carbonyl)-4-phenyl-pyrrolidin-3-ylmethyl]-2-(4-methoxy-benzyl)-2,8-diaza-spiro[4.5]decan-1-one hydrochloride Compound 161 (3S,4S)-3-[2-(4-Methoxy-benzyl)-1-oxo-2,8-diaza-spiro[4.5]dec-8-ylmethyl]-4-phenyl-pyrrolidine-1-carboxylic acid cyclopropylamide hydrochloride Compound 162 (3S,4S)-3-[2-(4-Methoxy-benzyl)-1-oxo-2,8-diaza-spiro[4.5]dec-8-ylmethyl]-4-phenyl-pyrrolidine-1-carboxylic acid cyclopentylamide hydrochloride Compound 163 2-(4-Methanesulfonyl-benzyl)-8-[(3S,4S)-1-(morpholine-4-carbonyl)-4-phenyl-pyrrolidin-3-ylmethyl]-2,8-diaza-spiro[4.5]decan-1-one hydrochloride Compound 164 (3S,4S)-3-[2-(4-Methanesulfonyl-benzyl)-1-oxo-2,8-diaza-spiro[4.5]dec-8-ylmethyl]-4-phenyl-pyrrolidine-1-carboxylic acid dimethylamide hydrochloride Compound 165 2-(4-Methanesulfonyl-benzyl)-8-[(3S,4S)-4-phenyl-1-(pyrrolidine-1-carbonyl)-pyrrolidin-3-ylmethyl]-2,8-diaza-spiro[4.5]decan-1-one hydrochloride Compound 166 8-[(3S,4S)-1-(3,3-Difluoro-pyrrolidine-1-carbonyl)-4-phenyl-pyrrolidin-3-ylmethyl]-2-(4-methanesulfonyl-benzyl)-2,8-diaza-spiro[4.5]decan-1-one hydrochloride Compound 167 (3S,4S)-3-[2-(4-Methanesulfonyl-benzyl)-1-oxo-2,8-diaza-spiro[4.5]dec-8-ylmethyl]-4-phenyl-pyrrolidine-1-carboxylic acid cyclopropylamide hydrochloride Compound 168 (3S,4S)-3-[2-(4-Methanesulfonyl-benzyl)-1-oxo-2,8-diaza-spiro[4.5]dec-8-ylmethyl]-4-phenyl-pyrrolidine-1-carboxylic acid cyclopentylamide hydrochloride Compound 169 2-(4-Methoxy-benzyl)-8-((3R,4S)-1-methyl-4-phenyl-pyrrolidin-3-ylmethyl)-2,8-diaza-spiro[4.5]decan-1-one dihydrochloride Compound 170 8-((3S,4S)-1-Isopropyl-4-phenyl-pyrrolidin-3-ylmethyl)-2-(4-methoxy-benzyl)-2,8-diaza-spiro[4.5]decan-1-one dihydrochloride Compound 171 8-((3S,4S)-1-Isobutyl-4-phenyl-pyrrolidin-3-ylmethyl)-2-(4-methoxy-benzyl)-2,8-diaza-spiro[4.5]decan-1-one dihydrochloride Compound 172 8-((3S,4S)-1-Cyclopropylmethyl-4-phenyl-pyrrolidin-3-ylmethyl)-2-(4-methoxy-benzyl)-2,8-diaza-spiro[4.5]decan-1-one dihydrochloride Compound 173 2-(4-Methoxy-benzyl)-8-[(3S,4S)-4-phenyl-1-(tetrahydro-pyran-4-ylmethyl)-pyrrolidin-3-ylmethyl]-2,8-diaza-spiro[4.5]decan-1-one dihydrochloride Compound 174 8-[(3S,4S)-1-(4,4-Difluoro-cyclohexylmethyl)-4-phenyl-pyrrolidin-3-ylmethyl]-2-(4-methoxy-benzyl)-2,8-diaza-spiro[4.5]decan-1-one dihydrochloride Compound 175 2-(4-Methanesulfonyl-benzyl)-8-((3R,4S)-1-methyl-4-phenyl-pyrrolidin-3-ylmethyl)-2,8-diaza-spiro[4.5]decan-1-one dihydrochloride Compound 176 8-((3S,4S)-1-Isopropyl-4-phenyl-pyrrolidin-3-ylmethyl)-2-(4-methanesulfonyl-benzyl)-2,8-diaza-spiro[4.5]decan-1-one dihydrochloride Compound 177 8-((3S,4S)-1-Isobutyl-4-phenyl-pyrrolidin-3-ylmethyl)-2-(4-methanesulfonyl-benzyl)-2,8-diaza-spiro[4.5]decan-1-one dihydrochloride Compound 178 8-((3S,4S)-1-Cyclopropylmethyl-4-phenyl-pyrrolidin-3-ylmethyl)-2-(4-methanesulfonyl-benzyl)-2,8-diaza-spiro[4.5]decan-1-one dihydrochloride Compound 179 2-(4-Methanesulfonyl-benzyl)-8-[(3S,4S)-4-phenyl-1-(tetrahydro-pyran-4-ylmethyl)-pyrrolidin-3-ylmethyl]-2,8-diaza-spiro[4.5]decan-1-one dihydrochloride Compound 180 8-[(3S,4S)-1-(4,4-Difluoro-cyclohexylmethyl)-4-phenyl-pyrrolidin-3-ylmethyl]-2-(4-methanesulfonyl-benzyl)-2,8-diaza-spiro[4.5]decan-1-one dihydrochloride Compound 181 (3S,4S)-3-[2-(4-Methoxy-benzyl)-1-oxo-2,8-diaza-spiro[4.5]dec-8-ylmethyl]-4-phenyl-pyrrolidine-1-carboxylic acid methyl ester hydrochloride Compound 182 (3S,4S)-3-[2-(4-Methoxy-benzyl)-1-oxo-2,8-diaza-spiro[4.5]dec-8-ylmethyl]-4-phenyl-pyrrolidine-1-carboxylic acid ethyl ester hydrochloride Compound 183 (3S,4S)-3-[2-(4-Methoxy-benzyl)-1-oxo-2,8-diaza-spiro[4.5]dec-8-ylmethyl]-4-phenyl-pyrrolidine-1-carboxylic acid isopropyl ester hydrochloride Compound 184 (3S,4S)-3-[2-(4-Methoxy-benzyl)-1-oxo-2,8-diaza-spiro[4.5]dec-8-ylmethyl]-4-phenyl-pyrrolidine-1-carboxylic acid cyclopentyl ester hydrochloride Compound 185 (3S,4S)-3-[2-(4-Methoxy-benzyl)-1-oxo-2,8-diaza-spiro[4.5]dec-8-ylmethyl]-4-phenyl-pyrrolidine-1-carboxylic acid cyclohexyl ester hydrochloride Compound 186 (3S,4S)-3-[2-(4-Methanesulfonyl-benzyl)-1-oxo-2,8-diaza-spiro[4.5]dec-8-ylmethyl]-4-phenyl-pyrrolidine-1-carboxylic acid methyl ester hydrochloride Compound 187 (3S,4S)-3-[2-(4-Methanesulfonyl-benzyl)-1-oxo-2,8-diaza-spiro[4.5]dec-8-ylmethyl]-4-phenyl-pyrrolidine-1-carboxylic acid ethyl ester hydrochloride Compound 188 (3S,4S)-3-[2-(4-Methanesulfonyl-benzyl)-1-oxo-2,8-diaza-spiro[4.5]dec-8-ylmethyl]-4-phenyl-pyrrolidine-1-carboxylic acid isopropyl ester hydrochloride Compound 189 (3S,4S)-3-[2-(4-Methanesulfonyl-benzyl)-1-oxo-2,8-diaza-spiro[4.5]dec-8-ylmethyl]-4-phenyl-pyrrolidine-1-carboxylic acid cyclopentyl ester hydrochloride Compound 190 (3S,4S)-3-[2-(4-Methanesulfonyl-benzyl)-1-oxo-2,8-diaza-spiro[4.5]dec-8-ylmethyl]-4-phenyl-pyrrolidine-1-carboxylic acid cyclohexyl ester hydrochloride Compound 191 8-[(3S,4S)-1-(2-Cyclopropyl-acetyl)-4-phenyl-pyrrolidin-3-ylmethyl]-2-(4-fluoro-benzyl)-2,8-diaza-spiro[4.5]decan-1-one hydrochloride Compound 192 2-(4-Chloro-benzyl)-8-[(3S,4S)-1-(2-cyclopropyl-acetyl)-4-phenyl-pyrrolidin-3-ylmethyl]-2,8-diaza-spiro[4.5]decan-1-one hydrochloride Compound 193 4-{8-[(3S,4S)-1-(2-Cyclopropyl-acetyl)-4-phenyl-pyrrolidin-3-ylmethyl]-1-oxo-2,8-diaza-spiro[4.5]dec-2-ylmethyl}-benzonitrile hydrochloride Compound 194 8-[(3S,4S)-1-(2-Cyclopropyl-acetyl)-4-phenyl-pyrrolidin-3-ylmethyl]-2-(4-difluoromethoxy-benzyl)-2,8-diaza-spiro[4.5]decan-1-one hydrochloride Compound 195 8-[(3S,4S)-1-(2-Cyclopropyl-acetyl)-4-phenyl-pyrrolidin-3-ylmethyl]-2-(4-trifluoromethoxy-benzyl)-2,8-diaza-spiro[4.5]decan-1-one hydrochloride Compound 196 8-[(3S,4S)-1-(2-Cyclopropyl-acetyl)-4-phenyl-pyrrolidin-3-ylmethyl]-2-(4-trifluoromethyl-benzyl)-2,8-diaza-spiro[4.5]decan-1-one hydrochloride Compound 197 8-[(3S,4S)-1-(2-Cyclopropyl-acetyl)-4-phenyl-pyrrolidin-3-ylmethyl]-2-(4-pyrazol-1-yl-benzyl)-2,8-diaza-spiro[4.5]decan-1-one hydrochloride Compound 198 2-(4-Fluoro-benzyl)-8-((3S,4S)-4-phenyl-1-propionyl-pyrrolidin-3-ylmethyl)-2,8-diaza-spiro[4.5]decan-1-one hydrochloride Compound 199 2-(4-Chloro-benzyl)-8-((3S,4S)-4-phenyl-1-propionyl-pyrrolidin-3-ylmethyl)-2,8-diaza-spiro[4.5]decan-1-one hydrochloride Compound 200 4-[1-Oxo-8-((3S,4S)-4-phenyl-1-propionyl-pyrrolidin-3-ylmethyl)-2,8-diaza-spiro[4.5]dec-2-ylmethyl]-benzonitrile hydrochloride Compound 201 2-(4-Difluoromethoxy-benzyl)-8-((3S,4S)-4-phenyl-1-propionyl-pyrrolidin-3-ylmethyl)-2,8-diaza-spiro[4.5]decan-1-one hydrochloride Compound 202 8-((3S,4S)-4-Phenyl-1-propionyl-pyrrolidin-3-ylmethyl)-2-(4-trifluoromethoxy-benzyl)-2,8-diaza-spiro[4.5]decan-1-one hydrochloride Compound 203 8-((3S,4S)-4-Phenyl-1-propionyl-pyrrolidin-3-ylmethyl)-2-(4-trifluoromethyl-benzyl)-2,8-diaza-spiro[4.5]decan-1-one hydrochloride Compound 204 8-((3S,4S)-4-Phenyl-1-propionyl-pyrrolidin-3-ylmethyl)-2-(4-pyrazol-1-yl-benzyl)-2,8-diaza-spiro[4.5]decan-1-one hydrochloride.

or pharmaceutically acceptable salts, hydrates or solvates thereof.

It will be appreciated that the amount of a compound of the invention required for use in treatment will vary not only with the particular compound selected but also with the route of administration, the nature of the condition for which treatment is required and the age and condition of the patient and will be ultimately at the discretion of the attendant physician or veterinarian. In general however a suitable dose will be in the range of from about 0.1 to about 750 mg/kg of body weight per day, preferably in the range of 0.5 to 60 mg/kg/day, most preferably in the range of 1 to 20 mg/kg/day.

The desired dose may conveniently be presented in a single dose or as divided dose administered at appropriate intervals, for example as two, three, four or more doses per day.

The compound is conveniently administered in unit dosage form; for example containing 10 to 1500 mg, conveniently 20 to 1000 mg, most conveniently 50 to 700 mg of active ingredient per unit dosage form.

Ideally the active ingredient should be administered to achieve peak plasma concentrations of the active compound of from about 1 to about 75 µM, preferably about 2 to 50 µM, most preferably about 3 to about 30 µM. This may be achieved, for example, by the intravenous injection of a 0.1 to 5% solution of the active ingredient, optionally in saline, or orally administered as a bolus containing about 1 to about 500 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible that, for use in therapy, a compound of the invention may be administered as the raw chemical it is preferable to present the active ingredient as a pharmaceutical formulation. The invention thus further provides a pharmaceutical formulation comprising a compound of formula (I) or a pharmaceutically acceptable derivative thereof together with one or more pharmaceutically acceptable carriers therefore and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), transdermal, vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulation suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

For topical administration to the epidermis, the compounds according to the invention may be formulated as ointments, creams or lotions, or as a transdermal patch. Such transdermal patches may contain penetration enhancers such as linalool, carvacrol, thymol, citral, menthol and t-anethole. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Formulations suitable for vaginal administration may be presented as pessaries, tampons, creams, gels, pastes, foams or sprays containing in addition to the active ingredient such carriers as are known in the art to be appropriate.

For intra-nasal administration the compounds of the invention may be used as a liquid spray or dispersible powder or in the form of drops. Drops may be formulated with an aqueous or non-aqueous base also comprising one more dispersing agents, solubilising agents or suspending agents. Liquid sprays are conveniently delivered from pressurized packs.

For administration by inhalation the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

When desired the above described formulations adapted to give sustained release of the active ingredient may be employed.

When the compound (I) or a pharmaceutically acceptable salt, hydrate or solvate thereof is used in combination with a second therapeutic active agent, the dose of each compound may be either the same as or different from that when the compound is used alone. Conventional doses and regimens are readily appreciated by those skilled in the art, including doses described in the Physicians Desk Reference, $56^{th}$ edition, 2002.

The present invention is directed to the use of the compounds as modulators of CCR5 chemokine receptor activity. In particular, the compounds of the invention have been found to have activity in binding to the CCR5 receptor in the biological assay, as described in Example 14, generally with an $IC_{50}$ value of less than 25 µM. The terms "modulator" or "modulation" are meant to include antagonism, agonism, mixed and partial antagonism and agonism.

Certain compounds of the present invention have also been tested in an assay for HIV activity, as described in Example 14, and generally having an $IC_{50}$ value of less than 1 µM.

The purity and mass of the following examples were characterized by mass spectra (LC/MS) and/or NMR spectra.

The following general schemes and examples are provided to illustrate various embodiments of the present invention and shall not be considered as limiting in scope.

The entire disclosure of all applications, patents and publications, cited above and below, and of U.S. Provisional Application No. 60/501,407, filed Sep. 10, 2003 is hereby incorporated by reference.

In the foregoing and in the following examples, all temperatures are set forth uncorrected in degrees Celsius; and, unless otherwise indicated, all parts and percentages are by weight. (Note: yields are by weight but chromatographic conditions are by volume.)

EXAMPLES

The following abbreviations may be used as follows:
br broad
DCE 1,2-dichloroethane
DCM dichloromethane
DIPEA N,N-diisopropylethylamine
DMF N,N-dimethylformamide
Hal halogen
TFA trifluoroacetic acid
THF tetrahydrofuran.
Semi-Preparative HPLC Purification Procedures:

Column: Phenomenex Luna C$_{18}$(2), 5 microns, 10×250 mm
Buffer A: 3 mM HCl in H$_2$O (pH 2.4-2.6)
Buffer B: acetonitrile
  Method A: 15% B (5 min.) and 15-55% B in 30 min. (1.4%/min)
  Method B: 10-65% B in 55 min. (1.0%/min)
  Method C: 0-25% B in 25 min. (1.0%/min)
  Method D: 15-40% B in 25 min. (1.0%/min).

Scheme 1

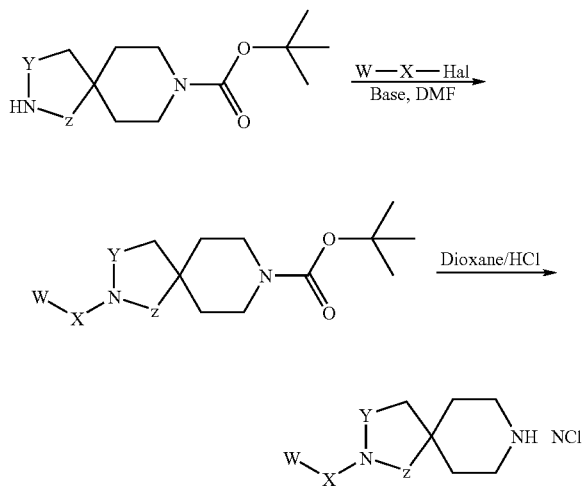

Preparation 1

2-(4-Bromobenzyl)-1-oxo-2,8-diaza-spiro[4.5]decane-8-carboxylic acid tert-butyl ester

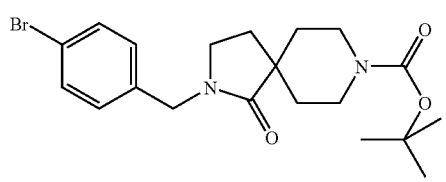

Introduce 600 mg (14.7 mmol) of sodium hydride (60% suspension in mineral oil) in a 500 mL round bottom flask under nitrogen before adding successively 20 mL of anhydrous DMF and 2.5 g (9.8 mmol) of 1-oxo-2,8-diaza-spiro[4.5]decane-8-carboxylic acid tert-butyl ester previously dissolved in 20 mL of anhydrous DMF. After agitating one hour at room temperature, 2.5 g (9.8 mmol) of 4-bromobenzylbromide diluted in 20 mL of anhydrous DMF were added and the reaction mixture was agitated an additional hour at room temperature. Then 100 mL of water were added and the solution was extracted with diethyl ether (2×150 mL). The combined organic layers were dried (Na$_2$SO$_4$), filtered and evaporated under reduced pressure to yield 4.63 g of 2-(4-bromobenzyl)-1-oxo-2,8-diaza-spiro[4.5]decane-8-carboxylic acid tert-butyl ester as a yellow oil.

$^1$H NMR (400 MHz, DMSO-d$_6$): δ [ppm] 7.51 (d, 2H), 7.12 (d, 2H), 4.31 (s, 2H), 3.8 (br d, 2H), 3.14 (t, 2H), 2.86 (br s, 2H), 1.89 (t, 2H), 1.54 (t×d, 2H), 1.37 (s, 9H), 1.32 (br d, 2H).

Preparation 2

2-(4-Bromobenzyl)-2,8-diaza-spiro[4.5]decan-1-one hydrochloride

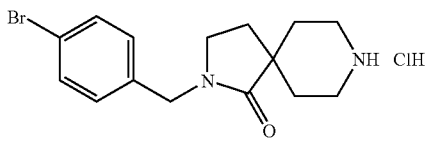

To 4.62 g of crude 2-(4-bromobenzyl)-1-oxo-2,8-diaza-spiro[4.5]decane-8-carboxylic acid tert-butyl ester from preparation 1 were added 50 mL of 4N solution of dioxane/HCl. The reaction mixture was agitated 15 minutes at room temperature and 3.05 g (77.8%) of 2-(4-bromobenzyl)-2,8-diaza-spiro[4.5]decan-1-one hydrochloride was collected, as a colorless solid, after filtration and subsequent wash steps with diethyl ether.

$^1$H NMR (400 MHz, DMSO-d$_6$): δ [ppm] 9.15 (br s, 1H), 8.83 (br s, 1H), 7.51 (d, 2H), 7.14 (d, 2H), 4.31 (s, 2H), 3.24 (br d, 2H), 3.15 (t, 2H), 2.92 (q, 2H), 1.95-1.84 (m, 4H), 1.56 (br d, 2H).

Preparation 3

2-(4-Methylsulfanylbenzyl)-1-oxo-2,8-diaza-spiro[4.5]decane-8-carboxylic acid tert-butyl ester

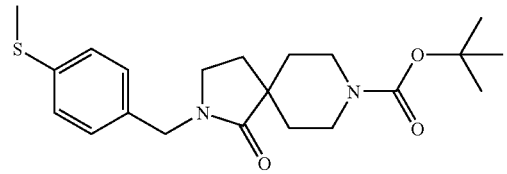

This spiro compound was prepared as described in preparation 1, starting from 7 g (27.5 mmol) of 1-oxo-2,8-diaza-spiro[4.5]decane-8-carboxylic acid tert-butyl ester, except it was purified by flash chromatography on silica gel (ethyl acetate/hexanes 0:100 to 20:80) yielding 8.05 g (74.9%) of 2-(4-methylsulfanylbenzyl)-1-oxo-2,8-diaza-spiro[4.5]decane-8-carboxylic acid tert-butyl ester as a pale yellow solid.

$^1$H NMR (400 MHz, DMSO-d$_6$): δ [ppm] 7.21 (d, 2H), 7.11 (d, 2H), 4.3 (s, 2H), 3.8 (br d, 2H), 3.13 (t, 2H), 2.88 (br s, 2H), 2.43 (s, 3H), 1.89 (t, 2H), 1.54 (t×d, 2H), 1.38 (s, 9H), 1.31 (br d, 2H).

Preparation 4

2-(4-Methanesulfonylbenzyl)-1-oxo-2,8-diaza-spiro[4.5]decane-8-carboxylic acid tert-butyl ester

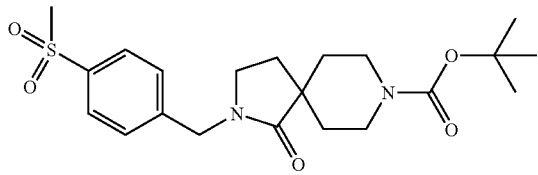

To 7.73 g (19.8 mmol) of 2-(4-methylsulfanylbenzyl)-1-oxo-2,8-diaza-spiro[4.5]decane-8-carboxylic acid tert-butyl ester, previously dissolved in 100 mL of THF, were added 18.2 g (29.7 mmol) of Oxone® in 100 mL of water. The reaction mixture was agitated overnight at room temperature. Then 100 mL of 1N aqueous solution of sodium hydroxide were added and the solution was extracted with DCM (2×200 mL). The combined organic layers were dried (Na$_2$SO$_4$), filtered and evaporated under reduced pressure to yield 6.62 g (79.1%) of 2-(4-methanesulfonylbenzyl)-1-oxo-2,8-diaza-spiro[4.5]decane-8-carboxylic acid tert-butyl ester as a white solid.

$^1$H NMR (400 MHz, DMSO-d$_6$): δ [ppm] 7.81 (d, 2H), 7.37 (d, 2H), 4.41 (s, 2H), 3.76 (br d, 2H), 3.15 (t, 2H), 3.14 (s, 3H), 2.86 (br s, 2H), 1.89 (t, 2H), 1.52 (txd, 2H), 1.33 (s, 9H), 1.29 (br d, 2H).

LC/MS: m/z 423.2 (MH$^+$).

Preparation 5

2-(4-Methanesulfonylbenzyl)-2,8-diaza-spiro[4.5]decan-1-one hydrochloride

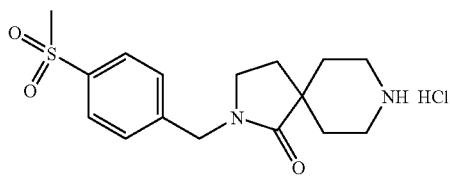

As described in preparation 2, 6.62 g (15.6 mmol) of 2-(4-methanesulfonylbenzyl)-1-oxo-2,8-diaza-spiro[4.5]decane-8-carboxylic acid tert-butyl ester was deprotected under acidic conditions giving access to 5.25 g (93.7%) of 2-(4-methanesulfonylbenzyl)-2,8-diaza-spiro[4.5]decan-1-one hydrochloride as a white solid.

$^1$H NMR (400 MHz, DMSO-d$_6$): δ [ppm] 9.04 (br s, 1H), 8.74 (br s, 1H), 7.83 (d, 2H), 7.39 (d, 2H), 4.42 (s, 2H), 3.21 (br d, 2H), 3.15 (t, 2H), 3.13 (s, 3H), 2.89 (q, 2H), 1.92 (t, 2H), 1.84 (txd, 2H), 1.55 (br d, 2H).

Preparation 6

2-(4-Bromobenzyl)-3-oxo-2,8-diaza-spiro[4.5]decane-8-carboxylic acid tert-butyl ester

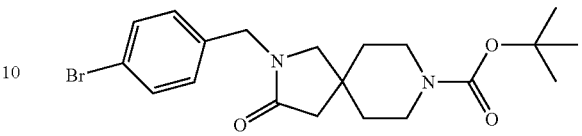

This spiro compound was prepared as described in preparation 1, starting from 300 mg (1.18 mmol) of 3-oxo-2,8-diaza-spiro[4.5]decane-8-carboxylic acid tert-butyl ester, except it was purified by flash chromatography on silica gel (ethyl acetate/hexanes 0:100 to 60:40) yielding 290 mg (58%) of 2-(4-bromobenzyl)-3-oxo-2,8-diaza-spiro[4.5]decane-8-carboxylic acid tert-butyl ester as a colorless oil.

$^1$H NMR (400 MHz, DMSO-d$_6$): δ [ppm] 7.52 (d, 2H), 7.16 (d, 2H), 4.31 (s, 2H), 3.32 (m, 2H), 3.16 (br s, 2H), 3.02 (s, 2H), 2.25 (s, 2H), 1.4 (m, 4H), 1.35 (s, 9H).

Preparation 7

2-(4-Bromobenzyl)-2,8-diaza-spiro[4.5]decan-3-one hydrochloride

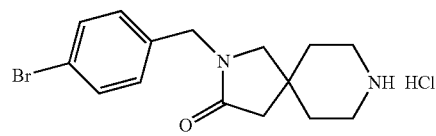

As described in preparation 2, 290 mg (0.68 mmol) of 2-(4-bromobenzyl)-3-oxo-2,8-diaza-spiro[4.5]decane-8-carboxylic acid tert-butyl ester were deprotected under acidic conditions giving access to 212 mg (86.6%) of 2-(4-bromobenzyl)-2,8-diaza-spiro[4.5]decan-3-one hydrochloride as a white solid.

$^1$H NMR (400 MHz, DMSO-d$_6$): δ [ppm] 8.63 (br s, 2H), 7.52 (d, 2H), 7.17 (d, 2H), 4.32 (s, 2H), 3.07 (s, 2H), 3.00 (m, 4H), 2.33 (s, 2H), 1.65 (m, 4H).

Scheme 2

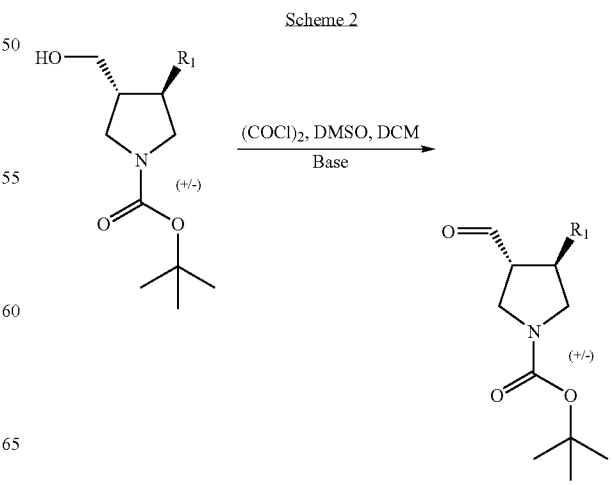

Preparation 8

3-(RS)-Formyl-4-(SR)-phenylpyrrolidine-1-carboxylic acid tert-butyl ester

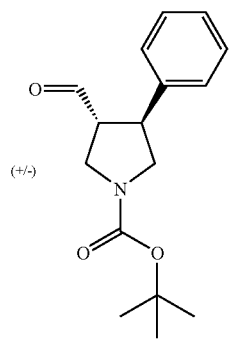

To a solution of 13.1 mL (26.25 mmol) of oxalyl chloride (2M in DCM) in 13 mL of anhydrous DCM were added 3.72 mL (52.5 mmol) of DMSO at −78° C. After 5 minutes of stirring, 3 g (10.5 mmol) of 3-(RS)-hydroxymethyl-4-(SR)-phenylpyrrolidine-1-carboxylic acid tert-butyl ester, previously dissolved in 15 mL of anhydrous DCM, were added dropwise. After 30 minutes additional agitation at −78° C., 18.5 mL (105 mmol) of DIPEA were added dropwise. An additional 30 minutes of agitation at 0° C. and the reaction mixture was quenched with 10 mL of water. 100 mL of water were again added and the solution was extracted with DCM (2×100 mL). The combined organic layers were dried over sodium sulfate, filtered and evaporated in vacuo. The crude yellow oil was purified by flash chromatography on silica gel (ethyl acetate/hexanes 0:100 to 20:80) yielding 2.42 g (83.7%) of 3-(RS)-formyl-4-(SR)-phenylpyrrolidine-1-carboxylic acid tert-butyl ester as a pale yellow oil.

$^1$H NMR (400 MHz, DMSO-$d_6$): δ [ppm] 9.55 (d, 1H), 7.31 (m, 4H), 7.24 (m, 1H), 3.71-3.56 (m, 4H), 3.29 (m, 2H), 1.39 (d, 9H).

Scheme 3

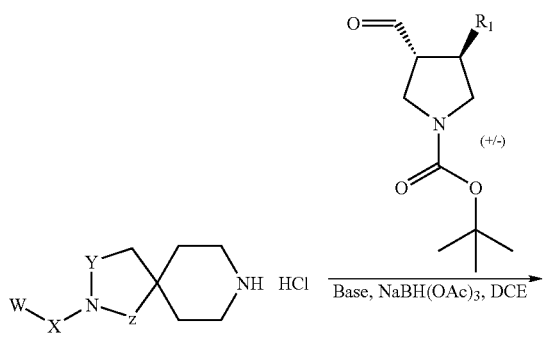

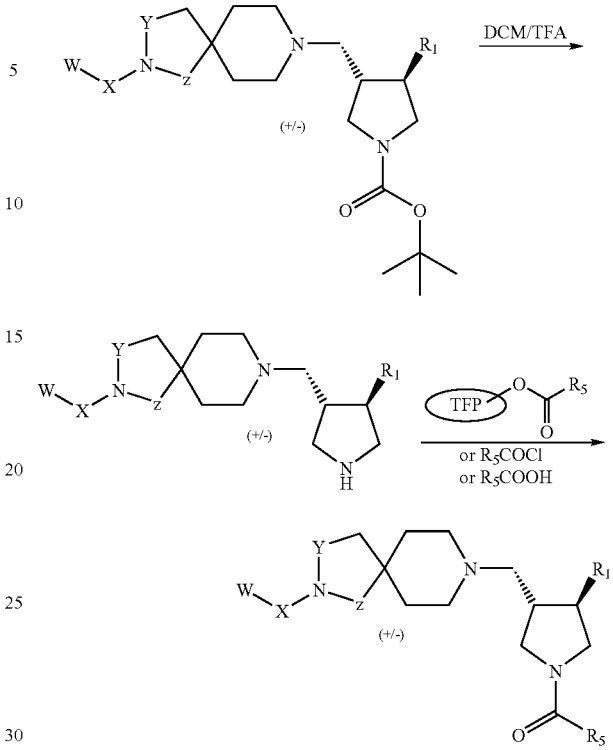

Example 1

3-(RS)-[2-(4-Bromobenzyl)-1-oxo-2,8-diaza-spiro[4.5]dec-8-ylmethyl]-4-(SR)-phenylpyrrolidine-1-carboxylic acid tert-butyl ester (Compound 1)

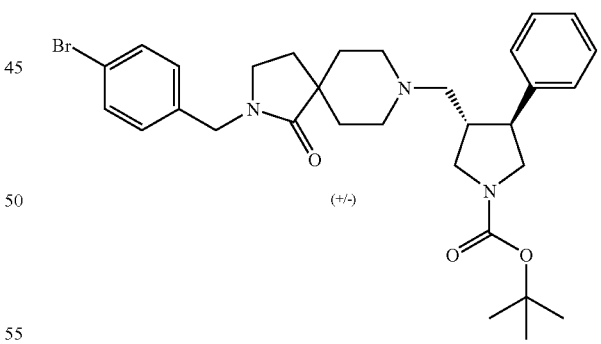

To 275.3 mg (1 mmol) of 3-(RS)-formyl-4-(SR)-phenylpyrrolidine-1-carboxylic acid tert-butyl ester and 359.1 mg (1 mmol) of 2-(4-bromobenzyl)-2,8-diaza-spiro[4.5]decan-1-one hydrochloride were added 20 mL of DCE and 139 μL (1 mmol) of triethylamine. The reaction mixture was agitated for 10 minutes at room temperature before adding 334 mg (1.5 mmol) of triacetoxyborohydride. After an overnight agitation, 10 mL of saturated solution of sodium bicarbonate were added and the solution was extracted with DCM. The organic layers were dried over sodium sulfate, filtered and evaporated in vacuo. The crude yellow oil was purified by flash chromatography on silica gel (DCM/methanol 0% to 2%) giving Compound 1 as a colorless solid (520 mg, 89.3%).

$^1$H NMR (400 MHz, DMSO-d$_6$): δ [ppm] 7.5 (d, 2H), 7.28 (m, 4H), 7.21 (m, 1H), 7.11 (d, 2H), 4.3 (s, 2H), 3.63 (m, 2H), 3.17 (m, 1H), 3.08 (t, 2H), 2.98 (m, 2H), 2.79 (m, 1H), 2.57 (m, 2H), 2.26 (t, 1H), 2.06 (m, 1H), 1.93 (m, 1H), 1.76 (t, 2H), 1.63 (m, 3H), 1.39 (d, 9H), 1.25 (m, 2H).

Example 2

2-(4-Bromobenzyl)-8-(4-(SR)-phenylpyrrolidin-3-(RS)-ylmethyl)-2,8-diaza-spiro[4.5]decan-1-one (Compound 3)

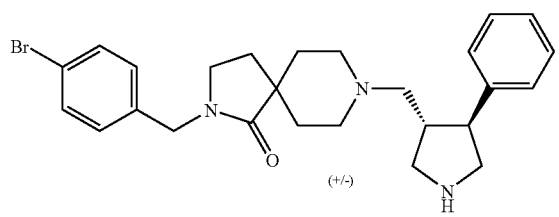

To 510 mg (0.87 mmol) of 3-(RS)-[2-(4-bromobenzyl)-1-oxo-2,8-diaza-spiro[4.5]dec-8-ylmethyl]-4-(SR)-phenylpyrroli-dine-1-carboxylic acid tert-butyl ester was added a solution of DCM/TFA 20% (12 mL). The reaction mixture was agitated for one hour at room temperature before quenching with 30 mL of aqueous solution of sodium hydroxide (1N). The solution was then extracted with DCM (2×20 mL). The combined organic layers were dried over sodium sulfate, filtered and evaporated in vacuo yielding Compound 3 as a pale yellow solid (420 mg, 99.4%).

$^1$H NMR (400 MHz, DMSO-d$_6$): δ [ppm] 7.50 (d, 2H), 7.24 (m, 4H), 7.14 (m, 1H), 7.10 (d, 2H), 4.29 (s, 2H), 3.15 (d×d, 1H), 3.07 (t, 3H), 2.72-2.52 (m, 5H), 2.22 (m, 3H), 1.86 (t×d, 1H), 1.77 (m, 3H), 1.68-1.55 (m, 2H), 1.26-1.17 (m, 2H).

Example 3

8-(1-Benzoyl-4-(SR)-phenylpyrrolidin-3-(RS)-ylmethyl)-2-(4-bromobenzyl)-2,8-diaza-spiro[4.5]decan-1-one hydrochloride (Compound 2)

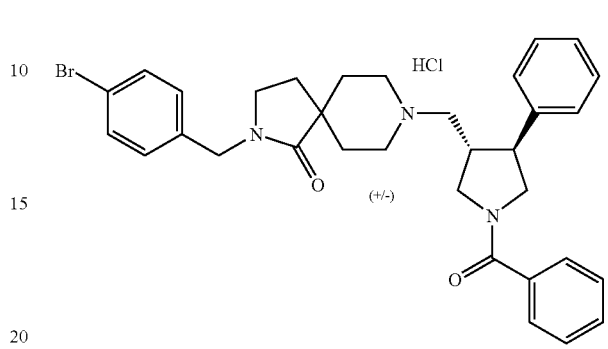

To 100 mg (100 μmol, loading of 1 mmol/g) of phenylcarboxyl activated ester on polymeric 4-hydroxy-2,3,5,6-tetrafluorobenzamido (TFP) resin (see preparation in J. M. Salvino et al. *J. Comb. Chem.* 2000, 2, 691-697), preswollen with 0.5 mL of anhydrous DMF, was added 28.9 mg (60 μmol) of 2-(4-bromobenzyl)-8-(4-(SR)-phenylpyrrolidin-3-(RS)-ylmethyl)-2,8-diaza-spiro[4.5]decan-1-one diluted in 1 mL of DMF. The reaction was agitated overnight at room temperature. The mixture was filtered and washed with DCM (2×2 mL). The washes were collected and evaporated in vacuo. The crude was purified by semi-preparative HPLC (method A) and 13.9 mg (37.2%) of Compound 2 as a colorless solid was isolated.

$^1$H NMR (400 MHz, DMSO-d$_6$): δ [ppm] 9.04 (br d, 1H), 7.56-7.26 (m, 12H), 7.12 (m, 2H), 4.31 (d, 2H), 4.12 (m, 1H), 3.93 (m, 1H), 3.71 (m, 1H), 3.64-3.36 (m, 4H), 3.24-2.82 (m, 8H) 2.06-1.78 (m, 4H), 1.57 (m, 2H).

LC/MS: m/z 588.1 (MH$^+$).

Table 1 of compounds illustrates some of the compounds of the present invention that were synthesized using the procedure described in scheme 3.

TABLE 1

| CPD # | STRUCTURE | COMPOUND NAME | MOL WT | PURITY |
|---|---|---|---|---|
| 1 | 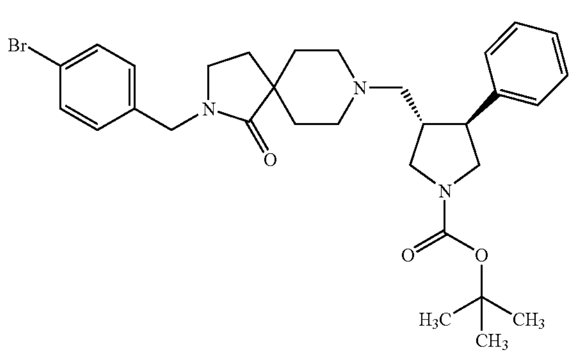 | 3-(RS)-[2-(4-Bromo-benzyl)-2-oxo-2,8-diaza-spiro[4.5]dec-8-ylmethyl]-4-(SR)-phenylpyrrolidine-1-carboxylic acid tert-butyl ester | 582.579 | >95% (1H NMR) |

TABLE 1-continued

| CPD # | STRUCTURE | COMPOUND NAME | MOL WT | PURITY |
|---|---|---|---|---|
| 2 | 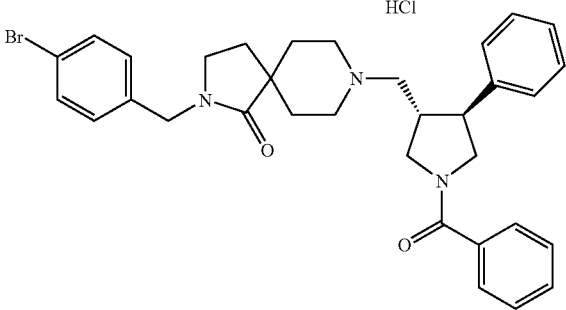 | 8-(1-Benzoyl-4-(SR)-phenyl-pyrrolidin-3-(RS)-ylmethyl)-2-(4-bromo-benzyl)-2,8-diaza-spiro[4.5]decan-1-one hydrochloride | 623.031 | 98+ (LC/MS) |
| 3 | 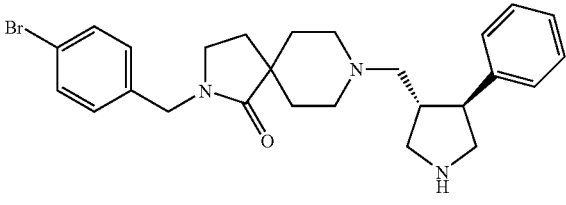 | 2-(4-Bromobenzyl)-8-(4-(SR)-phenyl-pyrrolidin-3-(RS)-ylmethyl)-2,8-diaza-spiro[4.5]decan-1-one | 482.463 | >95% (1H NMR) |
| 4 | 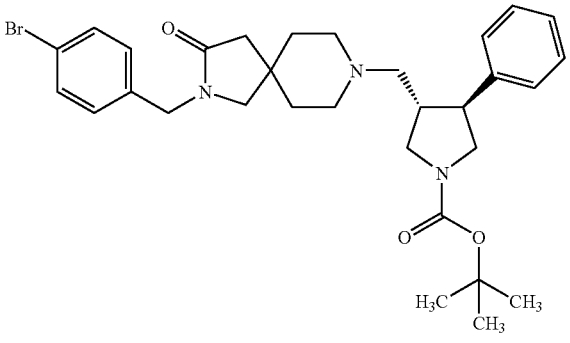 | 3-(RS)-[2-(4-Bromobenzyl)-3-oxo-2,8-diaza-spiro[4.5]dec-8-yl-methyl]-4-(SR)-phenyl-pyrrolidine-1-carboxylic acid tert-butyl ester | 582.579 | >95% (1H NMR) |
| 5 | 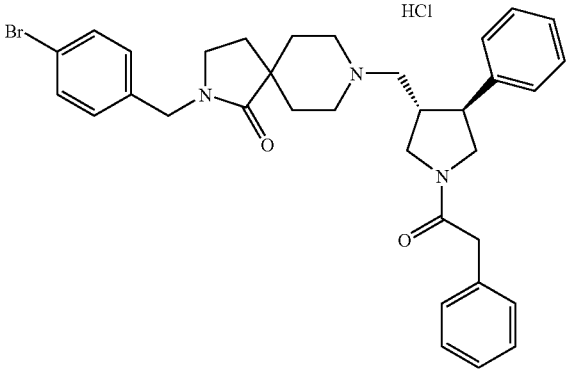 | 2-(4-Bromobenzyl)-8-(4-(SR)-phenyl-1-phenylacetyl-pyrrolidin-3-(RS)-ylmethyl)-2,8-diaza-spiro[4.5]decan-1-one hydrochloride | 637.058 | 98+ (LC/MS) |

TABLE 1-continued

| CPD # | STRUCTURE | COMPOUND NAME | MOL WT | PURITY |
|---|---|---|---|---|
| 6 | 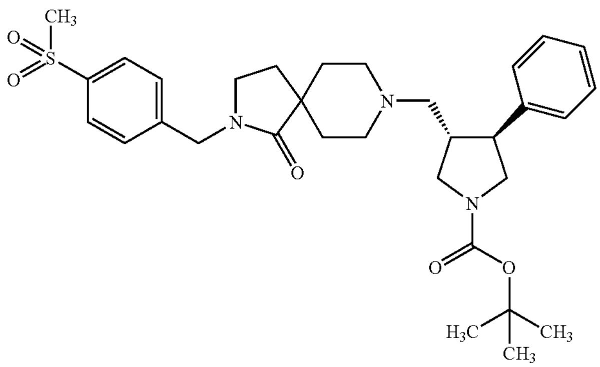 | 3-(RS)-[2-(4-Methane-sulfonylbenzyl)-1-oxo-2,8-di-aza-spiro[4.5]dec-8-yl-methyl]-4-(SR)-phenyl-pyrrolidine-1-carboxylic acid tert-butyl ester | 581.774 | >90% (1H NMR) |
| 7 | 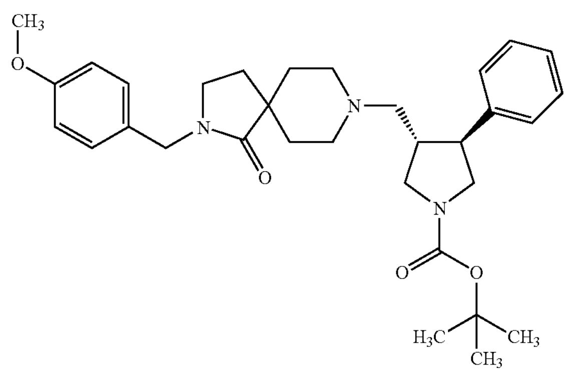 | 3-(RS)-[2-(4-Methoxybenzyl)-1-oxo-2,8-di-aza-spiro[4.5]dec-8-yl-methyl]-4-(SR)-phenylpyrrolidine-1-carboxylic acid tert-butyl ester | 533.709 | >95% (1H NMR) |
| 8 | 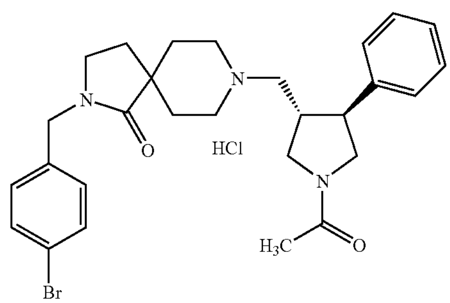 | 8-(1-Acetyl-4-(SR)-phenyl-pyrrolidin-3-(RS)-ylmethyl)-2-(4-bromo-benzyl)-2,8-diaza-spiro[4.5]de-can-1-one hydrochloride | 560.961 | 98+ (LC/MS) |
| 9 | 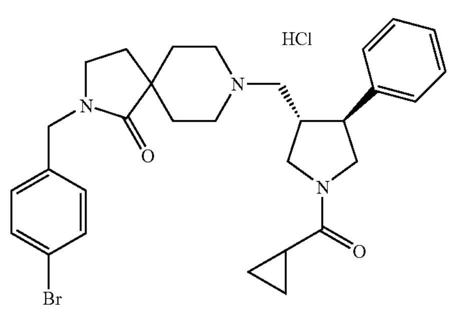 | 2-(4-Bromobenzyl)-8-(1-cyclo-propanecarbonyl-4-(SR)-phenyl-pyrrolidin-3-(RS)-ylmethyl)-2,8-di-aza-spiro[4.5]decan-1-one hydrochloride | 586.998 | 98+ (LC/MS) |

TABLE 1-continued

| CPD # | STRUCTURE | COMPOUND NAME | MOL WT | PURITY |
|---|---|---|---|---|
| 10 | 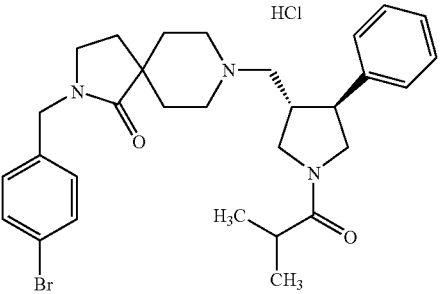 | 2-(4-Bromobenzyl)-8-(1-iso-butyryl-4-(SR)-phenyl-pyrrolidin-3-(RS)-yl-methyl)-2,8-diaza-spiro[4.5]decan-1-one hydrochloride | 589.014 | 98+ (LC/MS) |
| 11 | 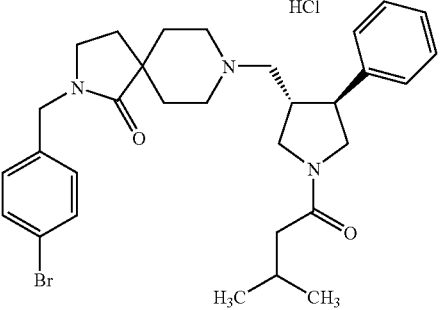 | 2-(4-Bromobenzyl)-8-[1-(3-methyl-butyryl)-4-(SR)-phenylpyrrolidin-3-(RS)-yl-methyl]-2,8-diaza-spiro[4.5]decan-1-one hydrochloride | 603.041 | 98+ (LC/MS) |
| 12 | 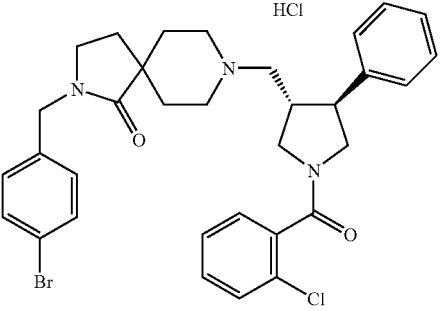 | 2-(4-Bromobenzyl)-8-[1-(2-chloro-benzoyl)-4-(SR)-phenylpyrrolidin-3-(RS)-yl-methyl]-2,8-diaza-spiro[4.5]decan-1-one hydrochloride | 657.476 | 98+ (LC/MS) |
| 13 | 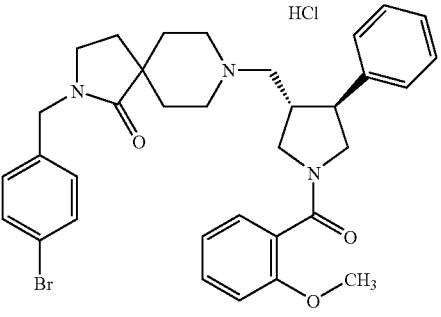 | 2-(4-Bromobenzyl)-8-[1-(2-methoxybenzoyl)-4-(SR)-phenyl-pyrrolidin-3-(RS)-ylmethyl]-2,8-diaza-spiro[4.5]decan-1-one hydrochloride | 653.057 | 98+ (LC/MS) |

TABLE 1-continued

| CPD # | STRUCTURE | COMPOUND NAME | MOL WT | PURITY |
|---|---|---|---|---|
| 14 | 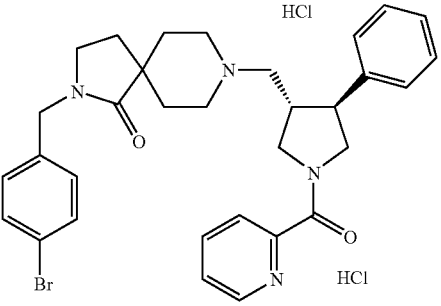 | 2-(4-Bromobenzyl)-8-[4-(SR)-phenyl-1-(pyridine-2-carbonyl)-pyrrolidin-3-(RS)-ylmethyl]-2,8-diaza-spiro[4.5]decan-1-one dihydrochloride | 660.48 | 95.1% (LC/MS) |
| 15 | 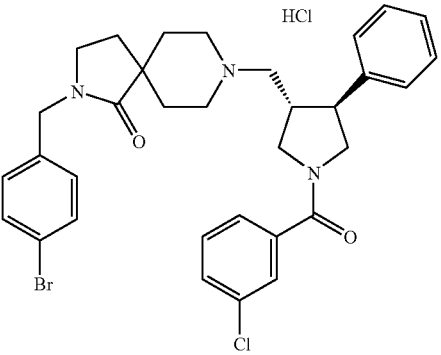 | 2-(4-Bromobenzyl)-8-[1-(3-chlorobenzoyl)-4-(SR)-phenyl-pyrrolidin-3-(RS)-ylmethyl]-2,8-diaza-spiro[4.5]decan-1-one hydrochloride | 657.476 | 98+ (LC/MS) |
| 16 | 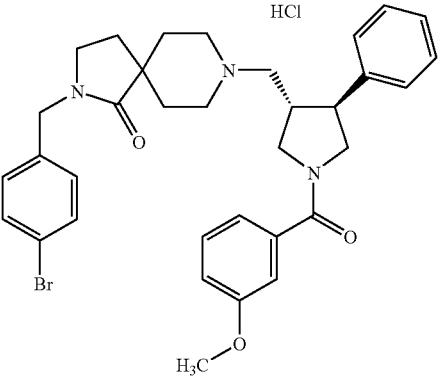 | 2-(4-Bromobenzyl)-8-[1-(3-methoxybenzoyl)-4-(SR)-phenyl-pyrrolidin-3-(RS)-ylmethyl]-2,8-diaza-spiro[4.5]decan-1-one hydrochloride | 653.057 | 98+ (LC/MS) |
| 17 | 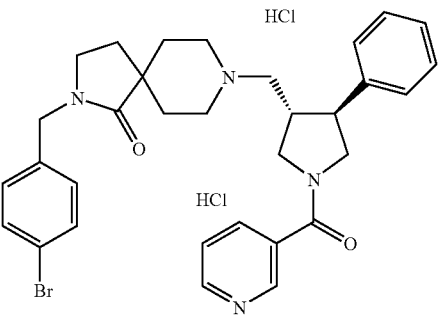 | 2-(4-Bromobenzyl)-8-[4-(SR)-phenyl-1-(pyridine-3-carbonyl)-pyrrolidin-3-(RS)-ylmethyl]-2,8-diaza-spiro[4.5]decan-1-one dihydrochloride | 660.48 | 98+ (LC/MS) |

TABLE 1-continued

| CPD # | STRUCTURE | COMPOUND NAME | MOL WT | PURITY |
|---|---|---|---|---|
| 18 | 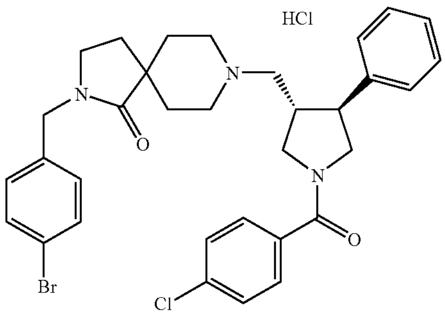 | 2-(4-Bromobenzyl)-8-[1-(4-chlorobenzoyl)-4-(SR)-phenyl-pyrrolidin-3-(RS)-ylmethyl]-2,8-diaza-spiro[4.5]decan-1-one hydrochloride | 657.476 | 98+ (LC/MS) |
| 19 | 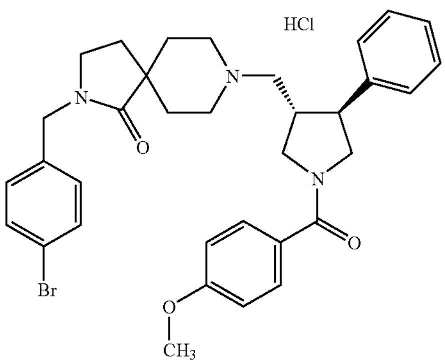 | 2-(4-Bromobenzyl)-8-[1-(4-methoxybenzoyl)-4-(SR)-phenyl-pyrrolidin-3-(RS)-ylmethyl]-2,8-diaza-spiro[4.5]decan-1-one hydrochloride | 653.057 | 98+ (LC/MS) |
| 20 | 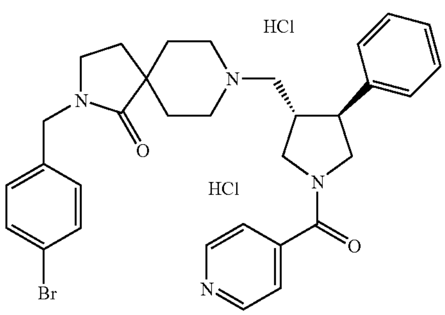 | 2-(4-Bromobenzyl)-8-[4-(SR)-phenyl-1-(pyridine-4-carbonyl)-pyrrolidin-3-(RS)-ylmethyl]-2,8-diaza-spiro[4.5]decan-1-one dihydrochloride | 660.48 | 98+ (LC/MS) |
| 21 | 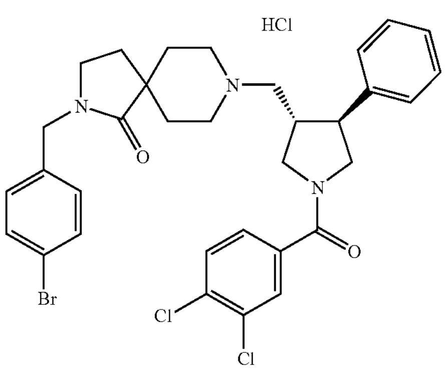 | 2-(4-Bromobenzyl)-8-[1-(3,4-dichlorobenzoyl)-4-(SR)-phenyl-pyrrolidin-3-(RS)-ylmethyl]-2,8-diaza-spiro[4.5]decan-1-one hydrochloride | 691.922 | 98+ (LC/MS) |

TABLE 1-continued

| CPD # | STRUCTURE | COMPOUND NAME | MOL WT | PURITY |
|---|---|---|---|---|
| 22 | 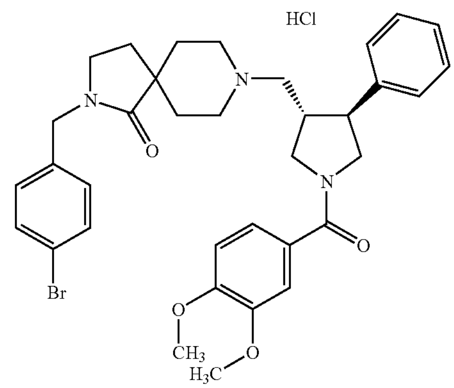 | 2-(4-Bromobenzyl)-8-[1-(3,4-dimethoxybenzoyl)-4-(SR)-phenyl-pyrrolidin-3-(RS)-ylmethyl]-2,8-diaza-spiro[4.5]decan-1-one hydrochloride | 683.083 | 98+ (LC/MS) |
| 23 | 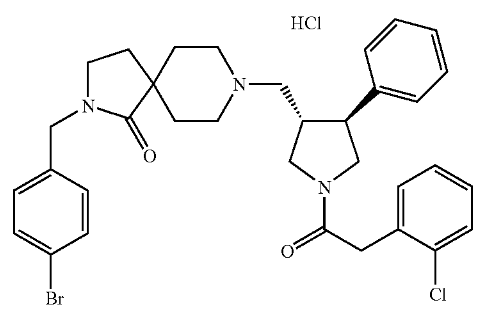 | 2-(4-Bromobenzyl)-8-{1-[2-(2-chlorophenyl)-acetyl]-4-(SR)-phenyl-pyrrolidin-3-(RS)-ylmethyl}-2,8-diaza-spiro[4.5]decan-1-one hydrochloride | 671.503 | 98+ (LC/MS) |
| 24 | 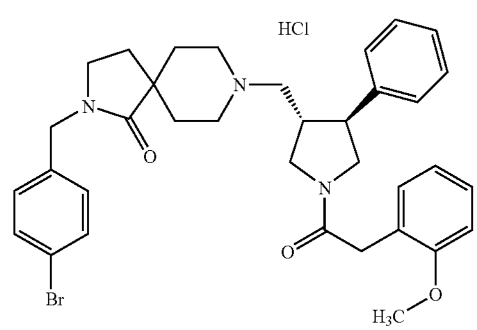 | 2-(4-Bromobenzyl)-8-{1-[2-(2-methoxyphenyl)-acetyl]-4-(SR)-phenyl-pyrrolidin-3-(RS)-ylmethyl}-2,8-diaza-spiro[4.5]decan-1-one hydrochloride | 667.084 | 98+ (LC/MS) |
| 25 | 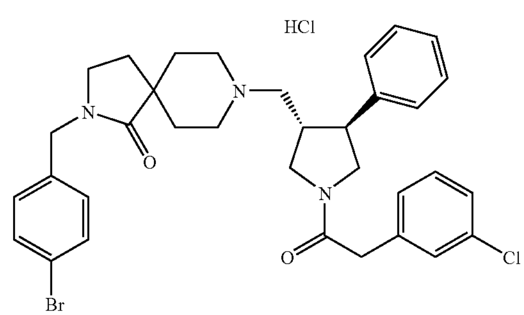 | 2-(4-Bromobenzyl)-8-{1-[2-(3-chlorophenyl)-acetyl]-4-(SR)-phenyl-pyrrolidin-3-(RS)-ylmethyl}-2,8-diaza-spiro[4.5]decan-1-one hydrochloride | 671.503 | 98+ (LC/MS) |

TABLE 1-continued

| CPD # | STRUCTURE | COMPOUND NAME | MOL WT | PURITY |
|---|---|---|---|---|
| 26 | 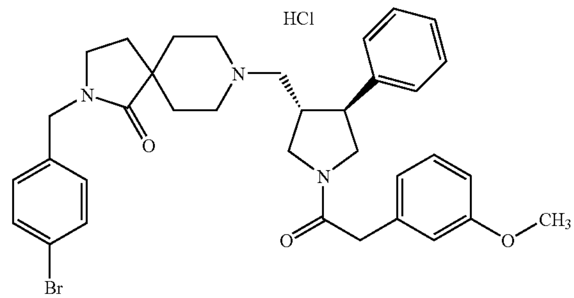 | 2-(4-Bromo-benzyl)-8-{1-[2-(3-methoxy-phenyl)-acetyl]-4-(SR)-phenyl-pyrrolidin-3-(RS)-ylmethyl}-2,8-diaza-spiro[4.5]decan-1-one hydrochloride | 667.084 | 98+ (LC/MS) |
| 27 | 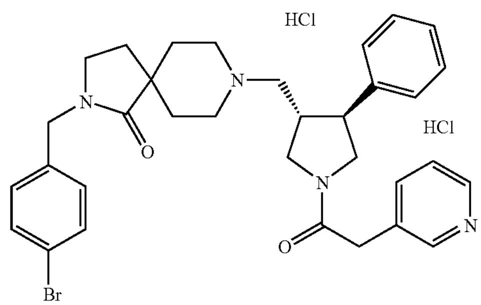 | 2-(4-Bromobenzyl)-8-[4-(SR)-phenyl-1-(2-pyridin-3-yl-acetyl)-pyrrolidin-3-(RS)-ylmethyl]-2,8-diaza-spiro[4.5]decan-1-one dihydrochloride | 674.507 | 92.4% (LC/MS) |
| 28 | 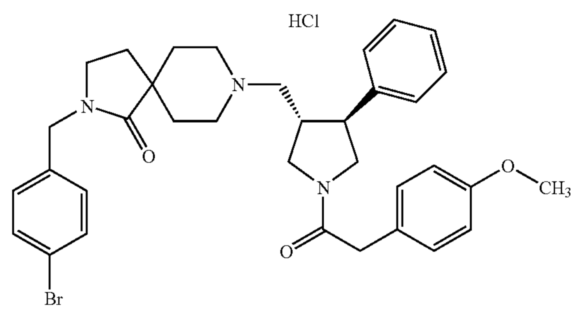 | 2-(4-Bromobenzyl)-8-{1-[2-(4-methoxyphenyl)-acetyl]-4-(SR)-phenyl-pyrrolidin-3-(RS)-ylmethyl}-2,8-diaza-spiro[4.5]decan-1-one hydrochloride | 667.084 | 98+ (LC/MS) |
| 29 | 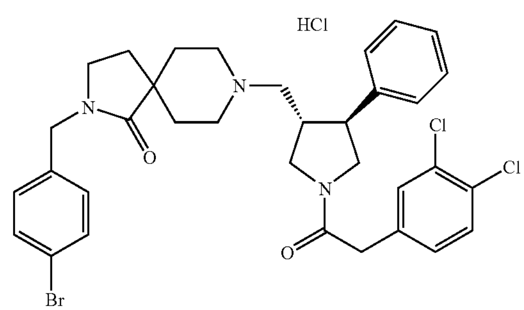 | 2-(4-Bromobenzyl)-8-{1-[2-(3,4-dichlorophenyl)-acetyl]-4-(SR)-phenyl-pyrrolidin-3-(RS)-ylmethyl}-2,8-diaza-spiro[4.5]decan-1-one hydrochloride | 705.948 | 95+ (LC/MS) |
| 30 | 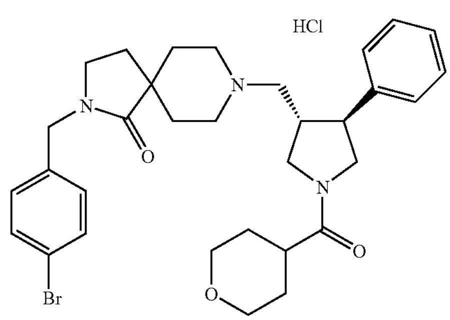 | 2-(4-Bromobenzyl)-8-[4-(SR)-phenyl-1-(tetrahydro-pyran-4-carbonyl)-pyrrolidin-3-(RS)-ylmethyl]-2,8-diaza-spiro[4.5]decan-1-one hydrochloride | 631.051 | 90+ (LC/MS) |

TABLE 1-continued

| CPD # | STRUCTURE | COMPOUND NAME | MOL WT | PURITY |
|---|---|---|---|---|
| 31 | 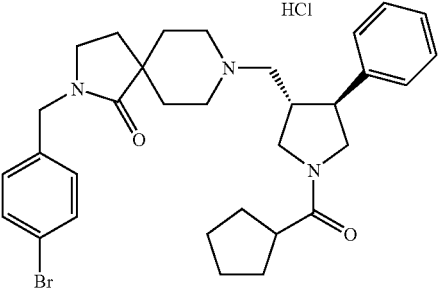 | 2-(4-Bromobenzyl)-8-(1-cyclopentanecarbonyl-4-(SR)-phenyl-pyrrolidin-3-(RS)-ylmethyl)-2,8-diaza-spiro[4.5]decan-1-one hydrochloride | 615.052 | 98+ (LC/MS) |
| 32 | 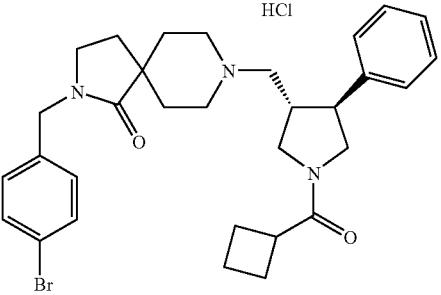 | 2-(4-Bromobenzyl)-8-(1-cyclobutanecarbonyl-4-(SR)-phenyl-pyrrolidin-3-(RS)-ylmethyl)-2,8-diaza-spiro[4.5]decan-1-one hydrochloride | 601.025 | 98+ (LC/MS) |
| 33 | 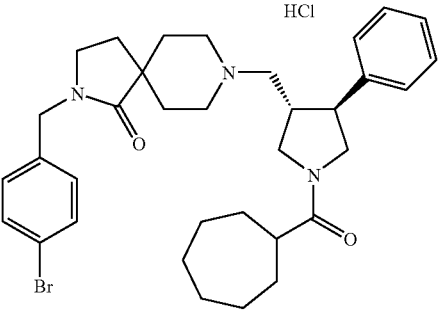 | 2-(4-Bromobenzyl)-8-(1-cycloheptanecarbonyl-4-(SR)-phenyl-pyrrolidin-3-(RS)-ylmethyl)-2,8-diaza-spiro[4.5]decan-1-one hydrochloride | 643.106 | 98+ (LC/MS) |
| 34 | 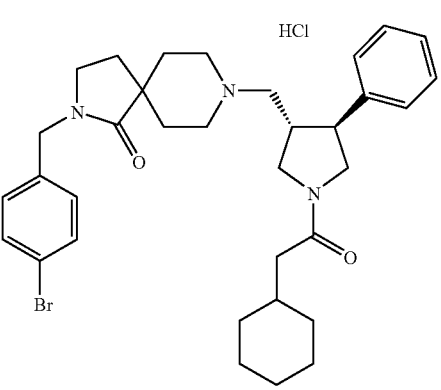 | 2-(4-Bromobenzyl)-8-[1-(2-cyclohexyl-acetyl)-4-(SR)-phenyl-pyrrolidin-3-(RS)-ylmethyl]-2,8-diaza-spiro[4.5]decan-1-one hydrochloride | 643.106 | 98+ (LC/MS) |

TABLE 1-continued

| CPD # | STRUCTURE | COMPOUND NAME | MOL WT | PURITY |
|---|---|---|---|---|
| 35 | 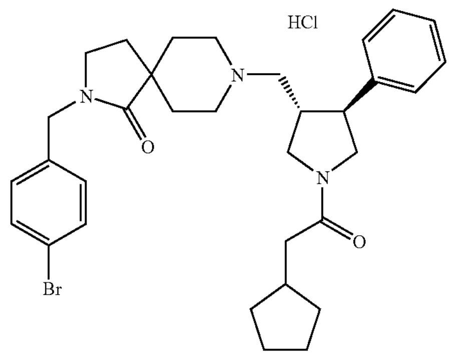 | 2-(4-Bromobenzyl)-8-[1-(2-cyclopentyl-acetyl)-4-(SR)-phenyl-pyrrolidin-3-(RS)-ylmethyl]-2,8-diaza-spiro[4.5]decan-1-one hydrochloride | 629.079 | 98+ (LC/MS) |
| 36 | 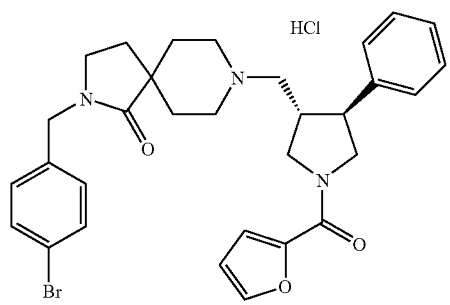 | 2-(4-Bromobenzyl)-8-[1-(furan-2-carbonyl)-4-(SR)-phenylpyrrolidin-3-(RS)-ylmethyl]-2,8-diaza-spiro[4.5]decan-1-one hydrochloride | 612.992 | 98+ (LC/MS) |
| 37 | 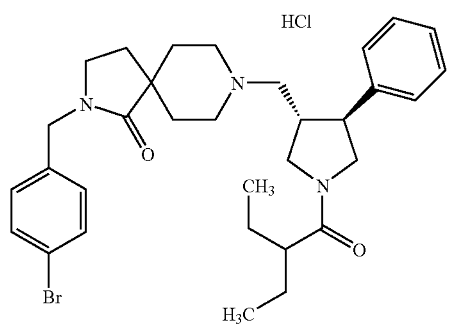 | 2-(4-Bromobenzyl)-8-[1-(2-ethyl-butyryl)-4-(SR)-phenylpyrrolidin-3-(RS)-ylmethyl]-2,8-diaza-spiro[4.5]decan-1-one hydrochloride | 617.068 | 98+ (LC/MS) |
| 38 | 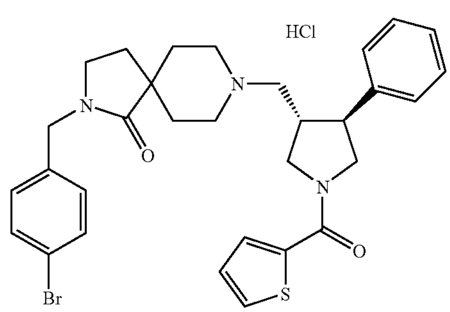 | 2-(4-Bromobenzyl)-8-[4-(SR)-phenyl-1-(thiophene-2-carbonyl)-pyrrolidin-3-(RS)-ylmethyl]-2,8-diaza-spiro[4.5]decan-1-one hydrochloride | 629.06 | 98+ (LC/MS) |

TABLE 1-continued

| CPD # | STRUCTURE | COMPOUND NAME | MOL WT | PURITY |
|---|---|---|---|---|
| 39 | 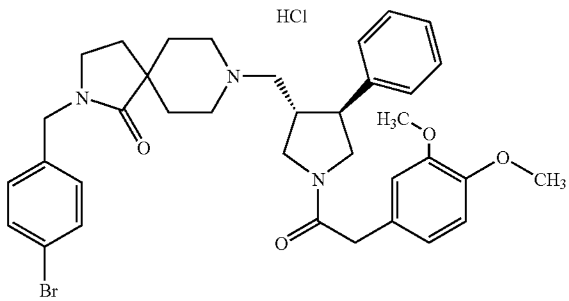 | 2-(4-Bromobenzyl)-8-{1-[2-(3,4-dimethoxyphenyl)-acetyl]-4-(SR)-phenyl-pyrrolidin-3-(RS)-ylmethyl}-2,8-diaza-spiro[4.5]decan-1-one hydrochloride | 697.11 | 98+ (LC/MS) |
| 40 | 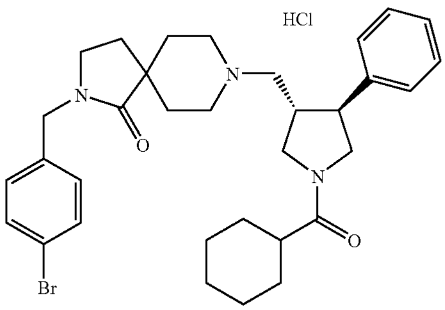 | 2-(4-Bromobenzyl)-8-(1-cyclohexanecarbonyl-4-(SR)-phenyl-pyrrolidin-3-(RS)-ylmethyl)-2,8-diaza-spiro[4.5]decan-1-one hydrochloride | 629.079 | 98+ (LC/MS) |
| 41 | 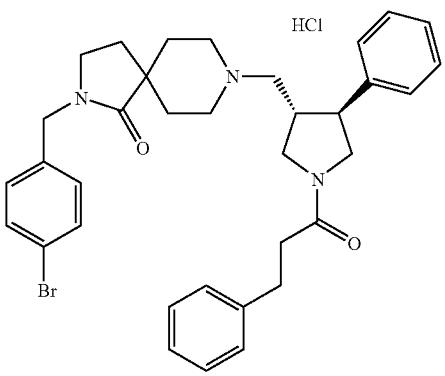 | 2-(4-Bromobenzyl)-8-[4-(SR)-phenyl-1-(3-phenyl-propionyl)-pyrrolidin-3-(RS)-ylmethyl]-2,8-diaza-spiro[4.5]decan-1-one hydrochloride | 651.085 | 98+ (LC/MS) |
| 42 | 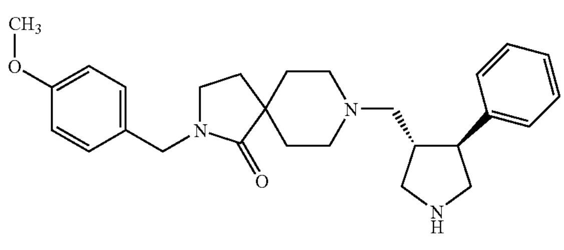 | 2-(4-Methoxybenzyl)-8-(4-(SR)-phenyl-pyrrolidin-3-(RS)-ylmethyl)-2,8-diaza-spiro[4.5]decan-1-one | 433.592 | >95% (1H NMR) |
| 43 | 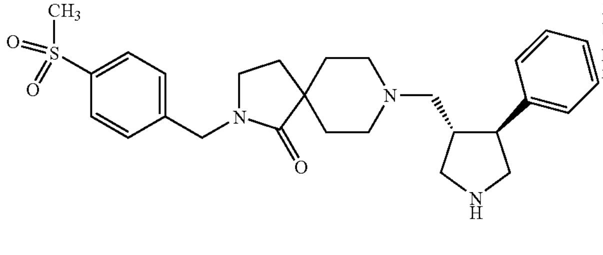 | 2-(4-Methanesulfonyl-benzyl)-8-(4-(SR)-phenyl-pyrrolidin-3-(RS)-yl-methyl)-2,8-diaza-spiro[4.5]decan-1-one | 481.658 | >95% (1H NMR) |

TABLE 1-continued

| CPD # | STRUCTURE | COMPOUND NAME | MOL WT | PURITY |
|---|---|---|---|---|
| 44 | 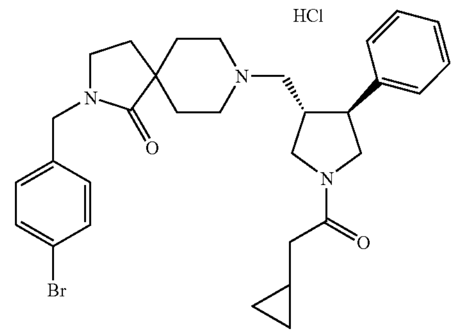 | 2-(4-Bromobenzyl)-8-[1-(2-cyclo-propyl-acetyl)-4-(SR)-phenyl-pyrrolidin-3-(RS)-ylmethyl]-2,8-di-aza-spiro[4.5]decan-1-one hydrochloride | 601.025 | 98+ (LC/MS) |
| 45 | 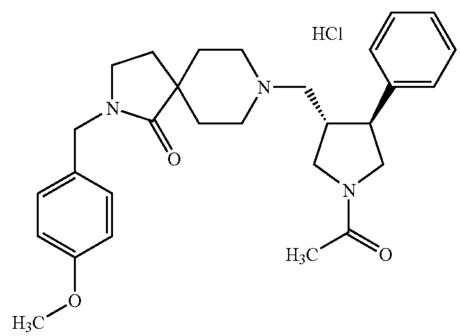 | 8-(1-Acetyl-4-(SR)-phenyl-pyrrolidin-3-(RS)-ylmethyl)-2-(4-methoxybenzyl)-2,8-diaza-spiro[4.5]decan-1-one hydrochloride | 512.09 | 98+ (LC/MS) |
| 46 | 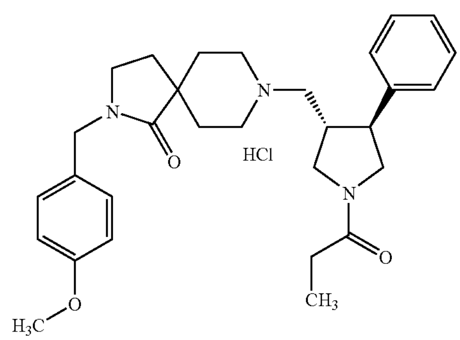 | 2-(4-Methoxybenzyl)-8-(4-(SR)-phenyl-1-propionyl-pyrrolidin-3-(RS)-ylmethyl)-2,8-diaza-spiro[4.5]decan-1-one hydrochloride | 526.117 | 98+ (LC/MS) |
| 47 | 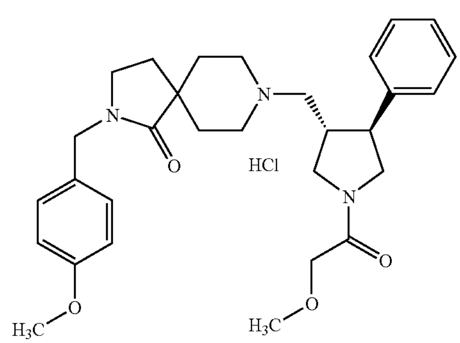 | 8-[1-(2-Methoxy-acetyl)-4-(SR)-phenyl-pyrrolidin-3-(RS)-ylmethyl]-2-(4-methoxybenzyl)-2,8-diaza-spiro[4.5]decan-1-one hydrochloride | 542.116 | 98+ (LC/MS) |

TABLE 1-continued

| CPD # | STRUCTURE | COMPOUND NAME | MOL WT | PURITY |
|---|---|---|---|---|
| 48 | 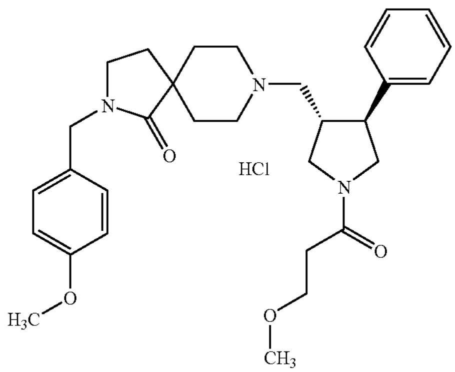 | 2-(4-Methoxybenzyl)-8-[1-(3-methoxypropionyl)-4-(SR)-phenyl-pyrrolidin-3-(RS)-ylmethyl]-2,8-diaza-spiro[4.5]decan-1-one hydrochloride | 556.143 | 98+ (LC/MS) |
| 49 | 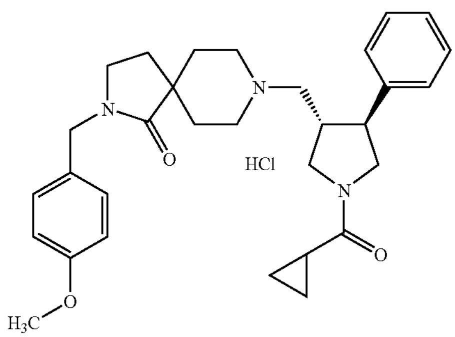 | 8-(1-Cyclopropanecarbonyl-4-(SR)-phenyl-pyrrolidin-3-(RS)-ylmethyl)-2-(4-methoxy-benzyl)-2,8-diaza-spiro[4.5]decan-1-one hydrochloride | 538.128 | 98+ (LC/MS) |
| 50 | 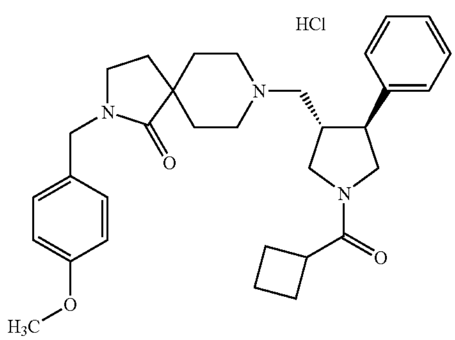 | 8-(1-Cyclobutanecarbonyl-4-(SR)-phenyl-pyrrolidin-3-(RS)-ylmethyl)-2-(4-methoxybenzyl)-2,8-diaza-spiro[4.5]decan-1-one hydrochloride | 552.155 | 98+ (LC/MS) |
| 51 | 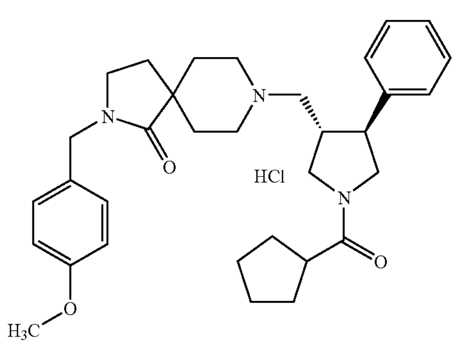 | 8-(1-Cyclopentanecarbonyl-4-(SR)-phenyl-pyrrolidin-3-(RS)-ylmethyl)-2-(4-methoxybenzyl)-2,8-diaza-spiro[4.5]decan-1-one hydrochloride | 566.182 | 98+ (LC/MS) |

TABLE 1-continued

| CPD # | STRUCTURE | COMPOUND NAME | MOL WT | PURITY |
|---|---|---|---|---|
| 52 | 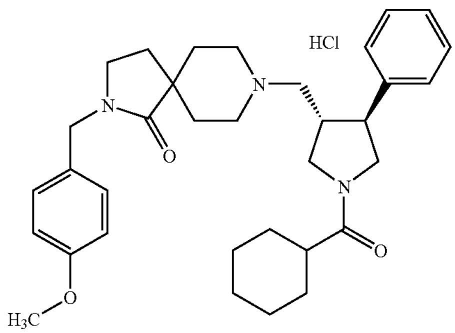 | 8-(1-Cyclohexanecarbonyl-4-(SR)-phenyl-pyrrolidin-3-(RS)-ylmethyl)-2-(4-methoxybenzyl)-2,8-diaza-spiro[4.5]decan-1-one hydrochloride | 580.208 | 98+ (LC/MS) |
| 53 | 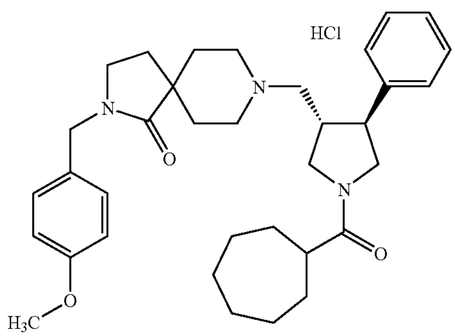 | 8-(1-Cycloheptanecarbonyl-4-(SR)-phenyl-pyrrolidin-3-(RS)-ylmethyl)-2-(4-methoxybenzyl)-2,8-diaza-spiro[4.5]decan-1-one hydrochloride | 594.235 | 98+ (LC/MS) |
| 54 | 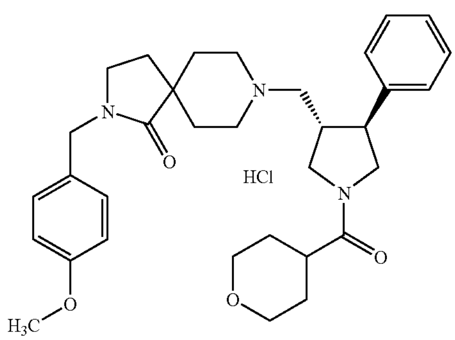 | 2-(4-Methoxybenzyl)-8-[4-(SR)-phenyl-1-(tetrahydro-pyran-4-carbonyl)-pyrrolidin-3-(RS)-ylmethyl]-2,8-diaza-spiro[4.5]decan-1-one hydrochloride | 582.181 | 98+ (LC/MS) |
| 55 | 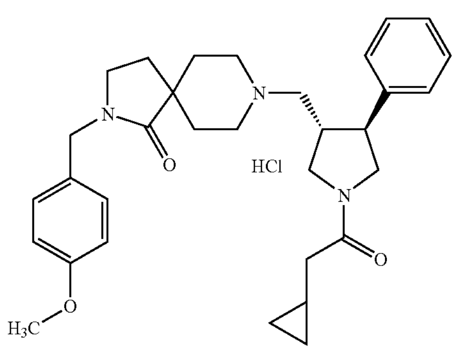 | 8-[1-(2-Cyclopropyl-acetyl)-4-(SR)-phenyl-pyrrolidin-3-(RS)-ylmethyl]-2-(4-methoxybenzyl)-2,8-diaza-spiro[4.5]decan-1-one hydrochloride | 552.155 | 98+ (LC/MS) |

TABLE 1-continued

| CPD # | STRUCTURE | COMPOUND NAME | MOL WT | PURITY |
|---|---|---|---|---|
| 56 | 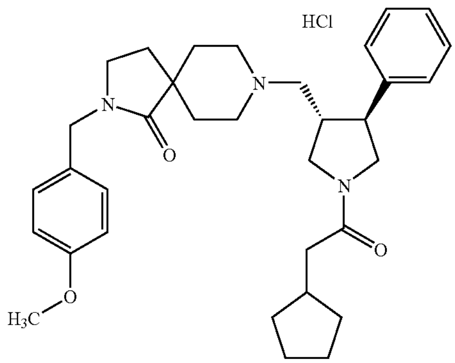 | 8-[1-(2-Cyclopentyl-acetyl)-4-(SR)-phenyl-pyrrolidin-3-(RS)-ylmethyl]-2-(4-methoxybenzyl)-2,8-diaza-spiro[4.5]decan-1-one hydrochloride | 580.208 | 98+ (LC/MS) |
| 57 | 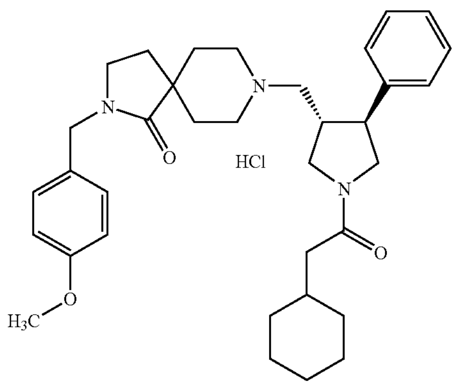 | 8-[1-(2-Cyclohexyl-acetyl)-4-(SR)-phenyl-pyrrolidin-3-(RS)-ylmethyl]-2-(4-methoxybenzyl)-2,8-diaza-spiro[4.5]decan-1-one hydrochloride | 594.235 | 98+ (LC/MS) |
| 58 | 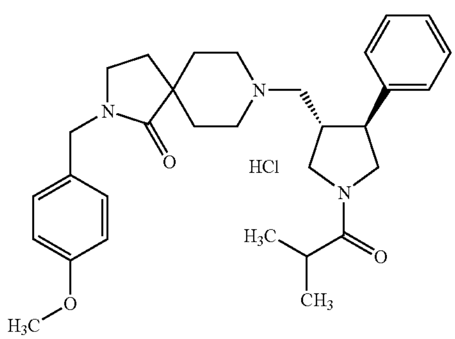 | 8-(1-Isobutyryl-4-(SR)-phenyl-pyrrolidin-3-(RS)-ylmethyl)-2-(4-methoxybenzyl)-2,8-diaza-spiro[4.5]decan-1-one hydrochloride | 540.144 | 98+ (LC/MS) |
| 59 | 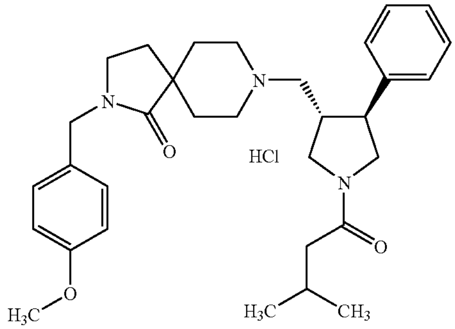 | 2-(4-Methoxybenzyl)-8-[1-(3-methyl-butyryl)-4-(SR)-phenyl-pyrrolidin-3-(RS)-ylmethyl]-2,8-diaza-spiro[4.5]decan-1-one hydrochloride | 554.171 | 98+ (LC/MS) |

TABLE 1-continued

| CPD # | STRUCTURE | COMPOUND NAME | MOL WT | PURITY |
|---|---|---|---|---|
| 60 | 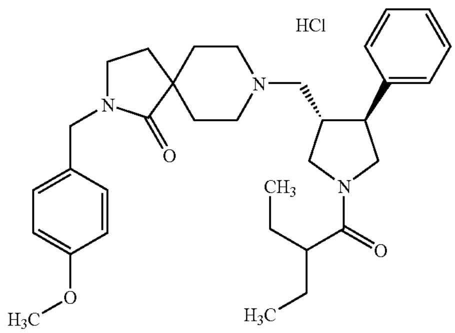 | 8-[1-(2-Ethyl-butyryl)-4-(SR)-phenyl-pyrrolidin-3-(RS)-ylmethyl]-2-(4-methoxybenzyl)-2,8-diaza-spiro[4.5]decan-1-one hydrochloride | 568.197 | 98+ (LC/MS) |
| 61 | 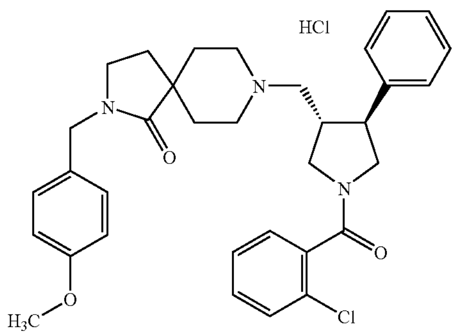 | 8-[1-(2-Chlorobenzoyl)-4-(SR)-phenyl-pyrrolidin-3-(RS)-ylmethyl]-2-(4-methoxybenzyl)-2,8-diaza-spiro[4.5]decan-1-one hydrochloride | 608.606 | 98+ (LC/MS) |
| 62 | 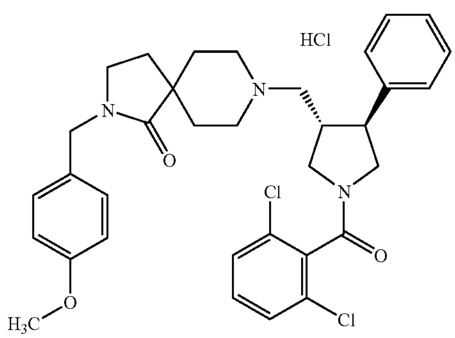 | 8-[1-(2,6-Dichlorobenzoyl)-4-(SR)-phenyl-pyrrolidin-3-(RS)-ylmethyl]-2-(4-methoxybenzyl)-2,8-diaza-spiro[4.5]decan-1-one hydrochloride | 643.051 | 98+ (LC/MS) |
| 63 | 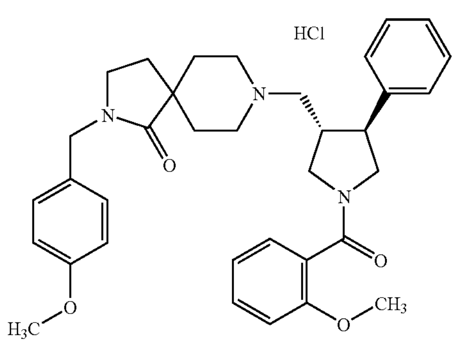 | 8-[1-(2-Methoxybenzoyl)-4-(SR)-phenyl-pyrrolidin-3-(RS)-ylmethyl]-2-(4-methoxybenzyl)-2,8-diaza-spiro[4.5]decan-1-one hydrochloride | 604.187 | 98+ (LC/MS) |

TABLE 1-continued

| CPD # | STRUCTURE | COMPOUND NAME | MOL WT | PURITY |
|---|---|---|---|---|
| 64 | 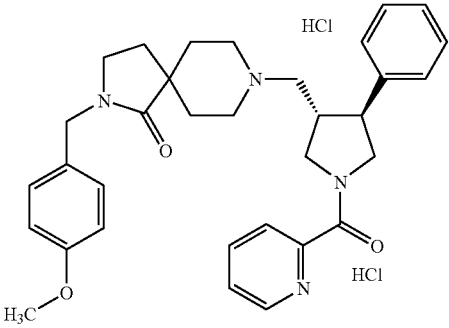 | 2-(4-Methoxybenzyl)-8-[4-(SR)-phenyl-1-(pyridine-2-carbonyl)-pyrrolidin-3-(RS)-ylmethyl]-2,8-diaza-spiro[4.5]decan-1-one dihydrochloride | 611.61 | 98+ (LC/MS) |
| 65 | 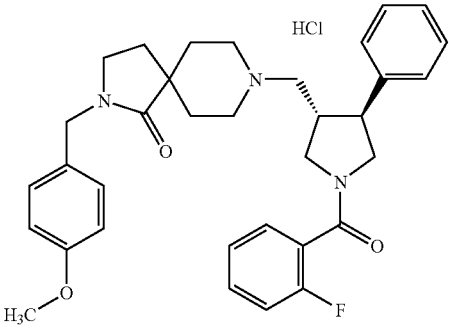 | 8-[1-(2-Fluorobenzoyl)-4-(SR)-phenyl-pyrrolidin-3-(RS)-ylmethyl]-2-(4-methoxybenzyl)-2,8-diaza-spiro[4.5]decan-1-one hydrochloride | 592.151 | 98+ (LC/MS) |
| 66 | 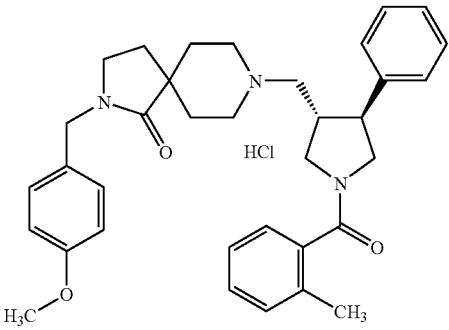 | 2-(4-Methoxybenzyl)-8-[1-(2-methylbenzoyl)-4-(SR)-phenyl-pyrrolidin-3-(RS)-ylmethyl]-2,8-diaza-spiro[4.5]decan-1-one hydrochloride | 588.188 | 98+ (LC/MS) |
| 67 | 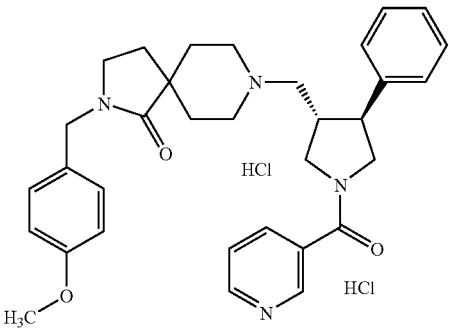 | 2-(4-Methoxybenzyl)-8-[4-(SR)-phenyl-1-(pyridine-3-carbonyl)-pyrrolidin-3-(RS)-ylmethyl]-2,8-diaza-spiro[4.5]decan-1-one dihydrochloride | 611.61 | 98+ (LC/MS) |

TABLE 1-continued

| CPD # | STRUCTURE | COMPOUND NAME | MOL WT | PURITY |
|---|---|---|---|---|
| 68 | 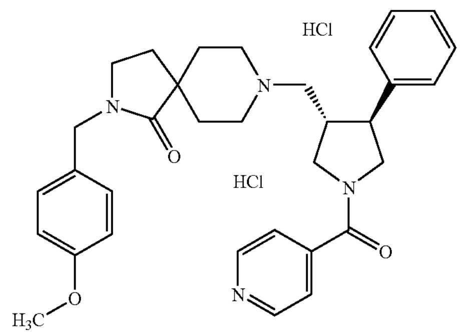 | 2-(4-Methoxybenzyl)-8-[4-(SR)-phenyl-1-(pyridine-4-carbonyl)-pyrrolidin-3-(RS)-ylmethyl]-2,8-diaza-spiro[4.5]decan-1-one dihydrochloride | 611.61 | 98+ (LC/MS) |
| 69 | 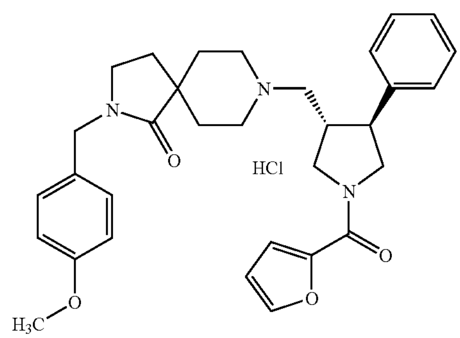 | 8-[1-(Furan-2-carbonyl)-4-(SR)-phenyl-pyrrolidin-3-(RS)-ylmethyl]-2-(4-methoxybenzyl)-2,8-diaza-spiro[4.5]decan-1-one hydrochloride | 564.122 | 98+ (LC/MS) |
| 70 | 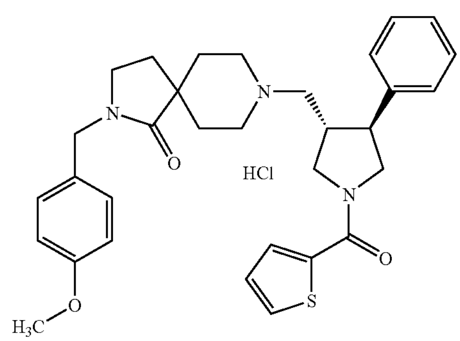 | 2-(4-Methoxybenzyl)-8-[4-(SR)-phenyl-1-(thiophene-2-carbonyl)-pyrrolidin-3-(RS)-ylmethyl]-2,8-diaza-spiro[4.5]decan-1-one hydrochloride | 580.189 | 98+ (LC/MS) |
| 71 | 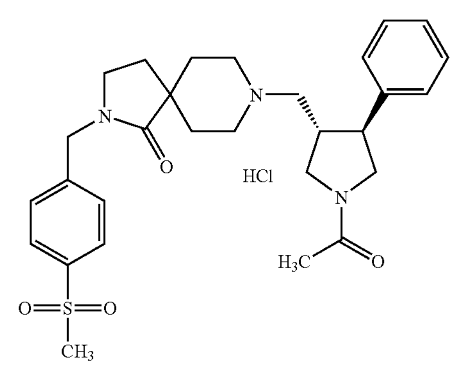 | 8-(1-Acetyl-4-(SR)-phenyl-pyrrolidin-3-(RS)-ylmethyl]-2-(4-methanesulfonylbenzyl)-2,8-diaza-spiro[4.5]decan-1-one hydrochloride | 560.155 | 98+ (LC/MS) |

TABLE 1-continued

| CPD # | STRUCTURE | COMPOUND NAME | MOL WT | PURITY |
|---|---|---|---|---|
| 72 | 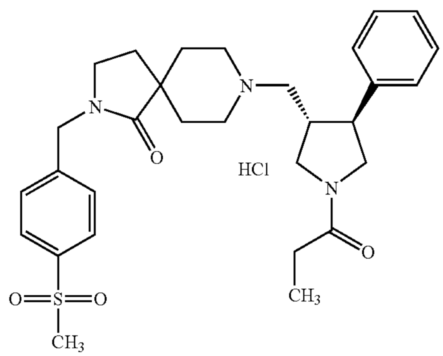 | 2-(4-Methanesulfonylbenzyl)-8-(4-(SR)-phenyl-1-propionyl-pyrrolidin-3-(RS)-ylmethyl)-2,8-diaza-spiro[4.5]decan-1-one hydrochloride | 574.182 | 98+ (LC/MS) |
| 73 | 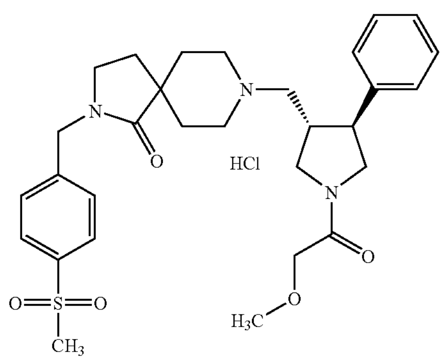 | 2-(4-Methanesulfonylbenzyl)-8-[1-(2-methoxy-acetyl)-4-(SR)-phenyl-pyrrolidin-3-(RS)-ylmethyl]-2,8-diaza-spiro[4.5]decan-1-one hydrochloride | 590.181 | 98+ (LC/MS) |
| 74 | 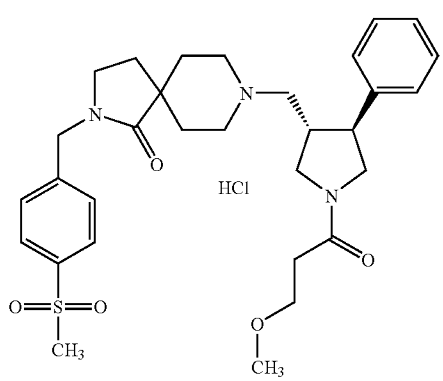 | 2-(4-Methanesulfonylbenzyl)-8-[1-(3-methoxy-propionyl)-4-(SR)-phenyl-pyrrolidin-3-(RS)-ylmethyl]-2,8-diaza-spiro[4.5]decan-1-one hydrochloride | 604.208 | 98+ (LC/MS) |
| 75 | 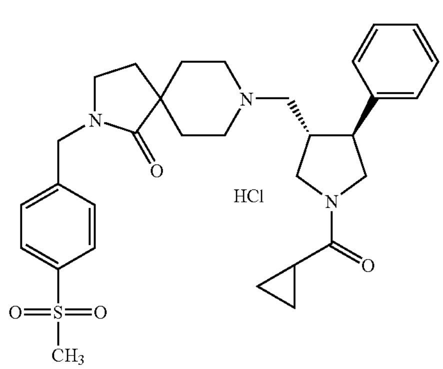 | 8-(1-Cyclopropanecarbonyl-4-(SR)-phenyl-pyrrolidin-3-(RS)-ylmethyl)-2-(4-methanesulfonylbenzyl)-2,8-diaza-spiro[45]decan-1-one hydrochloride | 586.193 | 95+ (LC/MS) |

TABLE 1-continued

| CPD # | STRUCTURE | COMPOUND NAME | MOL WT | PURITY |
|---|---|---|---|---|
| 76 | 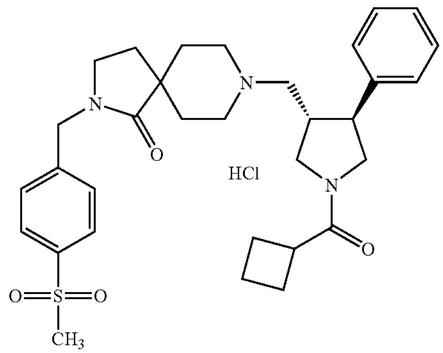 | 8-(1-Cyclobutanecarbonyl-4-(SR)-phenyl-pyrrolidin-3-(RS)-ylmethyl)-2-(4-methanesulfonylbenzyl)-2,8-diaza-spiro[4.5]decan-1-one hydrochloride | 600.22 | 98+ (LC/MS) |
| 77 | 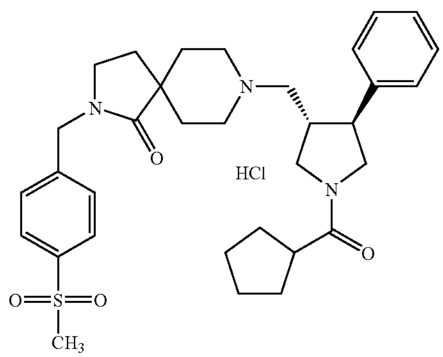 | 8-(1-Cyclopentanecarbonyl-4-(SR)-phenyl-pyrrolidin-3-(RS)-ylmethyl)-2-(4-methanesulfonylbenzyl)-2,8-diaza-spiro[4.5]decan-1-one hydrochloride | 614.247 | 98+ (LC/MS) |
| 78 | 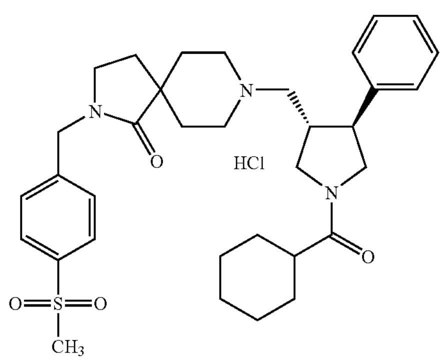 | 8-(1-Cyclohexanecarbonyl-4-(SR)-phenyl-pyrrolidin-3-(RS)-ylmethyl)-2-(4-methanesulfonylbenzyl)-2,8-diaza-spiro[4.5]decan-1-one hydrochloride | 628.273 | 98+ (LC/MS) |
| 79 | 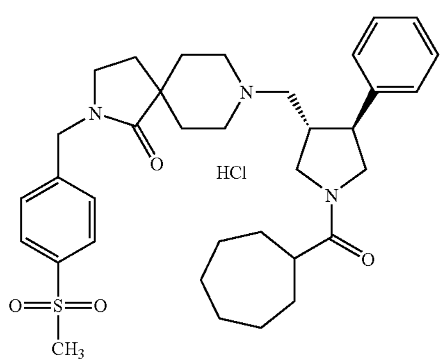 | 8-(1-Cycloheptanecarbonyl-4-(SR)-phenyl-pyrrolidin-3-(RS)-ylmethyl)-2-(4-methanesulfonylbenzyl)-2,8-diaza-spiro[4.5]decan-1-one hydrochloride | 642.3 | 98+ (LC/MS) |

TABLE 1-continued

| CPD # | STRUCTURE | COMPOUND NAME | MOL WT | PURITY |
|---|---|---|---|---|
| 80 | 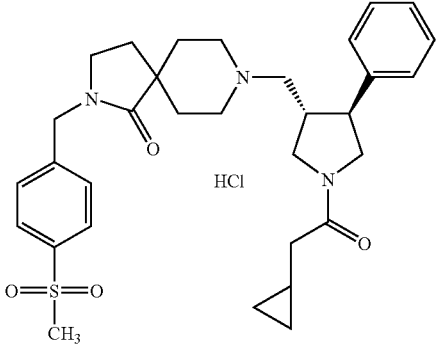 | 8-[1-(2-Cyclopropyl-acetyl)-4-(SR)-phenyl-pyrrolidin-3-(RS)-ylmethyl]-2-(4-methanesulfonylbenzyl)-2,8-diaza-spiro[4.5]decan-1-one hydrochloride | 600.22 | 98+ (LC/MS) |
| 81 | 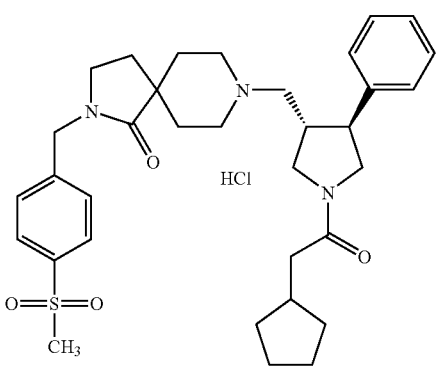 | 8-[1-(2-Cyclopentyl-acetyl)-4-(SR)-phenyl-pyrrolidin-3-(RS)-ylmethyl]-2-(4-methanesulfonylbenzyl)-2,8-diaza-spiro[4.5]decan-1-one hydrochloride | 628.273 | 98+ (LC/MS) |
| 82 | 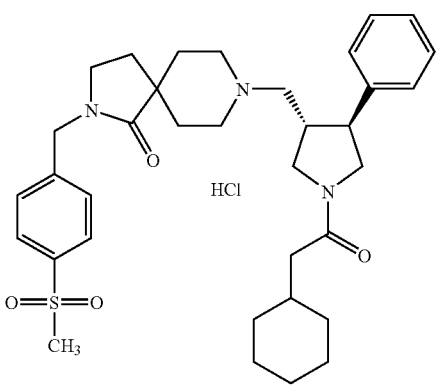 | 8-[1-(2-Cyclohexyl-acetyl)-4-(SR)-phenyl-pyrrolidin-3-(RS)-ylmethyl]-2-(4-methanesulfonylbenzyl)-2,8-diaza-spiro[4.5]decan-1-one hydrochloride | 642.3 | 98+ (LC/MS) |
| 83 | 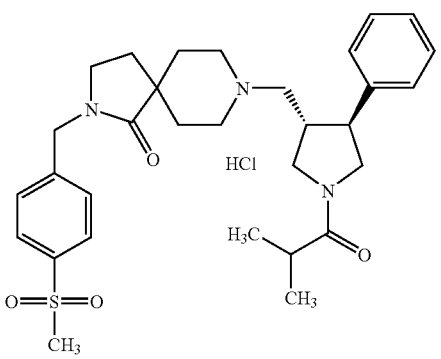 | 8-(1-Isobutyryl-4-(SR)-phenyl-pyrrolidin-3-(RS)-ylmethyl]-2-(4-methanesulfonylbenzyl)-2,8-diaza-spiro[4.5]decan-1-one hydrochloride | 588.209 | 98+ (LC/MS) |

TABLE 1-continued

| CPD # | STRUCTURE | COMPOUND NAME | MOL WT | PURITY |
|---|---|---|---|---|
| 84 | 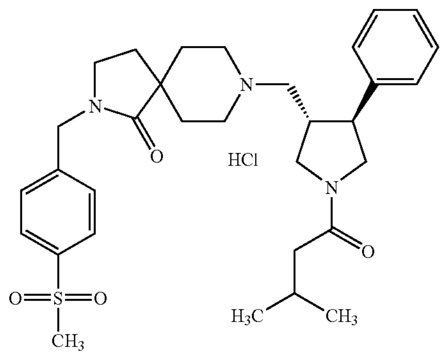 | 2-(4-Methanesulfonylbenzyl)-8-[1-(3-methyl-butyryl)-4-(SR)-phenyl-pyrrolidin-3-(RS)-ylmethyl]-2,8-di-aza-spiro[4.5]decan-1-one hydrochloride | 602.236 | 98+ (LC/MS) |
| 85 | 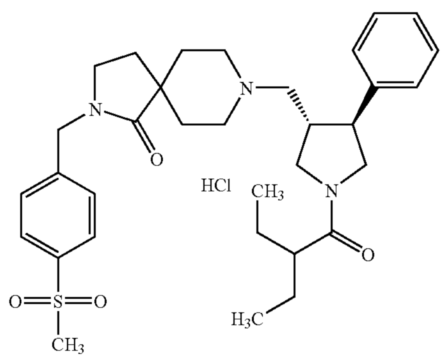 | 8-[1-(2-Ethyl-butyryl)-4-(SR)-phenyl-pyrrolidin-3-(RS)-ylmethyl]-2-(4-methanesulfonylbenzyl)-2,8-di-aza-spiro[4.5]decan-1-one hydrochloride | 616.262 | 98+ (LC/MS) |
| 86 | 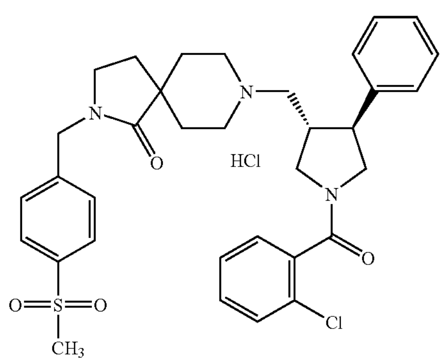 | 8-[1-(2-Chlorobenzoyl)-4-(SR)-phenyl-pyrrolidin-3-(RS)-ylmethyl]-2-(4-methanesulfonylbenzyl)-2,8-di-aza-spiro[4.5]decan-1-one hydrochloride | 656.671 | 98+ (LC/MS) |
| 87 | 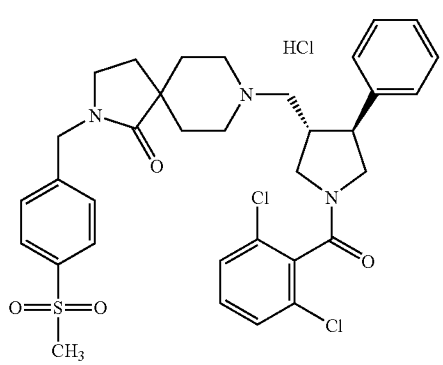 | 8-[1-(2,6-Dichlorobenzoyl)-4-(SR)-phenyl-pyrrolidin-3-(RS)-ylmethyl]-2-(4-methanesulfonylbenzyl)-2,8-di-aza-spiro[4.5]decan-1-one hydrochloride | 691.116 | 98+ (LC/MS) |

TABLE 1-continued

| CPD # | STRUCTURE | COMPOUND NAME | MOL WT | PURITY |
|---|---|---|---|---|
| 88 | 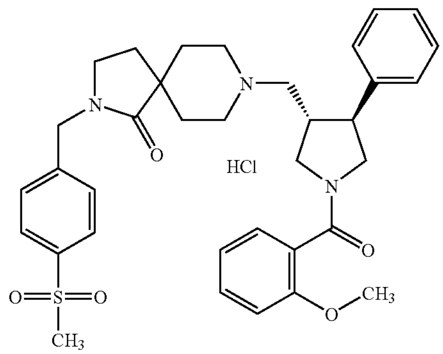 | 2-(4-Methanesulfonylbenzyl)-8-[1-(2-methoxybenzoyl)-4-(SR)-phenyl-pyrrolidin-3-(RS)-ylmethyl]-2,8-diaza-spiro[4.5]decan-1-one hydrochloride | 652.252 | 95+ (LC/MS) |
| 89 | 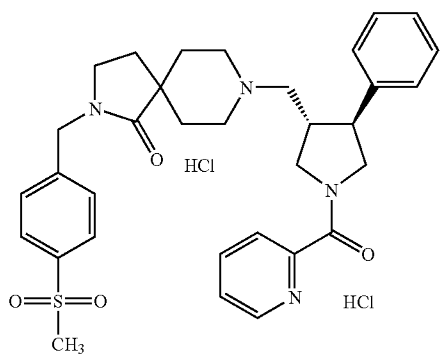 | 2-(4-Methanesulfonylbenzyl)-8-[4-(SR)-phenyl-1-(pyridine-2-carbonyl)-pyrrolidin-3-(RS)-ylmethyl]-2,8-diaza-spiro[4.5]decan-1-one dihydrochloride | 659.675 | 98+ (LC/MS) |
| 90 | 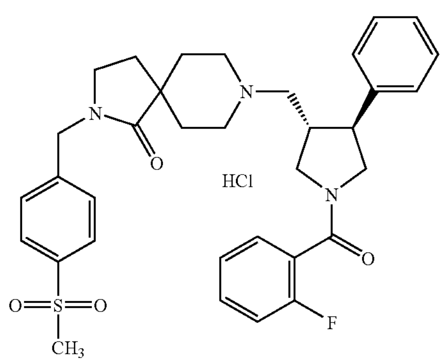 | 8-[1-(2-Fluorobenzoyl)-4-(SR)-phenyl-pyrrolidin-3-(RS)-ylmethyl]-2-(4-methanesulfonylbenzyl)-2,8-diaza-spiro[4.5]decan-1-one hydrochloride | 640.216 | 98+ (LC/MS) |
| 91 | 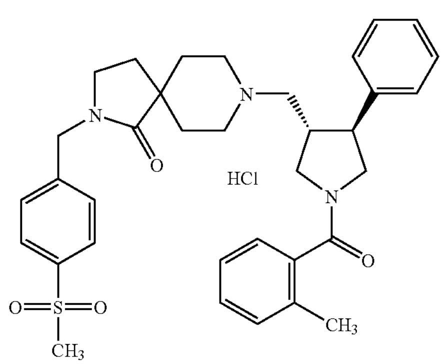 | 2-(4-Methanesulfonylbenzyl)-8-[1-(2-methylbenzoyl)-4-(SR)-phenyl-pyrrolidin-3-(RS)-ylmethyl]-2,8-diaza-spiro[4.5]decan-1-one hydrochloride | 636.253 | 98+ (LC/MS) |

TABLE 1-continued

| CPD # | STRUCTURE | COMPOUND NAME | MOL WT | PURITY |
|---|---|---|---|---|
| 92 | 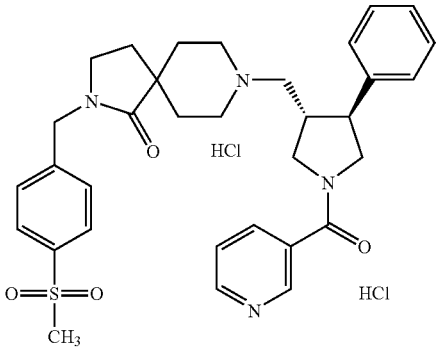 | 2-(4-Methanesulfonylbenzyl)-8-[4-(SR)-phenyl-1-(pyridine-3-carbonyl)-pyrrolidin-3-(RS)-ylmethyl]-2,8-diaza-spiro[4.5]decan-1-one dihydrochloride | 659.675 | 98+ (LC/MS) |
| 93 | 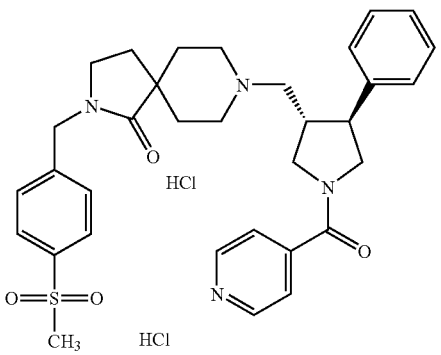 | 2-(4-Methanesulfonylbenzyl)-8-[4-(SR)-phenyl-1-(pyridine-4-carbonyl)-pyrrolidin-3-(RS)-ylmethyl]-2,8-diaza-spiro[4.5]decan-1-one dihydrochloride | 659.675 | 98+ (LC/MS) |
| 94 | 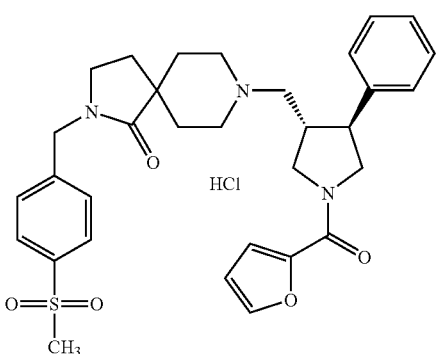 | 8-[1-(Furan-2-carbonyl)-4-(SR)-phenyl-pyrrolidin-3-(RS)-ylmethyl]-2-(4-methanesulfonylbenzyl)-2,8-diaza-spiro[4.5]decan-1-one hydrochloride | 612.187 | 98+ (LC/MS) |
| 95 | 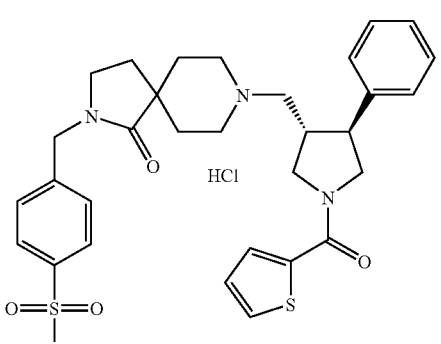 | 2-(4-Methanesulfonylbenzyl)-8-[4-(SR)-phenyl-1-(thiophene-2-carbonyl)-pyrrolidin-3-(RS)-ylmethyl]-2,8-diaza-spiro[4.5]decan-1-one hydrochloride | 628.254 | 98+ (LC/MS) |

Scheme 4

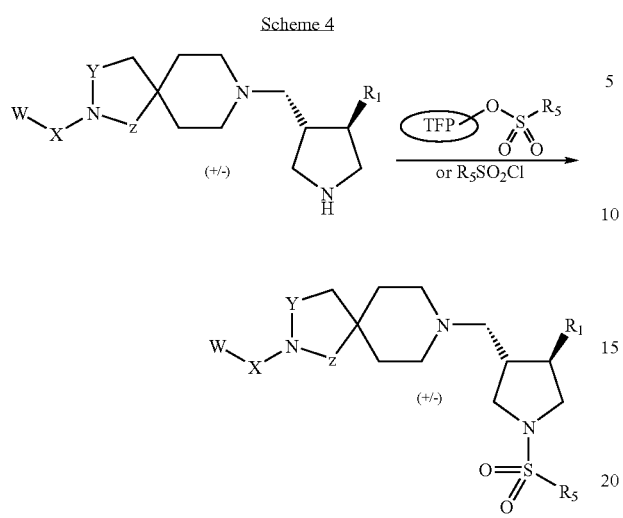

Example 4

8-(1-Benzenesulfonyl-4-(SR)-phenylpyrrolidin-3-(RS)-ylmethyl)-2-(4-bromobenzyl)-2,8-diaza-spiro[4.5]decan-1-one hydrochloride (Compound 96)

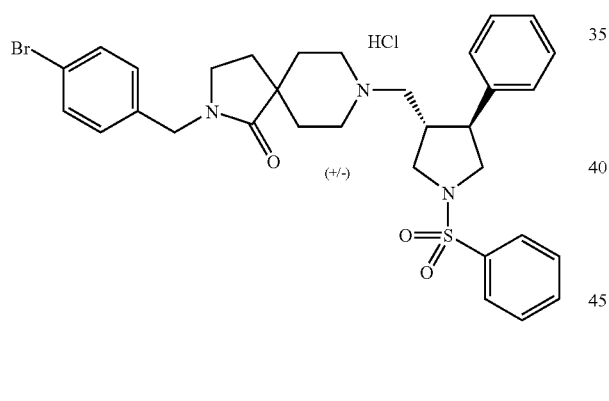

To 83 mg (100 µmol, loading of 1.2 mmol/g) of benzenesulfonate activated ester on polymeric 4-hydroxy-2,3,5,6-tetrafluorobenzamido (TFP) resin (see preparation in J. M. Salvino et al. *J. Comb. Chem.* 2000, 2, 691-697), preswollen with 0.5 mL of anhydrous DMF, was added 28.9 mg (60 µmol) of 2-(4-bromobenzyl)-8-(4-(SR)-phenylpyrrolidin-3-(RS)-ylmethyl)-2,8-diaza-spiro[4.5]decan-1-one diluted in 1 mL of DMF. The reaction was agitated overnight at room temperature. The mixture was filtered and washed with DCM (2×2 mL). The washes were collected and evaporated in vacuo. The crude was purified by semi-preparative HPLC (method A) yielding 16.7 mg (42.2%) of Compound 96 as a colorless solid.

$^1$H NMR (400 MHz, DMSO-d$_6$): δ [ppm] 9.19 (br s, 1H), 7.85 (d, 2H), 7.76 (txt, 1H), 7.67 (t, 2H), 7.51 (d, 2H), 7.32-7.14 (m, 5H), 7.13 (d, 2H), 4.32 (s, 2H), 3.85 (t, 1H), 3.68 (t, 1H), 3.46-3.27 (m, 2H), 3.20-2.64 (m, 10H), 1.96 (txd, 1H), 1.89 (t, 2H), 1.80 (t, 1H), 1.54 (br d, 2H).

LC/MS: m/z 624.0 (MH$^+$).

Scheme 5

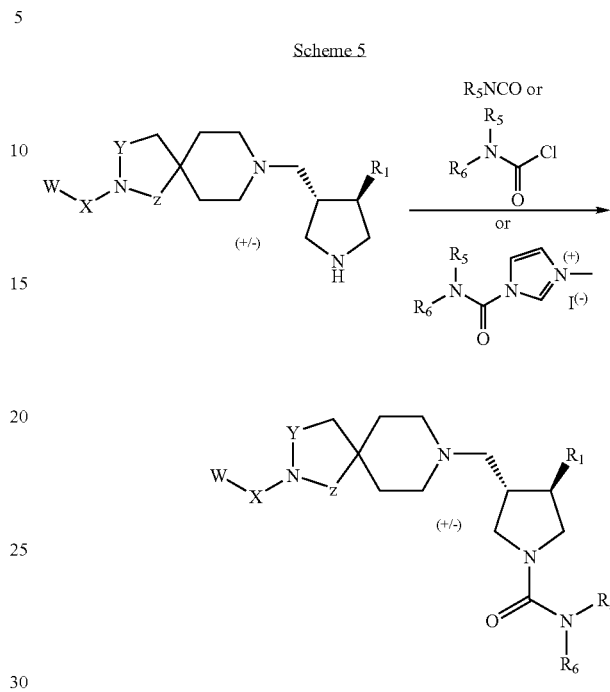

Example 5

3-(RS)-[2-(4-Bromobenzyl)-1-oxo-2,8-diaza-spiro[4.5]dec-8-ylmethyl]-4-(SR)-phenylpyrrolidine-1-carboxylic acid phenylamide hydrochloride (Compound 97)

To 28.9 mg (60 µmol) of 2-(4-bromobenzyl)-8-(4-(SR)-phenylpyrrolidin-3-(RS)-ylmethyl)-2,8-diaza-spiro[4.5]decan-1-one, diluted in 1 mL of anhydrous THF, were added 9.7 mg (80 µmol) of phenylisocyanate previously dissolved in 0.5 mL of anhydrous THF. The reaction mixture was agitated overnight at room temperature and evaporated in vacuo. The crude was purified by semi-preparative HPLC (method B) yielding 16.9 mg (44.1%) of Compound 97 as a pale yellow solid.

$^1$H NMR (400 MHz, DMSO-d$_6$): δ [ppm] 9.36 (br s, 1H), 8.18 (s, 1H), 7.51 (m, 4H), 7.40 (m, 4H), 7.30 (m, 1H), 7.22 (t, 2H), 7.14 (d, 2H), 6.92 (t, 1H), 4.34 (s, 2H), 4.08 (m, 1H), 3.91 (br t, 1H), 3.57 (br d, 1H), 3.37-3.14 (m, 8H), 3.07-2.79 (m, 3H), 2.06-1.83 (m, 4H), 1.58 (br d, 2H).

LC/MS: m/z 601.2 (MH$^+$).

Example 6

8-(1-Benzyl-4-(SR)-phenylpyrrolidin-3-(RS)-ylmethyl)-2-(4-bromobenzyl)-2,8-diaza-spiro[4.5]decan-1-one dihydrochloride (Compound 98)

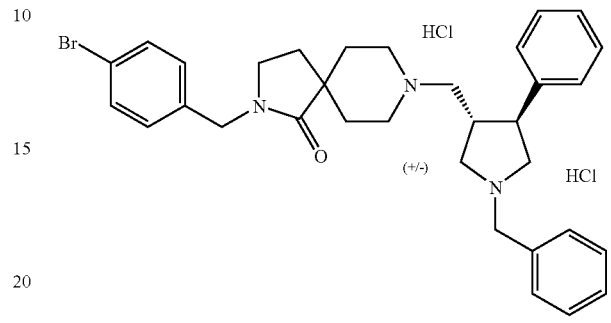

Scheme 6

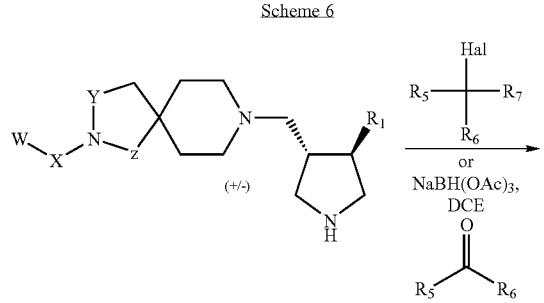

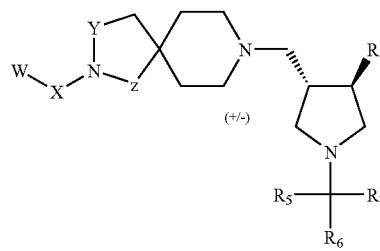

A solution of 28.9 mg (60 μmol) of 2-(4-bromobenzyl)-8-(4-(SR)-phenylpyrrolidin-3-(RS)-ylmethyl)-2,8-diaza-spiro[4.5]decan-1-one and 6.3 mg (60 μmol) of benzaldehyde in 1.5 mL of DCE was agitated for 10 minutes at room temperature before adding 20 mg (90 μmol) of triacetoxyborohydride. The reaction mixture was then stirred overnight and quenched with a saturated solution of sodium bicarbonate (1 mL). The solution was extracted with DCM (2×2 mL) and the combined organic layers were concentrated. The crude was purified by semi-preparative HPLC (method B) yielding 15.3 mg (39.5%) of Compound 98 as a pale yellow solid.

$^1$H NMR (400 MHz, DMSO-d$_6$): δ [ppm] 10.4 (br s, 1H), 9.6 (br s, 1H), 7.65 (m, 2H), 7.53-7.29 (m, 10H), 7.13 (m, 2H), 4.45 (m, 2H), 4.32 (s, 2H), 3.68 (m, 2H), 3.53 (m, 1H), 3.4-2.97 (m, 10H), 2.70 (m, 1H), 2.00-1.80 (m, 4H), 1.55 (br d, 2H).

LC/MS: m/z 572.2 (MH$^+$).

Table 2 of compounds illustrates some of the compounds of the present invention which were synthesized using the procedures described in schemes 4, 5 and 6.

TABLE 2

| CPD # | STRUCTURE | COMPOUND NAME | MOL WT | PURITY |
|---|---|---|---|---|
| 96 | 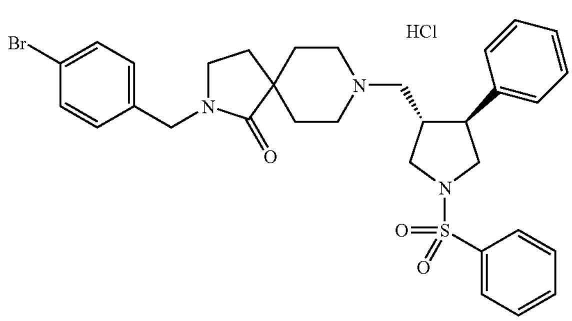 | 8-(1-Benzenesulfonyl-4-(SR)-phenyl-pyrrolidin-3-((RS)-yl-methyl)-2-(4-bromobenzyl)-2,8-di-aza-spiro[4.5]decan-1-one hydrochloride | 659.09 | 95% (1H NMR) |

TABLE 2-continued

| CPD # | STRUCTURE | COMPOUND NAME | MOL WT | PURITY |
|---|---|---|---|---|
| 97 | 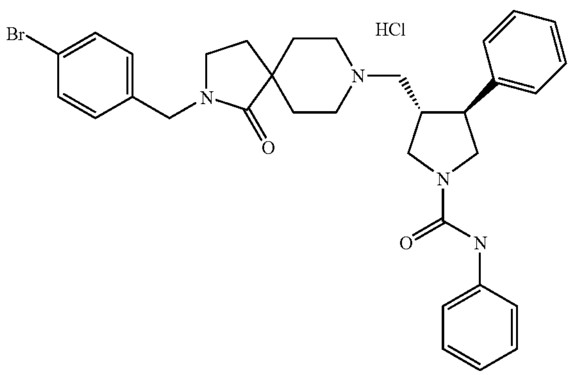 | 3-((RS)-[2-(4-Bromobenzyl)-1-oxo-2,8-di-aza-spiro[4.5]dec-8-yl-methyl]-4-(SR)-phenyl-pyrrolidine-1-carboxylic acid phenylamide hydrochloride | 638.05 | 94% (LC/MS) |
| 98 | 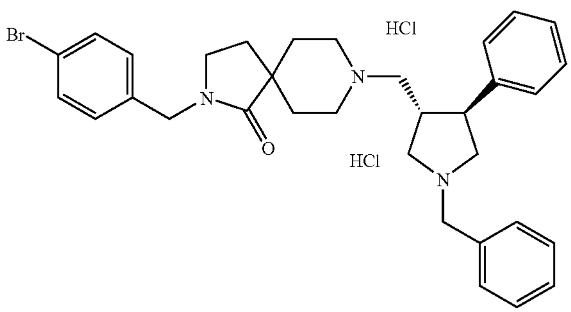 | 8-(1-Benzyl-4-(SR)-phenyl-pyrrolidin-3-((RS)-yl-methyl)-2-(4-bromobenzyl)-2,8-di-aza-spiro[4.5]decan-1-one dihydrochloride | 645.51 | 98% (LC/MS) |
| 99 | 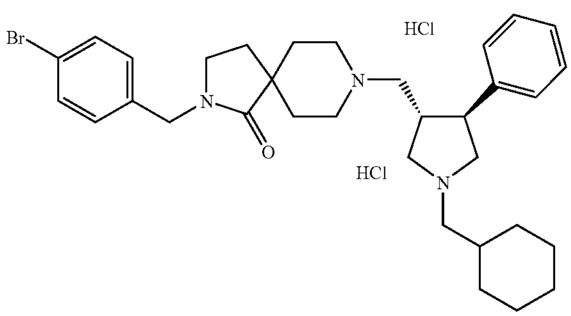 | 2-(4-Bromobenzyl)-8-(1-cyclohexylmethyl-4-(SR)-phenyl-pyrrolidin-3-((RS)-yl-methyl)-2,8-diaza-spiro[4.5]decan-1-one dihydrochloride | 651.56 | 98% (LC/MS) |

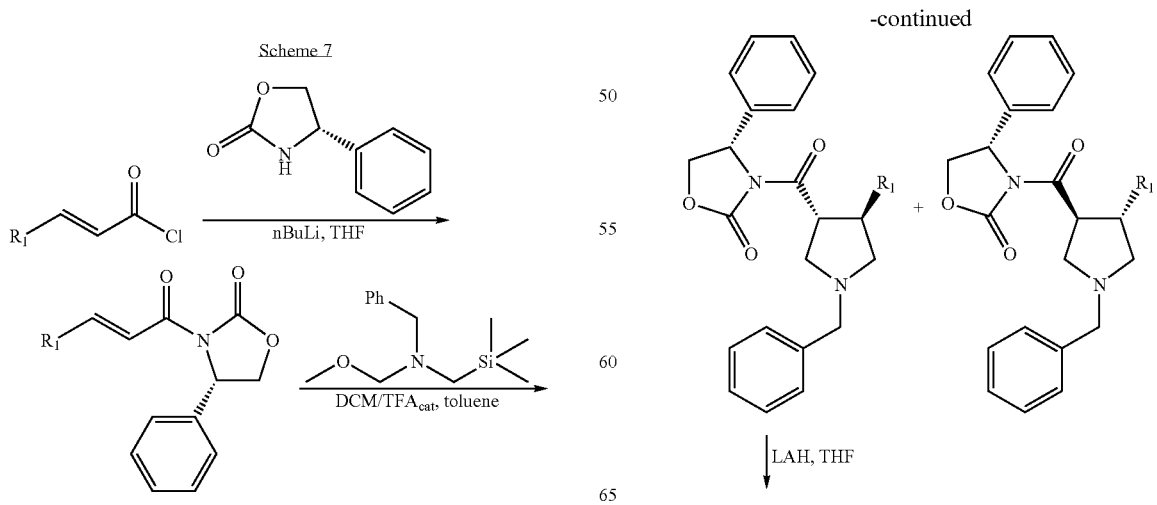

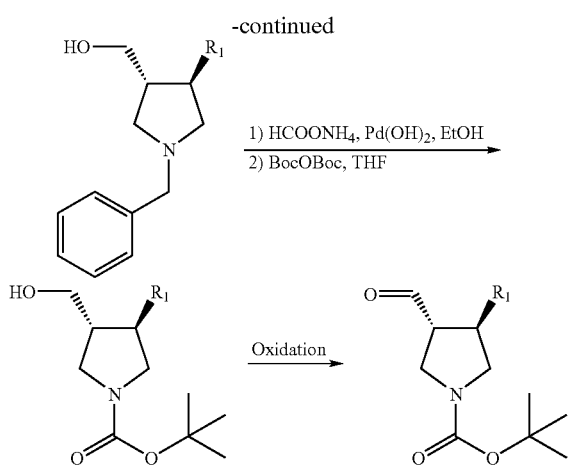

Preparation 9

(3R,4S)-3-Formyl-4-phenyl-pyrrolidine-1-carboxylic acid tert-butyl ester

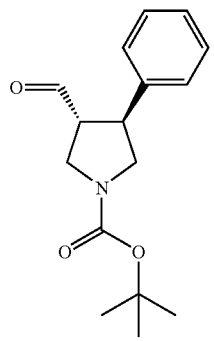

Step 1: To (S)-(+)-4-phenyl-2-oxazolidinone (9.88 g, 60 mmol) in THF (150 mL) at −78° C., was added n-butyl lithium (37.7 mL, 1.6M in hexanes, 60 mmol) over a period of 30 minutes. THF (50 mL) was added to the resultant thick suspension and the reaction mixture allowed to warm up to facilitate stirring. Trans-cinnamoylchloride (11.5 g, 69 mmol) in THF (30 mL) was added dropwise. The reaction was stirred at room temperature overnight. The reaction mixture was quenched with a saturated ammonium chloride solution (50 mL) and stirred for 0.5h. The solvent was removed in vacuo, the residue dissolved in ethyl acetate, washed with water (300 mL), 5% sodium bicarbonate (200 mL) and brine (100 mL) and dried over sodium sulfate. The solvent was removed in vacuo to give a pale yellow solid. The compound was crystallized from ethylacetate and washed with hexanes to give 17.12 g (97%) of (S)-4-phenyl-3-[(E)-(3-phenyl-acryloyl)]-oxazolidin-2-one.

$^1$H NMR (400 MHz, CDCl$_3$): δ [ppm] 7.92 (d, 1H), 7.77 (d, 1H), 7.59 (m, 2H), 7.40-7.35 (m, 8H), 5.55 (dd, 1H), 4.74 (t, 1H), 4.31 (dd, 1H).

Step 2: N-Benzyl-N-(methoxymethyl)trimethylsilylmethylamine (10.03 g, 40.5 mmol) was added to (S)-4-phenyl-3-[(E)-(3-henyl-acryloyl)]-oxazolidin-2-one (10.3 g, 35.1 mmol) in toluene (150 mL) at 0° C. and the mixture was stirred for 20 minutes. Trifluoroacetic acid (9.7 mL) in dichloromethane (125 mL) was added dropwise to the reaction mixture keeping the internal temperature at 0° C. The reaction was stirred at room temperature overnight. The reaction mixture was poured into saturated sodium bicarbonate (200 mL) and extracted with dichloromethane (2×75 mL). The combined organic phases were washed with brine and dried over sodium sulfate. The organic phases were concentrated to give a waxy solid, which was purified by flash silica gel chromatography eluting with ethyl acetate:hexanes (1:9) to give 9.68 g (61%) of (S)-3-((3R,4S)-1-benzyl-4-phenyl-pyrrolidine-3-carbonyl)-4-phenyl-oxazolidin-2-one.

$^1$H NMR (400 MHz, CDCl$_3$): δ [ppm] 7.33-7.11 (m, 15H), 5.31 (m, 1H), 4.53 (t, 1H), 4.11 (m, 2H), 3.93 (q, 1H), 3.67 (dd, 1H), 3.48 (d, 1H), 3.22 (t, 1H), 3.03 (t, 1H), 2.69 (dd, 1H), 2.60 (t, 1H).

Step 3: To (S)-3-((3R,4S)-1-benzyl-4-phenyl-pyrrolidine-3-carbonyl)-4-phenyl-oxazolidin-2-one (9.96 g, 23.35 mmol) in THF (100 mL) in a three-necked flask equipped with a thermometer and addition funnel was added lithium aluminium hydride (48 mL, 1M in THF) dropwise so that the temperature did not exceed 40° C. When addition was complete, the reaction was stirred at room temperature overnight. The reaction was carefully quenched with water (1.6 mL), NaOH (1.6 mL, 2N) and water (4.5 mL). After stirring for 15 minutes, the reaction mixture was filtered through a pad of celite and rinsed with THF (40 mL). The filtrate was concentrated to give a pale yellow oil, which was purified by flash silica gel chromatography eluting with ethyl acetate:hexanes (1:1) to give 3.38 g (55%) of ((3R,4S)-1-benzyl-4-phenyl-pyrrolidin-3-yl)-methanol.

$^1$H NMR (400 MHz, CDCl$_3$): δ [ppm] 7.4-7.2 (m, 10H), 3.73 (m, 2H), 3.66 (m, 2H), 3.3-3.2 (m, 2H), 2.9-2.8 (m, 2H), 2.5-2.4 (m, 2H).

LC/MS: m/z 267 (MH$^+$).

Step 4: To ((3R,4S)-1-benzyl-4-phenyl-pyrrolidin-3-yl)-methanol (2.28 g, 8.54 mmol) in ethanol (200 mL) was added ammonium formate (5.39 g, 85.49 mmol) and palladium hydroxide (446 mg, 20 wt % Pd) and the mixture was refluxed for 1.5h. Ammonia in methanol (0.8 mL, 2M) was added to the reaction mixture and refluxed for an additional 0.5h. The reaction mixture was filtered through celite and concentrated to give ((3R,4S)-4-phenyl-pyrrolidin-3-yl)-methanol as a colorless oil (1.25 g) which was used directly in the next step.

Step 5: To ((3R,4S)-4-phenyl-pyrrolidin-3-yl)-methanol (1.25 g, 7.05 mmol) in THF (35 mL) was added triethylamine (0.97 mL, 7.05 mmol) at room temperature. The reaction mixture was cooled to 0° C. and di-tert-butyl dicarbonate (1.53 g, 7.05 mmol) dissolved in THF (10 mL) was added. The reaction mixture was stirred overnight at room temperature. Then the reaction mixture was concentrated to give a colorless oil, which was purified by flash silica gel chromatography eluting with ethyl acetate:hexanes (2:3) to give 1.31 g (70%) of (3R,4S)-3-hydroxymethyl-4-phenyl-pyrrolidine-1-carboxylic acid tert-butyl ester.

$^1$H NMR (400 MHz, CDCl$_3$): δ [ppm] 7.31 (m, 2H), 7.23 (m, 3H), 3.82 (m, 1H), 3.76 (m, 1H), 3.66 (dd, 1H), 3.52 (dd, 1H), 3.38 (t, 1H), 3.28 (t, 1H), 3.11 (m, 2H), 2.49 (m, 2H), 1.46 (s, 9H).

Step 6: Oxalyl chloride (3.3 mL, 2M in CH$_2$Cl$_2$, 6.42 mmol) was stirred in dichloromethane (3 mL) in a three-necked flask. The reaction mixture was cooled to −78° C., and dimethyl sulfoxide (0.91 mL, 12.85 mmol) was added so that the internal temperature did not exceed −65° C. The reaction mixture was then stirred for 15 minutes. The (3R,4S)-3-hydroxymethyl-4-phenyl-pyrrolidine-1-carboxylic acid tert-butyl ester (713 mg, 2.57 mmol) in dichloromethane (6 mL) was added dropwise keeping the internal temperature below −65° C. and then stirred for 15 minutes. Diisopropylethylamine (4.5 mL, 25.7 mmol) was added keeping the internal temperature below −65° C. and then stirred for 20 minutes. The cooling bath was removed and the reaction mixture was stirred at room temperature for 2h. The reaction mixture was concentrated to give a colorless oil, which was purified by flash silica gel chromatography eluting with ethyl acetate:hexanes (1:4) to give 496 mg (70%) of (3R,4S)-3-formyl-4-phenyl-pyrrolidine-1-carboxylic acid tert-butyl ester.

$^1$H NMR (400 MHz, CDCl$_3$): δ [ppm] 9.65 (s, 1H), 7.36-7.32 (m, 5H), 4.0-3.4 (m, 6H), 3.20 (m, 1H), 1.46 (s,9H).

Scheme 8

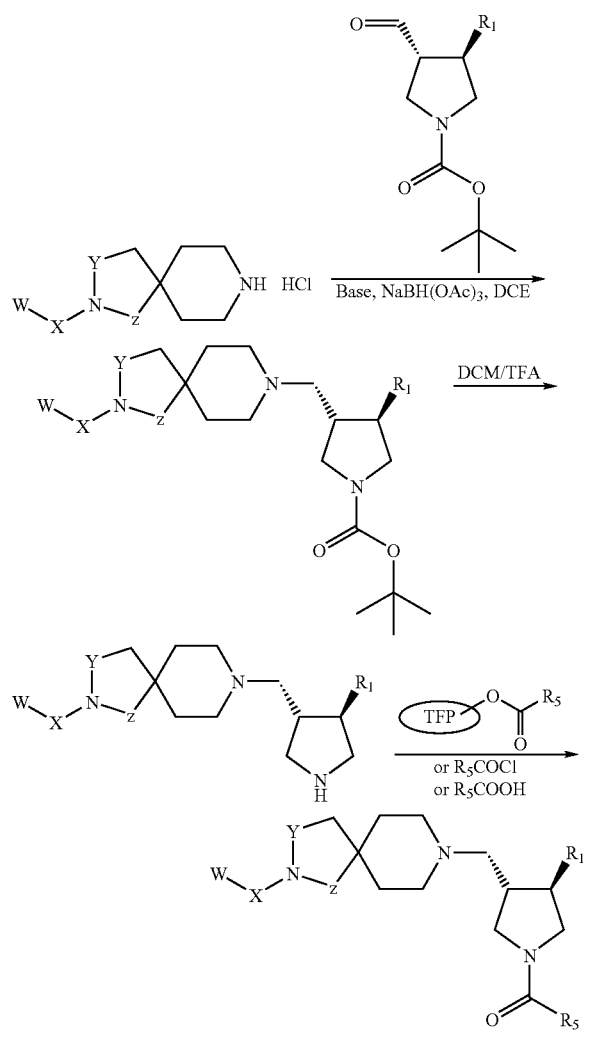

Example 7

(3S,4S)-3-[2-(4-Methoxy-benzyl)-1-oxo-2,8-diaza-spiro[4.5]dec-8-ylmethyl]-4-phenyl-pyrrolidine-1-carboxylic acid tert-butyl ester (Compound 110)

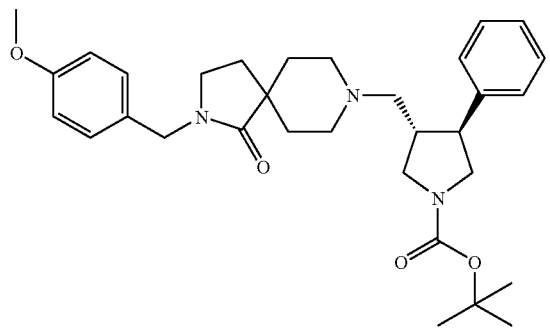

To 3.41 g of 2-(4-methoxy-benzyl)-2,8-diaza-spiro[4.5]decan-1-one hydrochloride (12.3 mmol) in dichloromethane (50 mL) was added triethylamine (1.71 mL, 12.3 mmol) followed by 3.85 g of (3R,4S)-3-formyl-4-phenyl-pyrrolidine-1-carboxylic acid tert-butyl ester (12.3 mmol) in dichloromethane (75 mL) and stirred for 1 h at room temperature. Sodium triacetoxyborohydride (3.91 g, 18.4 mmol) was then added and the reaction mixture stirred overnight at room temperature.

The reaction mixture was diluted with dichloromethane, the organic layer washed with aqueous sodium bicarbonate, and then dried over sodium sulfate. The organic layer was concentrated and purified by flash silica chromatography eluting with methanol: dichloromethane (1:50) to give 5.92 g (90%) of Compound 110 as a white solid.

$^1$H NMR (400 MHz, CD$_3$OD): δ [ppm] 7.33-7.20 (m, 5H), 7.11 (d, 2H), 6.85 (d, 2H), 4.33 (s, 2H), 3.85-3.71 (m, 2H), 3.74 (s, 3H), 3.4-2.5 (m, 10H), 2.4-2.2 (m, 1H), 2.1-2.0 (m, 1H), 2.0-1.8 (m, 4H), 1.46 (d, 9H), 1.36-1.32 (m, 2H).

Example 8

2-(4-Methoxy-benzyl)-8-((3R,4S)-4-phenyl-pyrrolidin-3-ylmethyl)-2,8-diaza-spiro[4.5]decan-1-one (Compound 111)

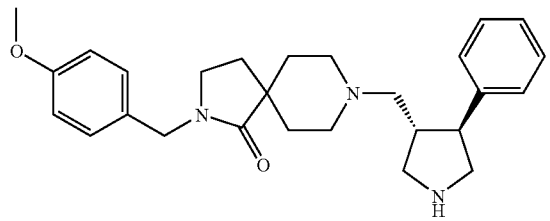

To 5.81 g (10.9 mmol) of (3S,4S)-3-[2-(4-methoxy-benzyl)-1-oxo-2,8-diaza-spiro[4.5]dec-8-ylmethyl]-4-phenyl-pyrrolidine-1-carboxylic acid tert-butyl ester in dichloromethane (100 mL) was added trifluoroacetic acid (30 mL) and the solution was stirred for 1 h at room temperature. The reaction mixture was neutralized with 1N NaOH (40 mL) and extracted with dichloromethane. The organic layer was dried over sodium sulfate and concentrated to give Compound 111 as a white foam (4.42 g, 94%).

$^1$H NMR (400 MHz, CDCl$_3$): δ [ppm] 7.32-7.15 (m, 5H), 7.10 (d, 2H), 6.82 (d, 2H), 4.35 (s, 2H), 3.77 (s, 3H), 3.46 (m, 2H), 3.08-2.29 (m, 10H), 2.02-1.76 (m, 6H), 1.33-1.25 (m, 2H).

Example 9

8-[(3S,4S)-1-(2-Cyclopropyl-acetyl)-4-phenyl-pyrrolidin-3-ylmethyl]-2-(4-methoxy-benzyl)-2,8-diaza-spiro[4.5]decan-1-one hydrochloride (Compound 117)

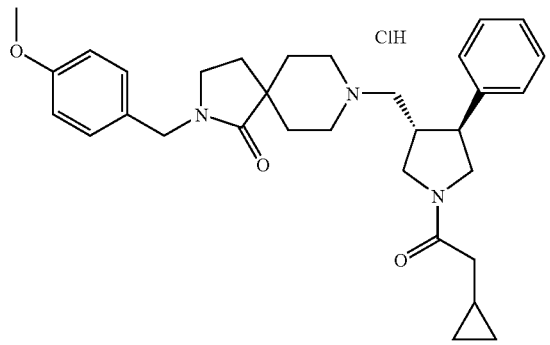

To 100 mg (0.23 mmol) of 2-(4-methoxy-benzyl)-8-((3R,4S)-4-phenyl-pyrrolidin-3-ylmethyl)-2,8-diaza-spiro[4.5]decan-1-one in DMF (1 mL) was added cyclopropylmethylacetic acid (39 mg, 0.311 mmol), DIC (31 μL, 0.311 mmol) and DMAP (8 mg, 0.065 mmol) and the mixture was stirred overnight at room temperature. The reaction mixture was concentrated and purified by flash silica chromatography eluting first with ethyl acetate:hexanes (20%-100%) and then with methanol:dichloromethane (1:25) to give 116 mg (72%) of 8-[(3S,4S)-1-(2-cyclopropyl-acetyl)-4-phenyl-pyrrolidin-3-ylmethyl]-2-(4-methoxy-benzyl)-2,8-diaza-spiro[4.5]decan-1-one. The compound was then dissolved in methanol (2 mL) and HCl (aq., 0.2M, 3 mL) and stirred for 10 minutes. The solvent was removed in vacuo, and the solution lyophilized to give the Compound 117 (120 mg, 95%).

$^1$H NMR (400 MHz, DMSO-d$_6$): δ [ppm] 9.68 (br d, 1H), 7.31-7.21 (m, 5H), 7.02 (d, 2H), 6.80 (d, 2H), 4.20 (s, 2H), 3.82-3.7 (m, 1H), 3.63 (s, 3H), 3.60-2.60 (m, 12H), 2.23-1.70 (m, 7H), 1.45 (m, 2H), 0.90 (m, 1H), 0.40 (m, 2H), 0.01 (m, 2H).

Table 3 of compounds illustrates some of the compounds of the present invention which were synthesized using the procedures described in scheme 8.

TABLE 3

| CPD # | STRUCTURE | | COMPOUND NAME | MOL WT | PURITY |
|---|---|---|---|---|---|
| 100 | 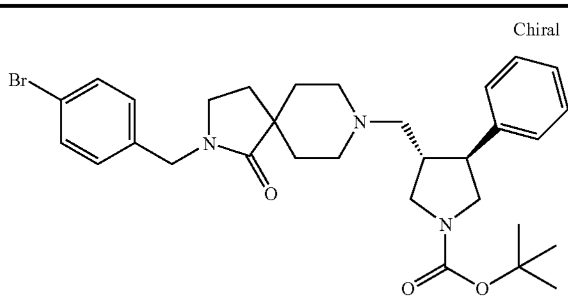 | Chiral | (3S,4S)-3-[2-(4-Bromo-benzyl)-1-oxo-2,8-diaza-spiro[4.5]dec-8-ylmethyl]-4-phenyl-pyrrolidine-1-carboxylic acid tert-butyl ester | 582.59 | >99.9% (HPLC) |
| 101 | 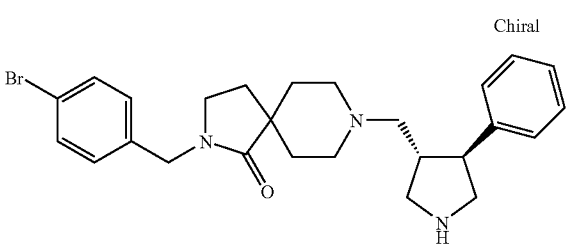 | Chiral | 2-(4-Bromo-benzyl)-8-((3R,4S)-4-phenyl-pyrrolidin-3-ylmethyl)-2,8-diaza-spiro[4.5]decan-1-one | 482.47 | 96.2% (LC/MS) |
| 102 | 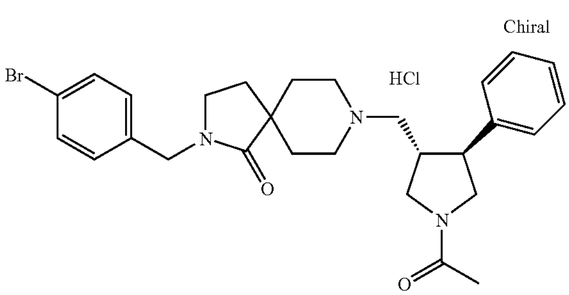 | Chiral | 8-((3S,4S)-1-Acetyl-4-phenyl-pyrrolidin-3-ylmethyl)-2-(4-bromo-benzyl)-2,8-diaza-spiro[4.5]decan-1-one hydrochloride | 560.97 | >99.9% (LC/MS) |

TABLE 3-continued

| CPD # | STRUCTURE | COMPOUND NAME | MOL WT | PURITY |
|---|---|---|---|---|
| 103 | 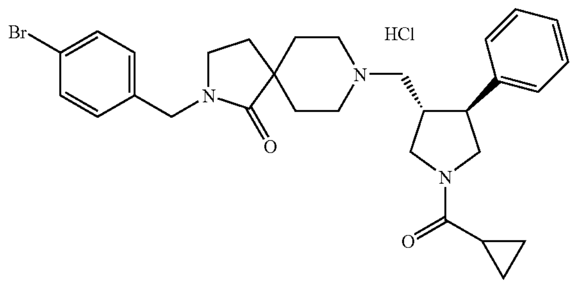 | 2-(4-Bromo-benzyl)-8-((3S,4S)-1-cyclopropanecarbonyl-4-phenyl-pyrrolidin-3-ylmethyl)-2,8-diaza-spiro[4.5]decan-1-one hydrochloride | 587.01 | >99.9% (LC/MS) |
| 104 | 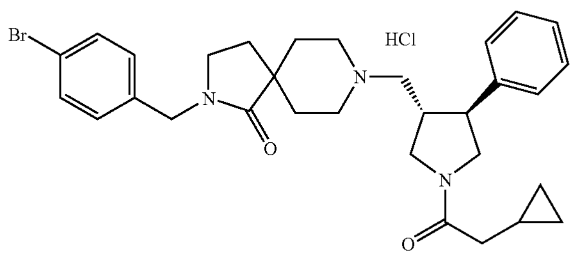 | 2-(4-Bromo-benzyl)-8-[(3S,4S)-1-(2-cyclopropyl-acetyl)-4-phenyl-pyrrolidin-3-ylmethyl]-2,8-diaza-spiro[4.5]decan-1-one hydrochloride | 601.03 | >99.9% (LC/MS) |
| 105 | 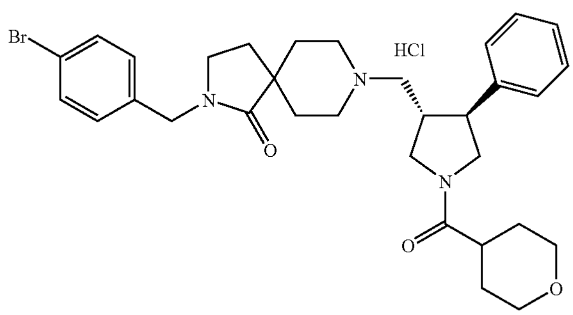 | 2-(4-Bromo-benzyl)-8-[(3S,4S)-4-phenyl-1-(tetrahydro-pyran-4-carbonyl)-pyrrolidin-3-ylmethyl]-2,8-diaza-spiro[4.5]decan-1-one hydrochloride | 631.06 | >99.9% (LC/MS) |
| 106 | 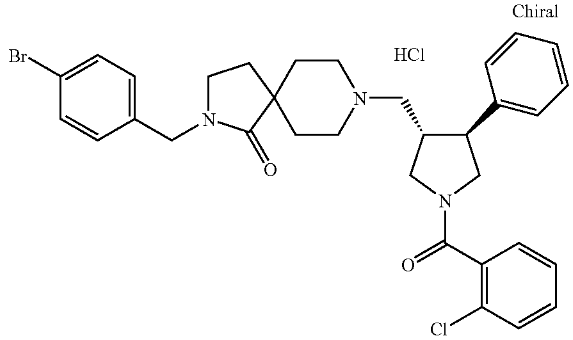 | 2-(4-Bromo-benzyl)-8-[(3S,4S)-1-(2-chloro-benzoyl)-4-phenyl-pyrrolidin-3-ylmethyl]-2,8-diaza-spiro[4.5]decan-1-one hydrochloride | 657.48 | >99.9% (LC/MS) |

TABLE 3-continued

| CPD # | STRUCTURE | COMPOUND NAME | MOL WT | PURITY |
|---|---|---|---|---|
| 107 | 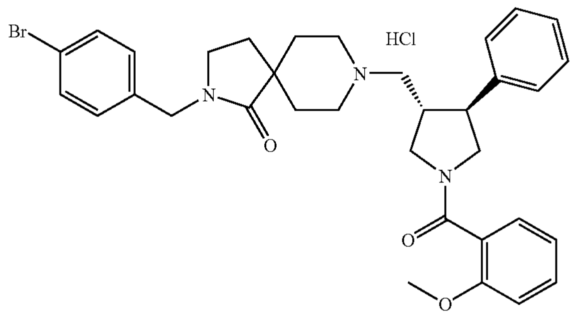 | 2-(4-Bromo-benzyl)-8-[(3S,4S)-1-(2-methoxy-benzoyl)-4-phenyl-pyrrolidin-3-ylmethyl]-2,8-diaza-spiro[4.5]decan-1-one hydrochloride | 653.07 | >99.9% (LC/MS) |
| 108 | 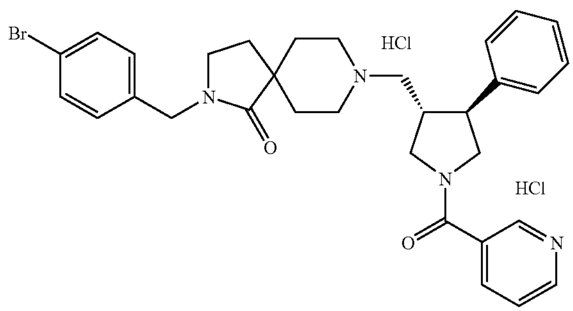 | 2-(4-Bromo-benzyl)-8-[(3S,4S)-4-phenyl-1-(pyridine-3-carbonyl)-pyrrolidin-3-ylmethyl]-2,8-diaza-spiro[4.5]decan-1-one dihydrochloride | 660.49 | >99.9% (HPLC) |
| 109 | 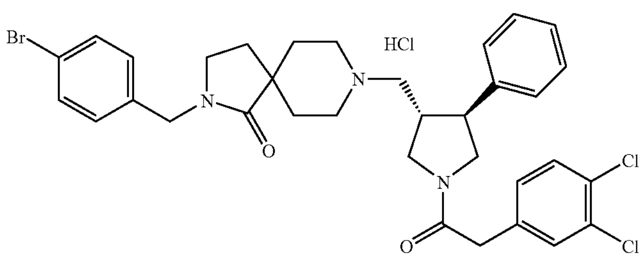 | 2-(4-Bromo-benzyl)-8-{(3S,4S)-1-[2-(3,4-dichloro-phenyl)-acetyl]-4-phenyl-pyrrolidin-3-ylmethyl}-2,8-diaza-spiro[4.5]decan-1-one hydrochloride | 705.96 | 96% (LC/MS) |
| 110 | 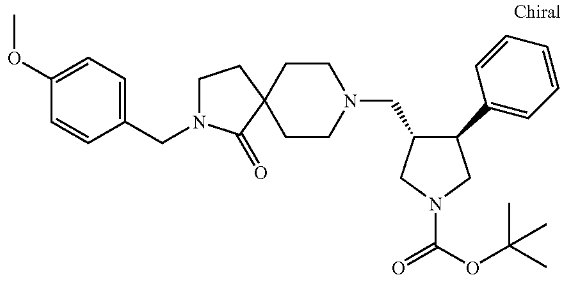 | (3S,4S)-3-[2-(4-Methoxy-benzyl)-1-oxo-2,8-diaza-spiro[4.5]dec-8-ylmethyl]-4-phenyl-pyrrolidine-1-carboxylic acid tert-butyl ester | 533.72 | >99.9% (LC/MS) |
| 111 | 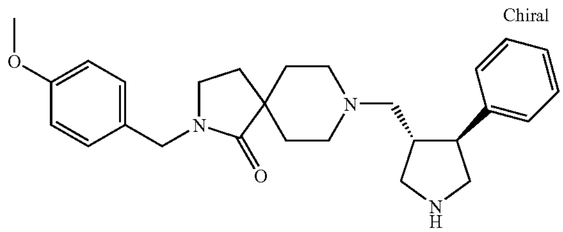 | 2-(4-Methoxy-benzyl)-8-((3R,4S)-4-phenyl-pyrrolidin-3-ylmethyl)-2,8-diaza-spiro[4.5]decan-1-one | 433.60 | >99.9% (LC/MS) |

TABLE 3-continued

| CPD # | STRUCTURE | COMPOUND NAME | MOL WT | PURITY |
|---|---|---|---|---|
| 112 | 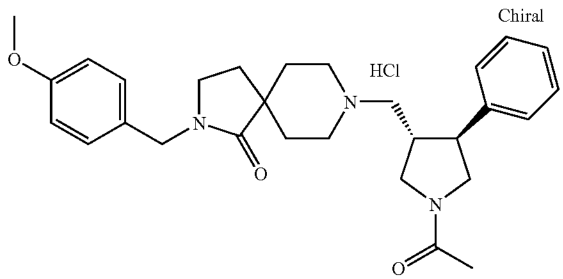 | 8-((3S,4S)-1-Acetyl-4-phenyl-pyrrolidin-3-ylmethyl)-2-(4-methoxy-benzyl)-2,8-diaza-spiro[4.5]decan-1-one hydrochloride | 512.10 | 72.4% (HPLC) |
| 113 | 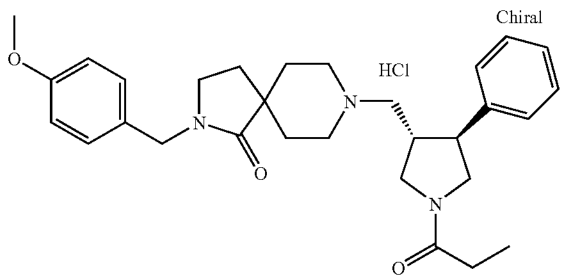 | 2-(4-Methoxy-benzyl)-8-((3S,4S)-4-phenyl-1-propionyl-pyrrolidin-3-ylmethyl)-2,8-diaza-spiro[4.5]decan-1-one hydrochloride | 526.12 | >99.9% (HPLC) |
| 114 | 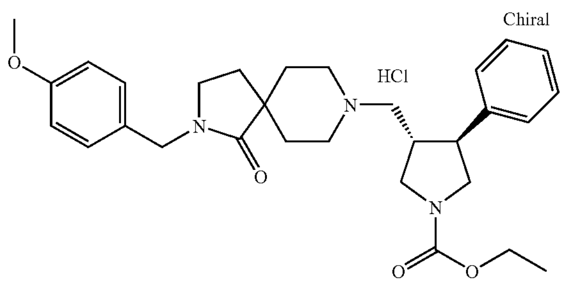 | 8-[(3S,4S)-1-(2-Methoxy-acetyl)-4-phenyl-pyrrolidin-3-ylmethyl]-2-(4-methoxy-benzyl)-2,8-diaza-spiro[4.5]decan-1-one hydrochloride | 542.12 | 99.5% (HPLC) |
| 115 | 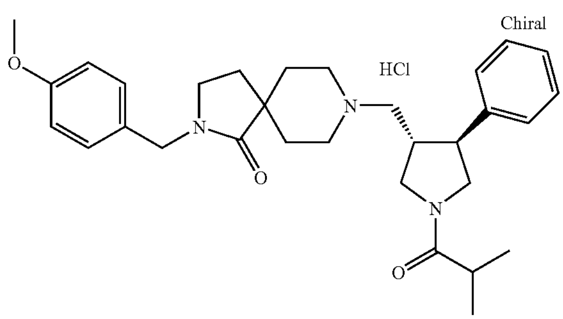 | 8-((3S,4S)-1-Isobutyryl-4-phenyl-pyrrolidin-3-ylmethyl)-2-(4-methoxy-benzyl)-2,8-diaza-spiro[4.5]decan-1-one hydrochloride | 540.15 | 99.8% (HPLC) |
| 116 | 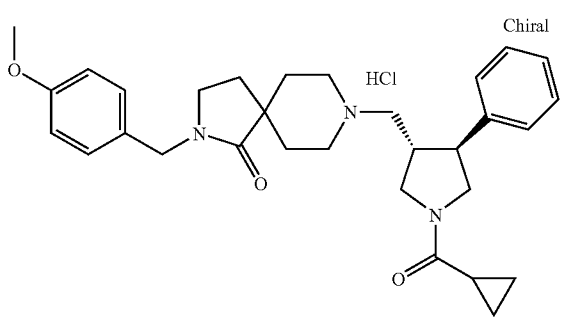 | 8-((3S,4S)-1-Cyclopropanecarbonyl-4-phenyl-pyrrolidin-3-ylmethyl)-2-(4-methoxy-benzyl)-2,8-diaza-spiro[4.5]decan-1-one hydrochloride | 538.14 | 98.0% (HPLC) |

TABLE 3-continued

| CPD # | STRUCTURE | COMPOUND NAME | MOL WT | PURITY |
|---|---|---|---|---|
| 117 | 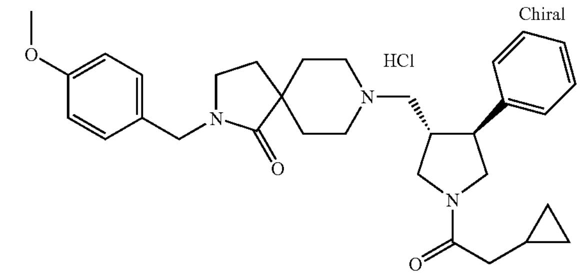 | 8-[(3S,4S)-1-(2-Cyclopropyl-acetyl)-4-phenyl-pyrrolidin-3-ylmethyl]-2-(4-methoxy-benzyl)-2,8-di-aza-spiro[4.5]decan-1-one hydrochloride | 552.16 | 94.3% (HPLC) |
| 118 | 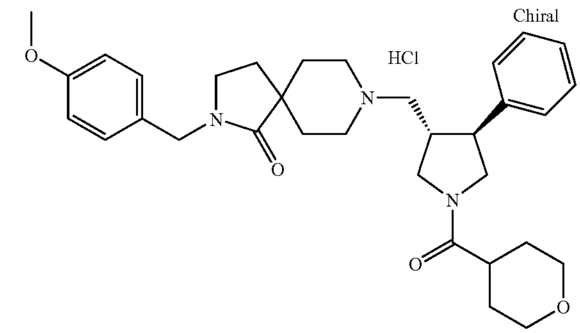 | 2-(4-Methoxy-benzyl)-8-[(3S,4S)-4-phenyl-1-(tetrahydro-pyran-4-carbonyl)-pyrrolidin-3-ylmethyl]-2,8-di-aza-spiro[4.5]decan-1-one hydrochloride | 582.19 | >99.9% (HPLC) |
| 119 | 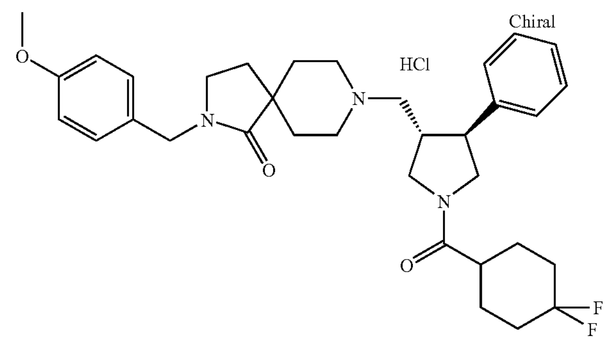 | 8-[(3S,4S)-1-(4,4-Difluoro-cyclohexanecarbonyl)-4-phenyl-pyrrolidin-3-ylmethyl]-2-(4-methoxy-benzyl)-2,8-diaza-spiro[4.5]decan-1-one hydrochloride | 616.20 | 99.7% (HPLC) |
| 120 | 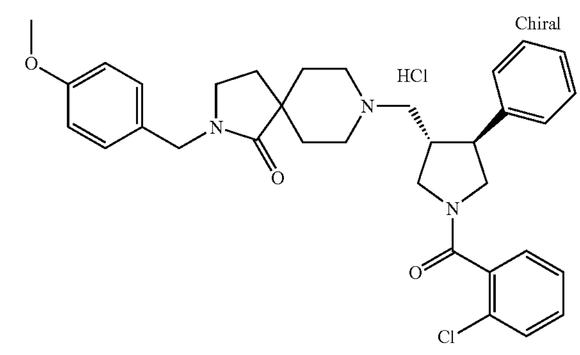 | 8-[(3S,4S)-1-(2-Chloro-benzoyl)-4-phenyl-pyrrolidin-3-ylmethyl]-2-(4-methoxy-benzyl)-2,8-diaza-spiro[4.5]decan-1-one hydrochloride | 608.61 | >99.9% (HPLC) |

TABLE 3-continued

| CPD # | STRUCTURE | COMPOUND NAME | MOL WT | PURITY |
|---|---|---|---|---|
| 121 | Chiral | 8-[(3S,4S)-1-(2-Fluoro-benzoyl)-4-phenyl-pyrrolidin-3-ylmethyl]-2-(4-methoxy-benzyl)-2,8-diaza-spiro[4.5]decan-1-one hydrochloride | 592.16 | 99.8% (HPLC) |
| 122 | Chiral | 2-(4-Methoxy-benzyl)-8-[(3S,4S)-4-phenyl-1-(pyrimidine-5-carbonyl)-pyrrolidin-3-ylmethyl]-2,8-diaza-spiro[4.5]decan-1-one trihydrochloride | 649.06 | >99.9% (HPLC) |
| 123 | Chiral | 8-[(3S,4S)-1-(4,6-Dimethyl-pyrimidine-5-carbonyl)-4-phenyl-pyrrolidin-3-ylmethyl]-2-(4-methoxy-benzyl)-2,8-diaza-spiro[4.5]decan-1-one trihydrochloride | 677.12 | 98.8% (LC/MS) |
| 124 | Chiral | (3S,4S)-3-[2-(4-Methanesulfonyl-benzyl)-1-oxo-2,8-diaza-spiro[4.5]dec-8-ylmethyl]-4-phenyl-pyrrolidine-1-carboxylic acid tert-butyl ester | 581.78 | >99.9% (LC/MS) |

TABLE 3-continued

| CPD # | STRUCTURE | COMPOUND NAME | MOL WT | PURITY |
|---|---|---|---|---|
| 125 | 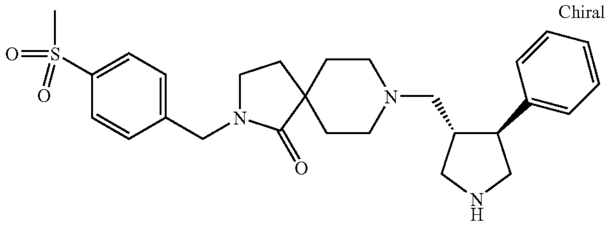 | 2-(4-Methane-sulfonyl-benzyl)-8-((3R,4S)-4-phenyl-pyrrolidin-3-ylmethyl)-2,8-diaza-spiro[4.5]decan-1-one | 481.66 | 97.0% (LC/MS) |
| 126 | 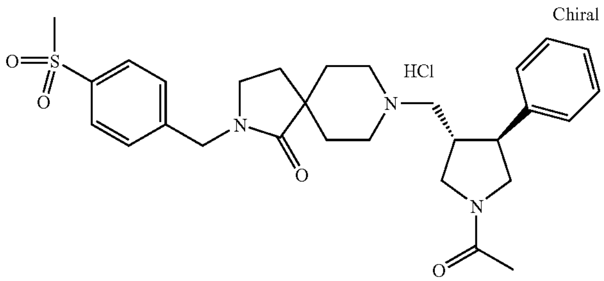 | 8-((3S,4S)-1-Acetyl-4-phenyl-pyrrolidin-3-ylmethyl)-2-(4-methanesulfonyl-benzyl)-2,8-diaza-spiro[4.5]decan-1-one hydrochloride | 560.16 | 83.7% (HPLC) |
| 127 | 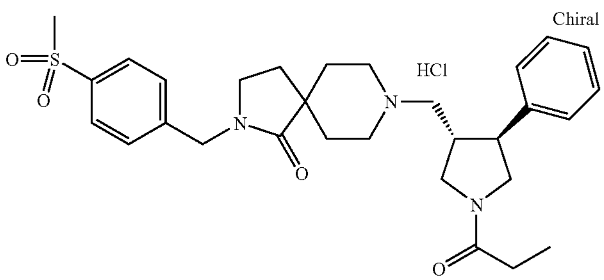 | 2-(4-Methane-sulfonyl-benzyl)-8-((3S,4S)-4-phenyl-1-propionyl-pyrrolidin-3-ylmethyl)-2,8-diaza-spiro[4.5]decan-1-one hydrochloride | 574.19 | 98.8% (HPLC) |
| 128 | 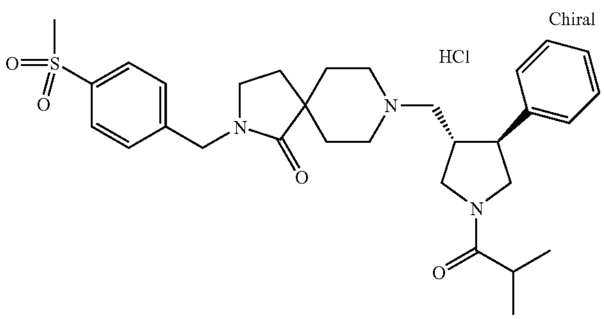 | 8-((3S,4S)-1-Isobutyryl-4-phenyl-pyrrolidin-3-ylmethyl)-2-(4-methanesulfonyl-benzyl)-2,8-diaza-spiro[4.5]decan-1-one hydrochloride | 588.22 | 98.7% (HPLC) |
| 129 | 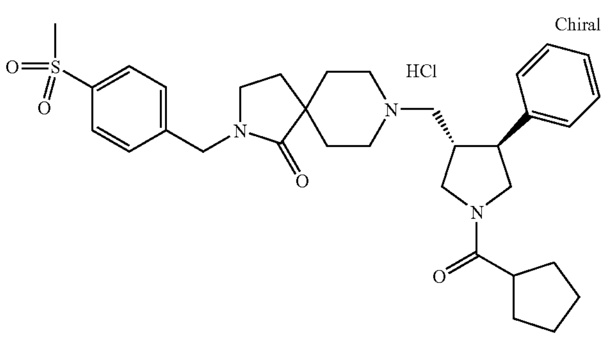 | 8-((3S,4S)-1-Cyclopentanecarbonyl-4-phenyl-pyrrolidin-3-ylmethyl)-2-(4-methanesulfonyl-benzyl)-2,8-diaza-spiro[4.5]decan-1-one hydrochloride | 614.25 | >99.9% (HPLC) |

TABLE 3-continued

| CPD # | STRUCTURE | COMPOUND NAME | MOL WT | PURITY |
|---|---|---|---|---|
| 130 | 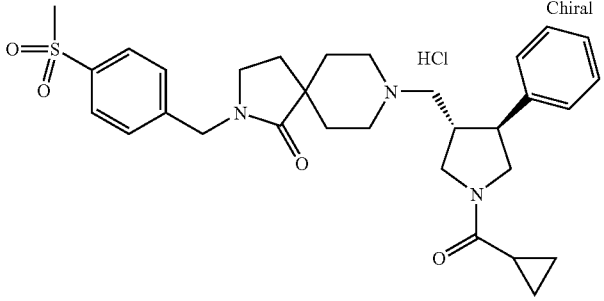 | 8-((3S,4S)-1-Cyclopropanecarbonyl-4-phenyl-pyrrolidin-3-ylmethyl)-2-(4-methanesulfonyl-benzyl)-2,8-diaza-spiro[4.5]decan-1-one hydrochloride | 586.20 | 99.5% (HPLC) |
| 131 | 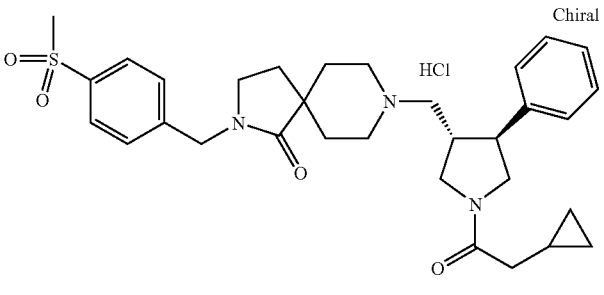 | 8-[(3S,4S)-1-(2-Cyclopropyl-acetyl)-4-phenyl-pyrrolidin-3-ylmethyl]-2-(4-methanesulfonyl-benzyl)-2,8-diaza-spiro[4.5]decan-1-one hydrochloride | 600.23 | 96.9% (HPLC) |
| 132 | 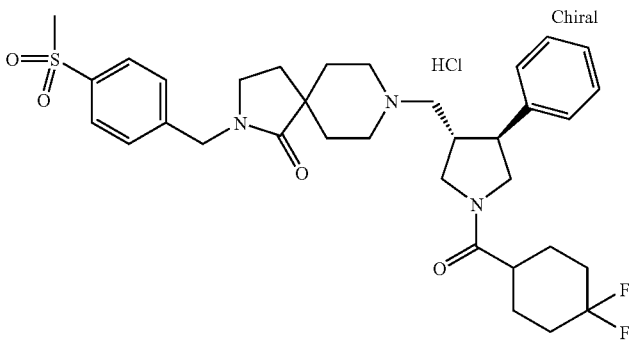 | 8-[(3S,4S)-1-(4,4-Difluoro-cyclohexanecarbonyl)-4-phenyl-pyrrolidin-3-ylmethyl]-2-(4-methanesulfonyl-benzyl)-2,8-diaza-spiro[4.5]decan-1-one hydrochloride | 664.26 | >99.9% (HPLC) |
| 133 | 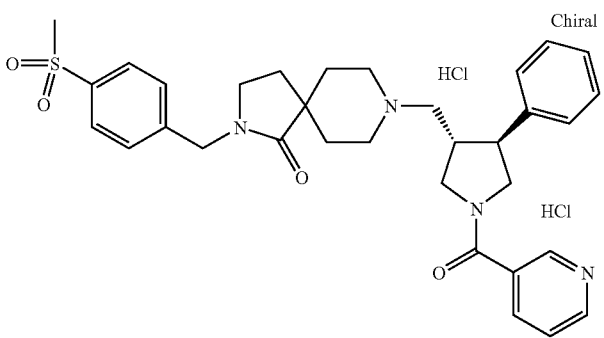 | 2-(4-Methanesulfonyl-benzyl)-8-[(3S,4S)-4-phenyl-1-(pyridine-3-carbonyl)-pyrrolidin-3-ylmethyl]-2,8-diaza-spiro[4.5]decan-1-one dihydrochloride | 659.68 | >99.9% (HPLC) |

TABLE 3-continued

| CPD # | STRUCTURE | COMPOUND NAME | MOL WT | PURITY |
|---|---|---|---|---|
| 134 | Chiral | 2-(4-Methane-sulfonyl-benzyl)-8-[(3S,4S)-4-phenyl-1-(pyrimidine-5-carbonyl)-pyrrolidin-3-ylmethyl]-2,8-diaza-spiro[4.5]decan-1-one trihydrochloride | 697.13 | >99.9% (HPLC) |
| 135 | Chiral | 8-[(3S,4S)-1-(4,6-Dimethyl-pyrimidine-5-carbonyl)-4-phenyl-pyrrolidin-3-ylmethyl]-2-(4-methanesulfonyl-benzyl)-2,8-diaza-spiro[4.5]decan-1-one trihydrochloride | 725.18 | >98% (HPLC) |
| 136 | Chiral | 8-[(3S,4S)-1-(2-Chloro-benzoyl)-4-phenyl-pyrrolidin-3-ylmethyl]-2-(4-methanesulfonyl-benzyl)-2,8-diaza-spiro[4.5]decan-1-one hydrochloride | 656.68 | 98.1% (HPLC) |
| 137 | Chiral | 8-[(3S,4S)-1-(2-Fluoro-benzoyl)-4-phenyl-pyrrolidin-3-ylmethyl]-2-(4-methanesulfonyl-benzyl)-2,8-diaza-spiro[4.5]decan-1-one hydrochloride | 640.22 | 98.3% (HPLC) |

TABLE 3-continued

| CPD # | STRUCTURE | COMPOUND NAME | MOL WT | PURITY |
|---|---|---|---|---|
| 138 | 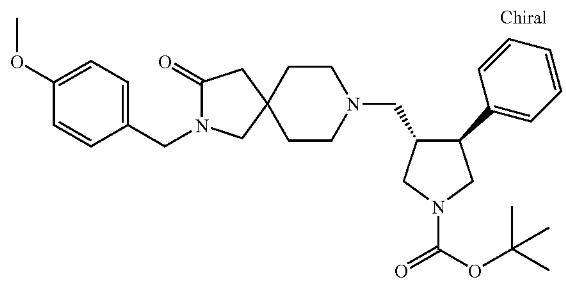 | (3S,4S)-3-[2-(4-Methoxy-benzyl)-3-oxo-2,8-diaza-spiro[4.5]dec-8-yl-methyl]-4-phenyl-pyrrolidine-1-carboxylic acid tert-butyl ester | 533.72 | 90% (1H NMR) |
| 139 | 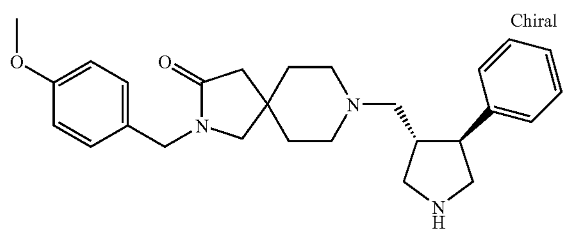 | 2-(4-Methoxy-benzyl)-8-((3R,4S)-4-phenyl-pyrrolidin-3-ylmethyl)-2,8-diaza-spiro[4.5]decan-3-one | 433.60 | 95% (1H NMR) |
| 140 | 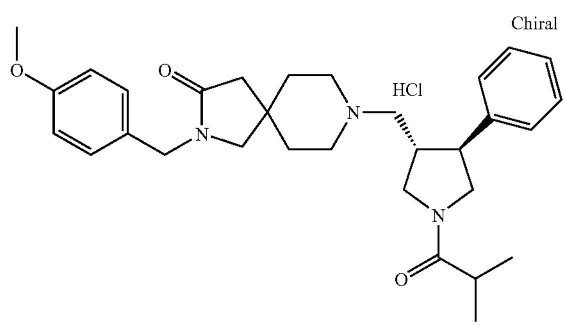 | 8-((3S,4S)-1-Isobutyryl-4-phenyl-pyrrolidin-3-ylmethyl)-2-(4-methoxy-benzyl)-2,8-diaza-spiro[4.5]decan-3-one hydrochloride | 540.15 | 95.4% (HPLC) |
| 141 | 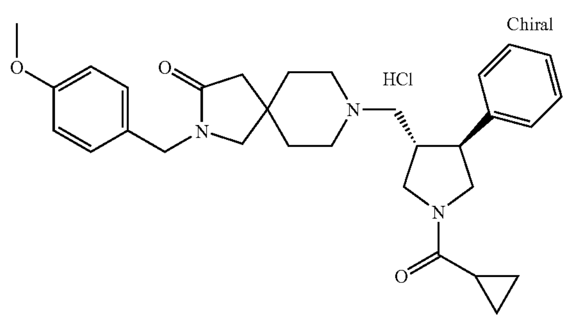 | 8-((3S,4S)-1-Cyclopropanecarbonyl-4-phenyl-pyrrolidin-3-ylmethyl)-2-(4-methoxy-benzyl)-2,8-diaza-spiro[4.5]decan-3-one hydrochloride | 538.13 | 99.3% (HPLC) |
| 142 | 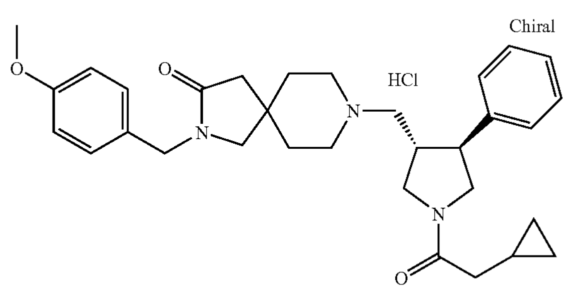 | 8-[(3S,4S)-1-(2-Cyclopropyl-acetyl)-4-phenyl-pyrrolidin-3-ylmethyl]-2-(4-methoxy-benzyl)-2,8-diaza-spiro[4.5]decan-3-one hydrochloride | 552.16 | 95.3% (HPLC) |

TABLE 3-continued

| CPD # | STRUCTURE | COMPOUND NAME | MOL WT | PURITY |
|---|---|---|---|---|
| 143 | Chiral | (3S,4S)-3-[2-(4-Methanesulfonyl-benzyl)-3-oxo-2,8-diaza-spiro[4.5]dec-8-yl-methyl]-4-phenyl-pyrrolidine-1-carboxylic acid tert-butyl ester | 581.78 | 90% (1H NMR) |
| 144 | Chiral | 2-(4-Methane-sulfonyl-benzyl)-8-((3R,4S)-4-phenyl-pyrrolidin-3-yl-methyl)-2,8-diaza-spiro[4.5]decan-3-one | 481.66 | 95% (1H NMR) |
| 145 | Chiral HCl | 8-((3S,4S)-1-Isobutyryl-4-phenyl-pyrrolidin-3-ylmethyl)-2-(4-methanesulfonyl-benzyl)-2,8-diaza-spiro[4.5]decan-3-one hydrochloride | 588.21 | 99.7% (HPLC) |
| 146 | Chiral HCl | 8-((3S,4S)-1-Cyclopropanecarbonyl-4-phenyl-pyrrolidin-3-ylmethyl)-2-(4-methanesulfonyl-benzyl)-2,8-diaza-spiro[4.5]decan-3-one hydrochloride | 586.20 | 99.7% (HPLC) |

TABLE 3-continued

| CPD # | STRUCTURE | COMPOUND NAME | MOL WT | PURITY |
|---|---|---|---|---|
| 147 | Chiral, HCl | 8-[(3S,4S)-1-(2-Cyclopropyl-acetyl)-4-phenyl-pyrrolidin-3-yl-methyl]-2-(4-methanesulfonyl-benzyl)-2,8-diaza-spiro[4.5]decan-3-one hydrochloride | 600.23 | 98.7% (HPLC) |
| 148 | Chiral, HCl | 2-(4-Bromo-benzyl)-8-((3S,4S)-4-phenyl-1-propionyl-pyrrolidin-3-yl-methyl)-2,8-diaza-spiro[4.5]decan-1-one hydrochloride | 574.99 | >99.9% (HPLC) |
| 149 | Chiral, HCl | 2-(4-Methane-sulfonyl-benzyl)-8-[(3S,4S)-4-phenyl-1-(tetrahydro-pyran-4-carbonyl)-pyrrolidin-3-yl-methyl]-2,8-diaza-spiro[4.5]decan-1-one hydrochloride | 630.25 | 99.2% (HPLC) |

Scheme 9

Example 10

8-((3S,4S)-1-Ethanesulfonyl-4-phenyl-pyrrolidin-3-ylmethyl)-2-(4-methanesulfonyl-benzyl)-2,8-diaza-spiro[4.5]decan-1-one hydrochloride (Compound 153)

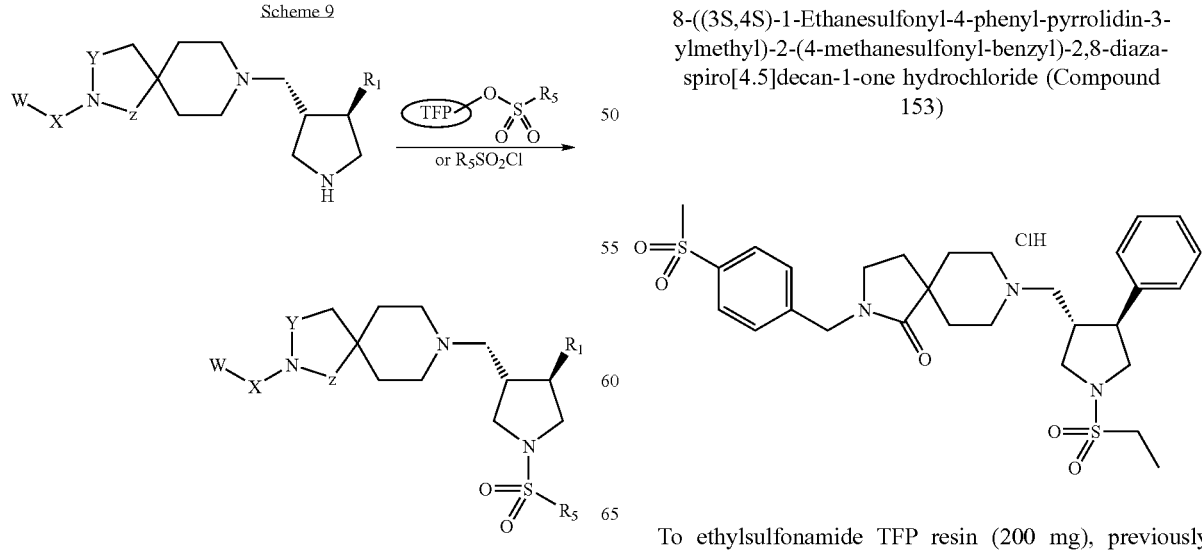

To ethylsulfonamide TFP resin (200 mg), previously swelled with 1 mL of anhydrous DMF, was added a solution of 2-(4-methanesulfonyl-benzyl)-8-((3R,4S)-4-phenyl-pyrrolidin-3-ylmethyl)-2,8-diaza-spiro[4.5]decan-1-one (60 µmol) in anhydrous DMF (1 mL). The reaction mixture was agitated overnight and then filtered and the resin washed with dichloromethane (3×2 mL). The organic portion was then concentrated in vacuo and purified by semi-preparative HPLC (Method D) and lyophilized to give the Compound 153 as a colorless solid (4.2 mg, 11%).

$^1$H NMR (400 MHz, DMSO-$d_6$): δ [ppm] 9.60 (br d, 1H), 7.83 (d, 2H), 7.38 (d, 2H), 7.29 (m, 5H), 4.40 (m, 2H), 3.89 (t, 1H), 3.66 (m, 1H), 3.52 (m, 1H), 3.14 (s, 3H), 2.92 (m, 11H), 1.88 (m, 6H), 1.55 (m, 2H), 1.21 (t, 3H).

Table 4 of compounds illustrates some of the compounds of the present invention which were synthesized using the procedures described in scheme 9.

TABLE 4

| CPD # | STRUCTURE | COMPOUND NAME | MOL WT | PURITY |
|---|---|---|---|---|
| 150 | 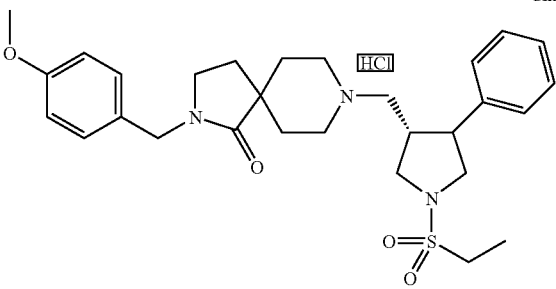 Chiral | 8-((3S,4S)-1-Ethanesulfonyl-4-phenyl-pyrrolidin-3-ylmethyl)-2-(4-methoxy-benzyl)-2,8-diaza-spiro[4.5]decan-1-one hydrochloride | 562.18 | 99.4% (HPLC) |
| 151 | 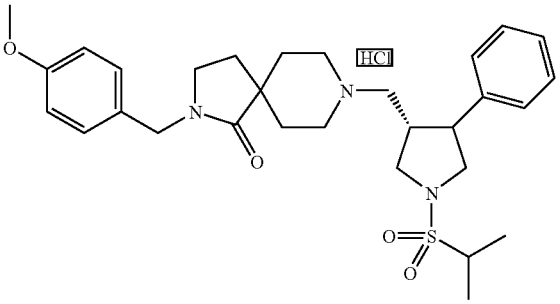 Chiral | 2-(4-Methoxy-benzyl)-8-[(3S,4S)-4-phenyl-1-(propane-2-sulfonyl)-pyrrolidin-3-ylmethyl]-2,8-diaza-spiro[4.5]decan-1-one hydrochloride | 576.20 | 89.9% (HPLC) |
| 152 | 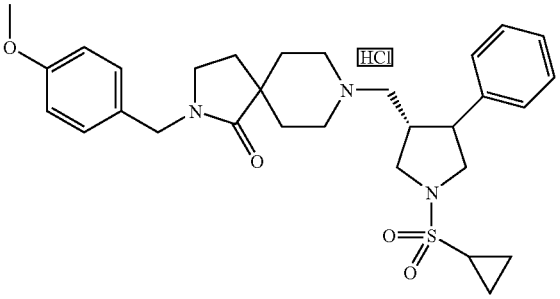 Chiral | 8-((3S,4S)-1-Cyclopropanesulfonyl-4-phenyl-pyrrolidin-3-ylmethyl)-2-(4-methoxy-benzyl)-2,8-diaza-spiro[4.5]decan-1-one hydrochloride | 574.19 | 97.9% (HPLC) |

TABLE 4-continued

| CPD # | STRUCTURE | COMPOUND NAME | MOL WT | PURITY |
|---|---|---|---|---|
| 153 | Chiral | 8-((3S,4S)-1-Ethanesulfonyl-4-phenyl-pyrrolidin-3-ylmethyl)-2-(4-methanesulfonyl-benzyl)-2,8-diaza-spiro[4.5]decan-1-one hydrochloride | 610.24 | 99.4% (HPLC) |
| 154 | Chiral | 2-(4-Methanesulfonyl-benzyl)-8-[(3S,4S)-4-phenyl-1-(propane-2-sulfonyl)-pyrrolidin-3-ylmethyl]-2,8-diaza-spiro[4.5]decan-1-one hydrochloride | 624.27 | 96.3% (HPLC) |
| 155 | Chiral | 8-((3S,4S)-1-Cyclopropanesulfonyl-4-phenyl-pyrrolidin-3-ylmethyl)-2-(4-methanesulfonyl-benzyl)-2,8-diaza-spiro[4.5]decan-1-one hydrochloride | 622.25 | 99.9% (HPLC) |
| 156 | Chiral | 8-((3S,4S)-1-Cyclopanesulfonyl-4-phenyl-pyrrolidin-3-ylmethyl)-2-(4-methanesulfonyl-benzyl)-2,8-diaza-spiro[4.5]decan-1-one hydrochloride | 650.30 | 99.3% (HPLC) |

Scheme 10

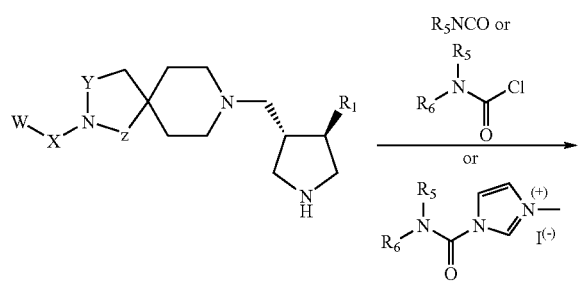

Example 11

2-(4-Methoxy-benzyl)-8-[(3S,4S)-1-(morpholine-4-carbonyl)-4-phenyl-pyrrolidin-3-ylmethyl]-2,8-diaza-spiro[4.5]decan-1-one hydrochloride (Compound 157)

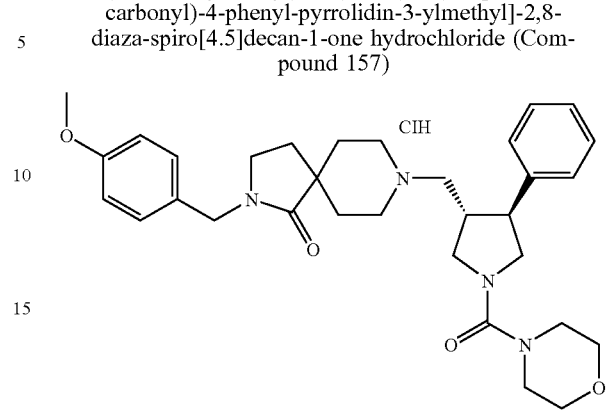

To a solution of 2-(4-methoxy-benzyl)-8-((3R,4S)-4-phenyl-pyrrolidin-3-ylmethyl)-2,8-diaza-spiro[4.5]decan-1-one (60 μmol) in anhydrous DCM (1 mL) was added 4-morpholinecarbonyl chloride (21 μL, 180 μmol). The reaction mixture was stirred overnight at room temperature. Saturated sodium bicarbonate aqueous solution was added to the reaction mixture and the aqueous layer washed with DCM (3×2 mL). The organic layer was then concentrated in vacuo and purified by semi-preparative HPLC (Method D) and lyophilized to give Compound 157 as a colorless solid (6.2 mg, 19%).

$^1$H NMR (400 MHz, DMSO-$d_6$): δ [ppm] 9.81 (br d, 1H), 7.31-7.21 (m, 5H), 7.04 (d, 2H), 6.82 (d, 2H), 4.20 (s, 2H), 3.82 (m, 1H), 3.65 (s, 3H), 3.6-3.4 (m, 6H), 3.4-2.6 (m, 15H), 2.03-1.73 (m, 4H), 1.45 (m, 2H).

Table 5 of compounds illustrates some of the compounds of the present invention which were synthesized using the procedures described in scheme 10.

TABLE 5

| CPD # | STRUCTURE | | COMPOUND NAME | MOL WT | PURITY |
|---|---|---|---|---|---|
| 157 | 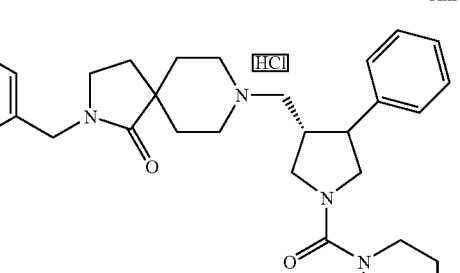 | Chiral | 2-(4-Methoxy-benzyl)-8-[(3S,4S)-1-(morpholine-4-carbonyl)-4-phenyl-pyrrolidin-3-ylmethyl]-2,8-diaza-spiro[4.5]decan-1-one hydrochloride | 583.18 | 96.8% (HPLC) |
| 158 | 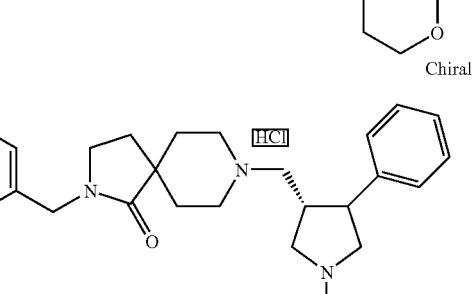 | Chiral | (3S,4S)-3-[2-(4-Methoxy-benzyl)-1-oxo-2,8-diaza-spiro[4.5]dec-8-ylmethyl]-4-phenyl-pyrrolidine-1-carboxylic acid dimethylamide hydrochloride | 541.14 | 95.6% (HPLC) |

TABLE 5-continued

| CPD # | STRUCTURE | COMPOUND NAME | MOL WT | PURITY |
|---|---|---|---|---|
| 159 | Chiral | 2-(4-Methoxy-benzyl)-8-[(3S,4S)-4-phenyl-1-pyrrolidin-3-ylmethyl]-2,8-diaza-spiro[4.5]decan-1-one hydrochloride | 567.17 | 99.5% (HPLC) |
| 160 | Chiral | 8-[(3S,4S)-1-(3,3-Difluoro-pyrrolidine-1-carbonyl)-4-phenyl-pyrrolidin-3-ylmethyl]-2-(4-methoxy-benzyl)-2,8-diaza-spiro[4.5]decan-1-one hydrochloride | 603.16 | 99.5% (HPLC) |
| 161 | Chiral | (3S,4S)-3-[2-(4-Methoxy-benzyl)-1-oxo-2,8-diaza-spiro[4.5]dec-8-ylmethyl]-4-phenyl-pyrrolidine-1-carboxylic acid cyclopropylamide hydrochloride | 553.15 | 95.2% (HPLC) |
| 162 | Chiral | (3S,4S)-3-[2-(4-Methoxy-benzyl)-1-oxo-2,8-diaza-spiro[4.5]dec-8-ylmethyl]-4-phenyl-pyrrolidine-1-carboxylic acid cyclopentylamide hydrochloride | 581.20 | 99.5% (HPLC) |

TABLE 5-continued

| CPD # | STRUCTURE | COMPOUND NAME | MOL WT | PURITY |
|---|---|---|---|---|
| 163 | Chiral | 2-(4-Methanesulfonyl-benzyl)-8-[(3S,4S)-1-(morpholine-4-carbonyl)-4-phenyl-pyrrolidin-3-ylmethyl]-2,8-diaza-spiro[4.5]decan-1-one hydrochloride | 631.24 | 99.4% (HPLC) |
| 164 | Chiral | (3S,4S)-3-[2-(4-Methanesulfonyl-benzyl)-1-oxo-2,8-diaza-spiro[4.5]dec-8-ylmethyl[-4-phenyl-pyrrolidine-1-carboxylic acid dimethylamide hydrochloride | 589.20 | 94.8% (HPLC) |
| 165 | Chiral | 2-(4-Methanesulfonyl-benzyl)-8-[(3S,4S)-4-phenyl-1-(pyrrolidine-1-carbonyl)-pyrrolidin-3-ylmethyl]-2,8-diaza-spiro[4.5]decan-1-one hydrochloride | 615.24 | 97.5% (HPLC) |
| 166 | Chiral | 8-[(3S,4S)-1-(3,3-Difluoro-pyrrolidine-1-carbonyl)-4-phenyl-pyrrolidin-3-ylmethyl]-2-(4-methanesulfonyl-benzyl)-2,8-diaza-spiro[4.5]decan-1-one hydrochloride | 651.22 | 99.7% (HPLC) |

TABLE 5-continued

| CPD # | STRUCTURE | | COMPOUND NAME | MOL WT | PURITY |
|---|---|---|---|---|---|
| 167 | 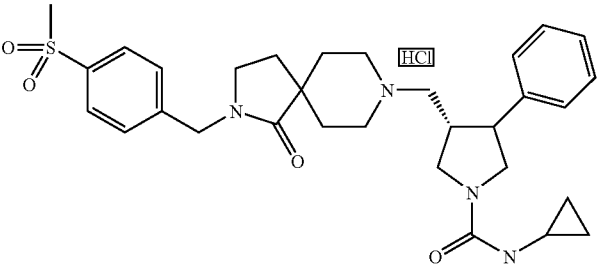 | Chiral | (3S,4S)-3-[2-(4-Methanesulfonyl-benzyl)-1-oxo-2,8-diaza-spiro[4.5]dec-8-ylmethyl]-4-phenyl-pyrrolidine-1-carboxylic acid cyclopropylamide hydrochloride | 601.21 | 97.5% (HPLC) |
| 168 | 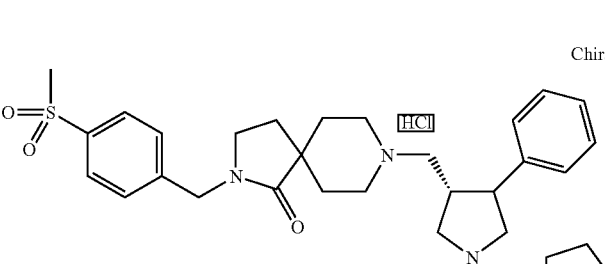 | Chiral | (3S,4S)-3-[2-(4-Methanesulfonyl-benzyl)-1-oxo-2,8-diaza-spiro[4.5]dec-8-ylmethyl]-4-phenyl-pyrrolidine-1-carboxylic acid cyopentylamide hydrochloride | 628.67 | 98.5% (HPLC) |

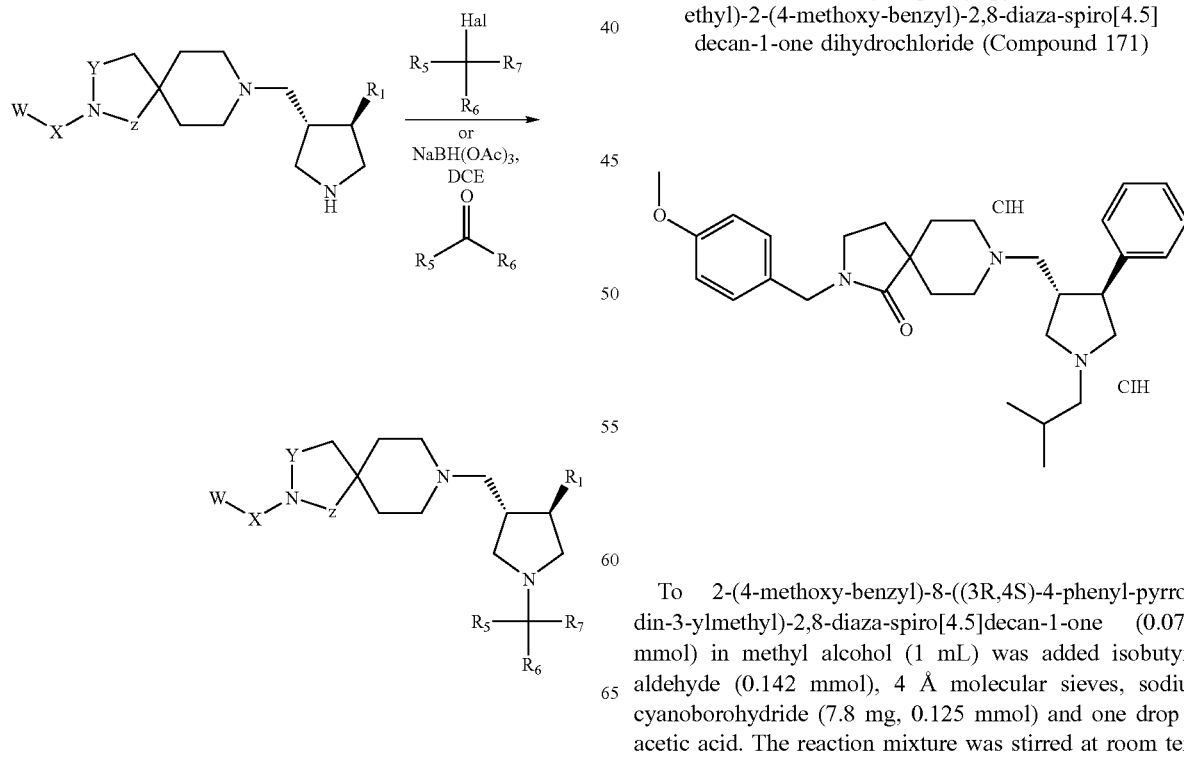

Example 12

8-((3S,4S)-1-Isobutyl-4-phenyl-pyrrolidin-3-ylmethyl)-2-(4-methoxy-benzyl)-2,8-diaza-spiro[4.5]decan-1-one dihydrochloride (Compound 171)

To 2-(4-methoxy-benzyl)-8-((3R,4S)-4-phenyl-pyrrolidin-3-ylmethyl)-2,8-diaza-spiro[4.5]decan-1-one (0.0714 mmol) in methyl alcohol (1 mL) was added isobutyryl aldehyde (0.142 mmol), 4 Å molecular sieves, sodium cyanoborohydride (7.8 mg, 0.125 mmol) and one drop of acetic acid. The reaction mixture was stirred at room temperature overnight. The reaction was then filtered, purified by semi-preparative HPLC (Method C) and lyophilized to give the Compound 171 as a colorless solid (15.9 mg, 42%).

$^1$H NMR (400 MHz, DMSO-$d_6$): δ [ppm] 11.00 (d, 1H), 10.4 (d, 1H), 7.5-7.3 (m, 5H), 7.07 (d, 2H), 6.86 (d, 2H), 4.26 (s, 2H), 3.8 (m, 1H), 3.69 (s, 3H), 3.4-2.6 (m, 14H), 2.05-1.65 (m, 6H), 1.45 (m, 1H), 1.00 (d, 6H), 0.91 (dd, 1H).

Table 6 of compounds illustrates some of the compounds of the present invention which were synthesized using the procedures described in scheme 11.

TABLE 6

| CPD # | STRUCTURE | | COMPOUND NAME | MOL WT | PURITY |
|---|---|---|---|---|---|
| 169 | 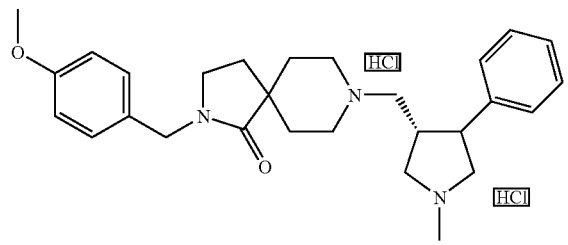 | Chiral | 2-(4-Methoxy-benzyl)-8-((3R,4S)-1-methyl-4-phenyl-pyrrolidin-3-ylmethyl)-2,8-diaza-spiro[4.5]decan-1-one dihydrochloride | 520.55 | 99.6% (HPLC) |
| 170 | 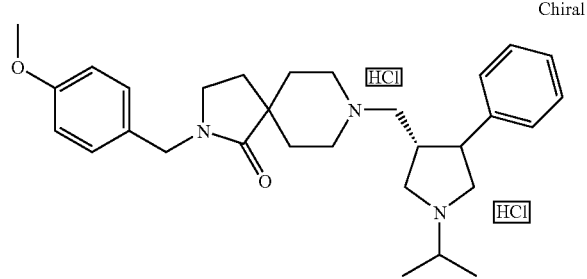 | Chiral | 8-((3S,4S)-1-Isopropyl-4-phenyl-pyrrolidin-3-ylmethyl)-2-(4-methoxy-benzyl)-2,8-diaza-spiro[4.5]decan-1-one dihydrochloride | 548.60 | 99.5% (HPLC) |
| 171 | 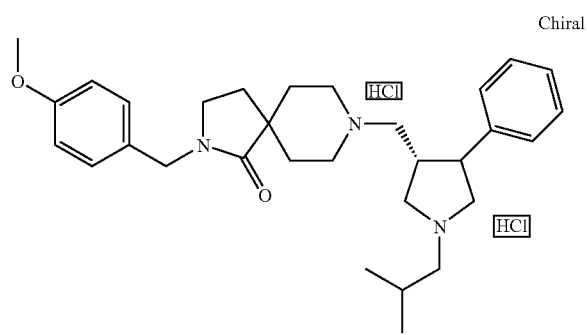 | Chiral | 8-((3S,4S)-1-Isobutyl-4-phenyl-pyrrolidin-3-ylmethyl)-2-(4-methoxy-benzyl)-2,8-diaza-spiro[4.5]decan-1-one dihydrochloride | 562.63 | 98+% (HPLC) |
| 172 | 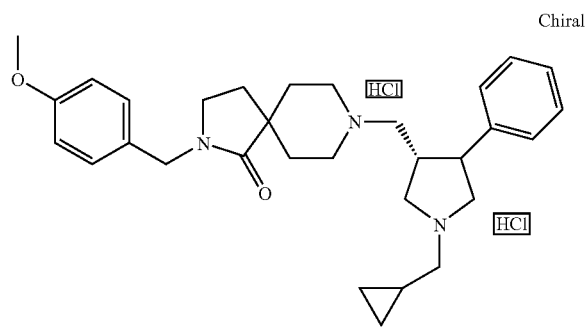 | Chiral | 8-((3S,4S)-1-Cyclopropylmethyl-4-phenyl-pyrrolidin-3-ylmethyl)-2-(4-methoxy-benzyl)-2,8-diaza-spiro[4.5]decan-1-one dihydrochloride | 560.61 | >99.9% (HPLC) |

TABLE 6-continued

| CPD # | STRUCTURE | COMPOUND NAME | MOL WT | PURITY |
|---|---|---|---|---|
| 173 | Chiral | 2-(4-Methoxy-benzyl)-8-[(3S,4S)-4-phenyl-1-(tetrahydro-pyran-4-ylmethyl)-pyrrolidin-3-ylmethyl]-2,8-diaza-spiro[4.5]decan-1-one dihydrochloride | 604.66 | 98.6% (HPLC) |
| 174 | Chiral | 8-[(3S,4S)-1-(4,4-Difluoro-cyclohexylmethyl)-4-phenyl-pyrrolidin-3-ylmethyl]-2-(4-methoxy-benzyl)-2,8-diaza-spiro[4.5]decan-1-one dihydrochloride | 638.67 | 99.5% (HPLC) |
| 175 | Chiral | 2-(4-Methanesulfonyl-benzyl)-8-((3R,4S)-1-methyl-4-phenyl-pyrrolidin-3-ylmethyl)-2,8-diaza-spiro[4.5]decan-1-one dihydrochloride | 568.61 | 98.8% (HPLC) |
| 176 | Chiral | 8-((3S,4S)-1-Isopropyl-4-phenyl-pyrrolidin-3-ylmethyl)-2-(4-methanesulfonyl-benzyl)-2,8-diaza-spiro[4.5]decan-1-one dihydrochloride | 597.66 | 98+% (HPLC) |

TABLE 6-continued

| CPD # | STRUCTURE | COMPOUND NAME | MOL WT | PURITY |
|---|---|---|---|---|
| 177 | Chiral | 8-((3S,4S)-1-Isobutyl-4-phenyl-pyrrolidin-3-ylmethyl)-2-(4-methanesulfonyl-benzyl)-2,8-diaza-spiro[4.5]decan-1-one dihydrochloride | 610.69 | 98+% (HPLC) |
| 178 | Chiral | 8-((3S,4S)-1-Cyclopropylmethyl-4-phenyl-pyrrolidin-3-ylmethyl)-2-(4-methanesulfonyl-benzyl)-2,8-diaza-spiro[4.5]decan-1-one dihydrochloride | 608.67 | 94.7% (HPLC) |
| 179 | Chiral | 2-(4-Methanesulfonyl-benzyl)-8-[(3S,4S)-4-phenyl-1-(tetrahydro-pyran-4-ylmethyl)-pyrrolidin-3-ylmethyl]-2,8-diaza-spiro[4.5]decan-1-one dihydrochloride | 652.73 | 97.1% (HPLC) |
| 180 | Chiral | 8-[(3S,4S)-1-(4,4-Difluoro-cyclohexylmethyl)-4-phenyl-pyrrolidin-3-ylmethyl]-2-(4-methanesulfonly-benzyl)-2,8-diaza-spiro[4.5]decan-1-one dihydrochloride | 686.74 | 99.1% (HPLC) |

Scheme 12

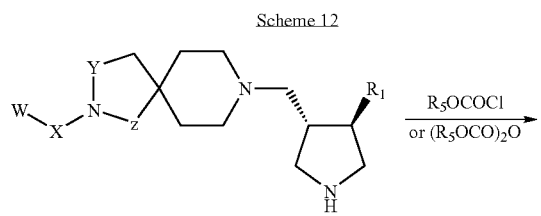

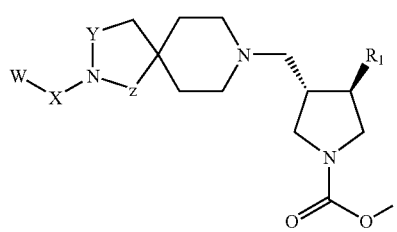

Example 13
(3S,4S)-3-[2-(4-Methoxy-benzyl)-1-oxo-2,8-diaza-spiro[4.5]dec-8-ylmethyl]-4-phenyl-pyrrolidine-1-carboxylic acid isopropyl ester hydrochloride (Compound 183)

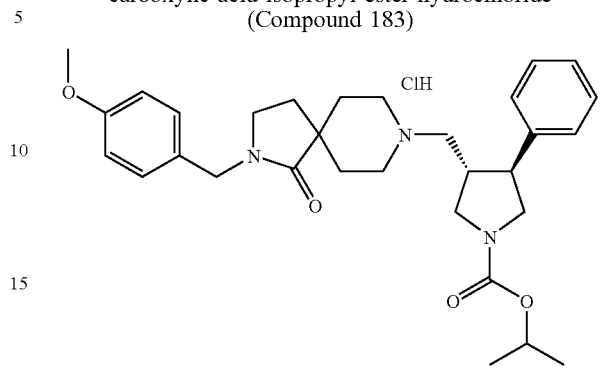

To a solution of 2-(4-methoxy-benzyl)-8-((3R,4S)-4-phenyl-pyrrolidin-3-ylmethyl)-2,8-diaza-spiro[4.5]decan-1-one (60 μmol) in anhydrous DCM (1 mL) was added isopropylchloroformate (180 μL, 1M in toluene, 180 μmol) and triethylamine (29 μL, 55 μmol). The reaction mixture was stirred overnight at room temperature. Saturated sodium bicarbonate aqueous solution was added to the reaction mixture and the aqueous layer washed with dichloromethane (3×2 mL). The organic layer was then concentrated in vacuo and purified by semi-preparative HPLC (Method D) and lyophilized to give the Compound 183 as a colorless solid (15.3 mg, 50%).

$^1$H NMR (400 MHz, DMSO-$d_6$): δ [ppm] 6.58-6.48 (m, 5H), 6.32 (d, 2H), 6.05 (d, 2H), 3.53 (s, 2H), 3.24 (m, 1H), 3.04 (m, 1H), 2.94 (s, 3H), 2.77 (m, 1H), 2.61-2.01 (m, 12H), 1.28-0.84 (m, 6H), 0.45 (m, 6H).

Table 7 of compounds illustrates some of the compounds of the present invention which were synthesized using the procedures described in scheme 12.

TABLE 7

| CPD # | STRUCTURE | | COMPOUND NAME | MOL WT | PURITY |
|---|---|---|---|---|---|
| 181 | 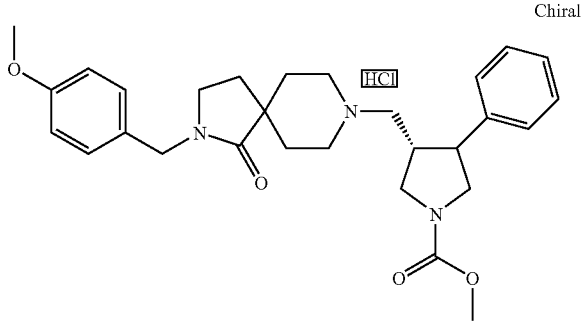 | Chiral | (3S,4S)-3-[2-(4-Methoxy-benzyl)-1-oxo-2,8-diaza-spiro[4.5]dec-8-ylmethyl]-4-phenyl-pyrrolidine-1-carboxylic acid methyl ester hydrochloride | 528.10 | >99.9% (HPLC) |
| 182 | 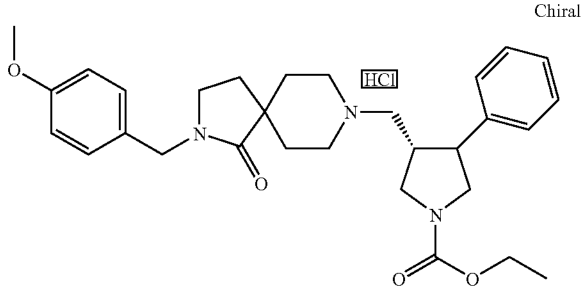 | Chiral | (3S,4S)-3-[2-(4-Methoxy-benzyl)-1-oxo-2,8-diaza-spiro[4.5]dec-8-ylmethyl]-4-phenyl-pyrrolidine-1-carboxylic acid ethyl ester hydrochloride | 542.12 | 99.8% (HPLC) |

| CPD # | STRUCTURE | | COMPOUND NAME | MOL WT | PURITY |
|---|---|---|---|---|---|
| 183 | 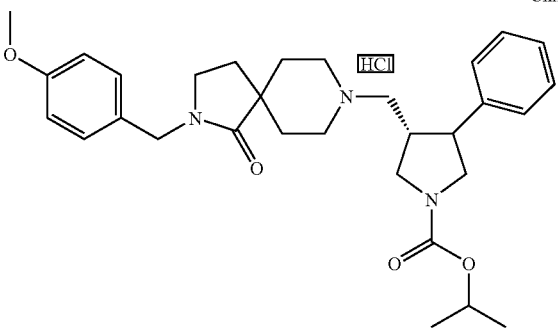 | Chiral | (3S,4S)-3-[2-(4-Methoxy-benzyl)-1-oxo-2,8-diaza-spiro[4.5]dec-8-ylmethyl]-4-phenyl-pyrrolidine-1-carboxylic acid isopropyl ester hydrochloride | 556.15 | 99.8% (HPLC) |
| 184 | 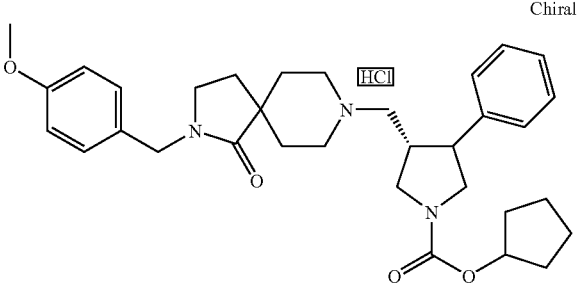 | Chiral | (3S,4S)-3-[2-(4-Methoxy-benzyl)-1-oxo-2,8-diaza-spiro[4.5]dec-8-ylmethyl]-4-phenyl-pyrrolidine-1-carboxylic acid cyclopentyl ester hydrochloride | 582.19 | 99.7% (HPLC) |
| 185 | 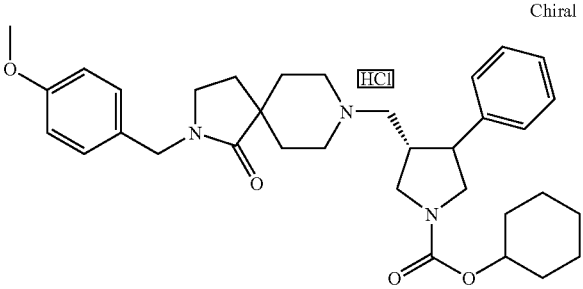 | Chiral | (3S,4S)-3-[2-(4-Methoxy-benzyl)-1-oxo-2,8-diaza-spiro[4.5]dec-8-ylmethyl]-4-phenyl-pyrrolidine-1-carboxylic acid acid cyclohexyl ester hydrochloride | 596.22 | >99.9% (HPLC) |
| 186 | 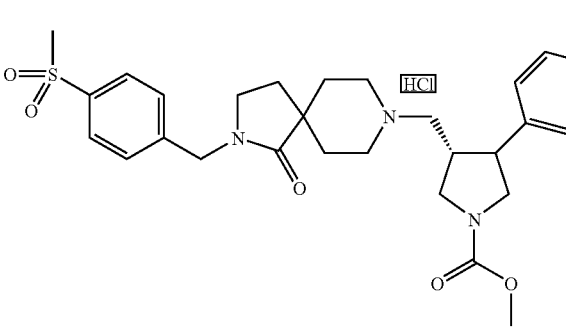 | Chiral | (3S,4S)-3-[2-(4-Methanesulfonyl-benzyl)-1-oxo-2,8-diaza-spiro[4.5]dec-8-ylmethyl]-4-phenyl-pyrrolidine-1-carboxylic acid methyl ester hydrochloride | 576.16 | 99.3% (HPLC) |

TABLE 7-continued

| CPD # | STRUCTURE | COMPOUND NAME | MOL WT | PURITY |
|---|---|---|---|---|
| 187 | 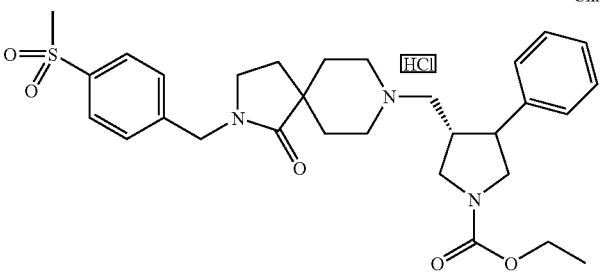 Chiral | (3S,4S)-3-[2-(4-Methanesulfonyl-benzyl)-1-oxo-2,8-diaza-spiro[4.5]dec-8-yimethyl]-4-phenyl-pyrrolidine-1-carboxylic acid ethyl ester hydrochloride | 590.19 | >99.9% (HPLC) |
| 188 | 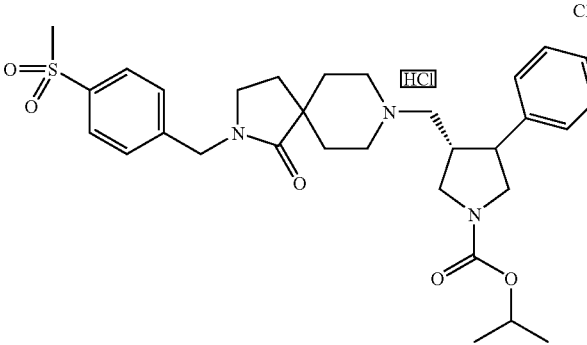 Chiral | (3S,4S)-3-[2-(4-Methanesulfonyl-benzyl)-1-oxo-2,8-diaza-spiro[4.5]dec-8-ylmethyl]-4-phenyl-pyrrolidine-1-carboxylic acid isopropyl ester hydrochloride | 604.21 | >99.9% (HPLC) |
| 189 | 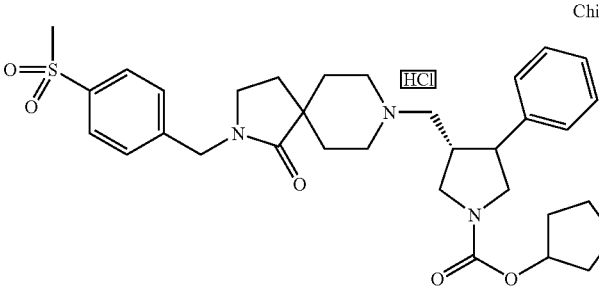 Chiral | (3S,4S)-3-[2-(4-Methanesulfonyl-benzyl)-1-oxo-2,8-diaza-spiro[4.5]dec-8-ylmethyl]-4-phenyl-pyrrolidine-1-carboxylic acid cyclopentyl ester hydrochloride | 630.25 | 99.7% (HPLC) |
| 190 | 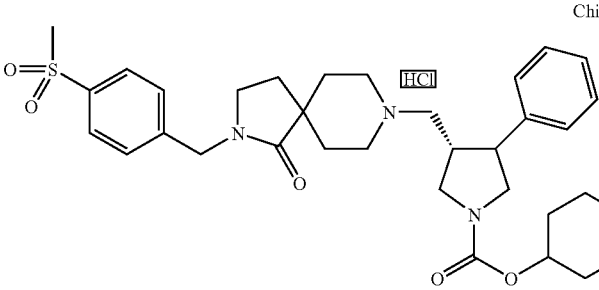 Chiral | (3S,4S)-3-[2-(4-Methanesulfonyl-benzyl)-1-oxo-2,8-diaza-spiro[4.5]dec-8-ylmethyl]-4-phenyl-pyrrolidine-1-carboxylic acid cyclohexyl ester hydrochloride | 644.28 | >99.9% (HPLC) |

Scheme 13

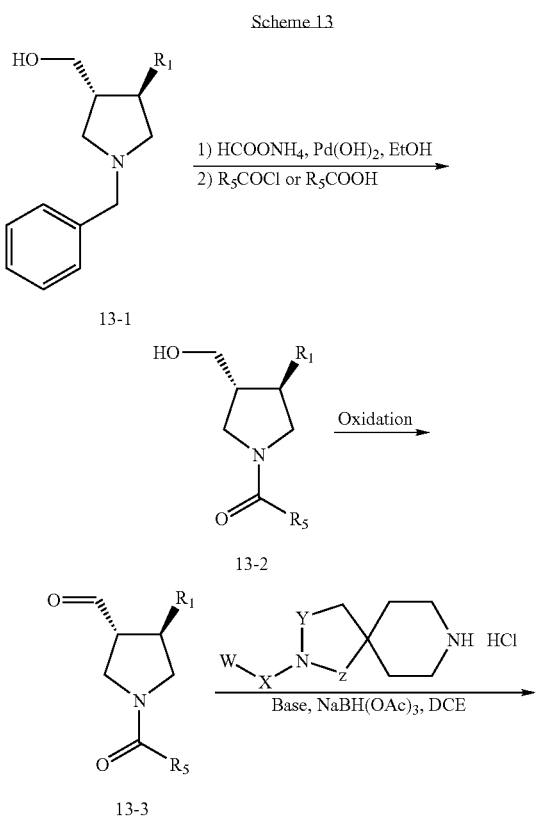

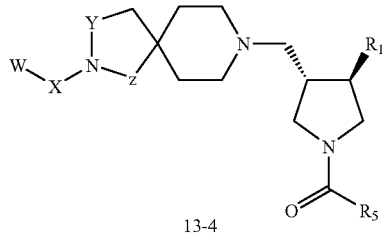

General procedure: the amino alcohol 13-1 is deprotected by hydrogenolysis as described in Preparation 9 (Step 4) and then condensed with acid chloride $R_5COCl$ in solvent such as DCM in presence of a base such as triethylamine or diisopropylethylamine, or condensed with a carboxylic acid $R_5COOH$ in solvent such as DMF with coupling agents such as HOBt, DIC, HATU, BOP, PYBOP, to provide acylated compound 13-2. The alcohol 13-2 is therefore oxidized using convential methods such as Swern reaction (see Step 6 of Preparation 9) and condensed with spiropiperidines using standard reductive amination reaction as described for Example 7 and leading to final compound 13-4.

Table 8 of compounds illustrates some of the compounds of the present invention which can be synthesized using the procedures described in scheme 13.

TABLE 8

| CPD # | STRUCTURE | COMPOUND NAME | MOL WT |
|---|---|---|---|
| 191 | Chiral | 8-[(3S,4S)-1-(2-Cyclopropyl-acetyl)-4-phenyl-pyrrolidin-3-ylmethyl]-2-(4-fluoro-benzyl)-2,8-diaza-spiro[4.5]decan-1-one hydrochloride | 540.13 |
| 192 | Chiral | 2-(4-Chloro-benzyl)-8-[(3S,4S)-1-(2-cyclopropyl-acetyl)-4-phenyl-pyrrolidin-3-ylmethyl]-2,8 diaza-spiro[4.5]decan-1-one hydrochloride | 556.58 |

TABLE 8-continued

| CPD # | STRUCTURE | COMPOUND NAME | MOL WT |
|---|---|---|---|
| 193 | Chiral, HCl | 4-{8-[(3S,4S)-1-(2-Cyclopropyl-acetyl)-4-phenyl-pyrrolidin-3-ylmethyl]-1-oxo-2,8-diaza-spiro[4.5]dec-2-ylmethyl}-benzonitrile hydrochloride | 547.15 |
| 194 | Chiral, HCl | 8-[(3S,4S)-1-(2-Cyclopropyl-acetyl)-4-phenyl-pyrrolidin-3-ylmethyl]-2-(4-difluoromethoxy-benzyl)-2,8-diaza-spiro[4.5]decan-1-one hydrochloride | 588.14 |
| 195 | Chiral, HCl | 8-[(3S,4S)-1-(2-Cyclopropyl-acetyl)-4-phenyl-pyrrolidin-3-ylmethyl]-2-(4-trifluoromethoxy-benzyl)-2,8-diaza-spiro[4.5]decan-1-one hydrochloride | 606.13 |
| 196 | Chiral, HCl | 8-[(3S,4S)-1-(2-Cyclopropyl-acetyl)-4-phenyl-pyrrolidin-3-ylmethyl]-2-(4-trifluoromethyl-benzyl)-2,8-diaza-spiro[4.5]decan-1-one hydrochloride | 590.13 |
| 197 | Chiral, HCl | 8-[(3S,4S)-1-(2-Cyclopropyl-acetyl)-4-phenyl-pyrrolidin-3-ylmethyl]-2-(4-pyrazol-1-yl-benzyl)-2,8-diaza-spiro[4.5]decan-1-one hydrochloride | 588.2 |

TABLE 8-continued

| CPD # | STRUCTURE | COMPOUND NAME | MOL WT |
|---|---|---|---|
| 198 | 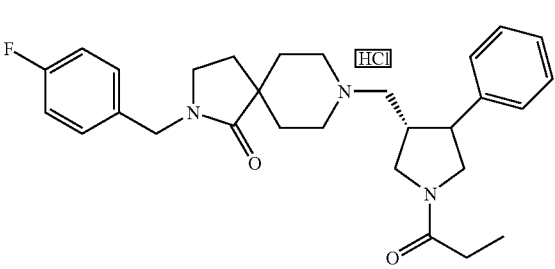 Chiral | 2-(4-Fluoro-benzyl)-8-((3S,4S)-4-phenyl-1-propionyl-pyrrolidin-3-ylmethyl)-2,8-diaza-spiro[4.5]decan-1-one hydrochloride | 514.09 |
| 199 | 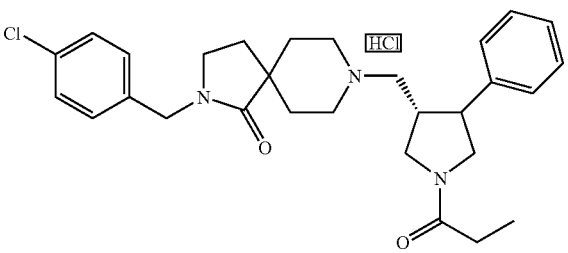 Chiral | 2-(4-Chloro-benzyl)-8-((3S,4S)-4-phenyl-1-propionyl-pyrrolidin-3-ylmethyl)-2,8-diaza-spiro[4.5]decan-1-one hydrochloride | 530.54 |
| 200 | 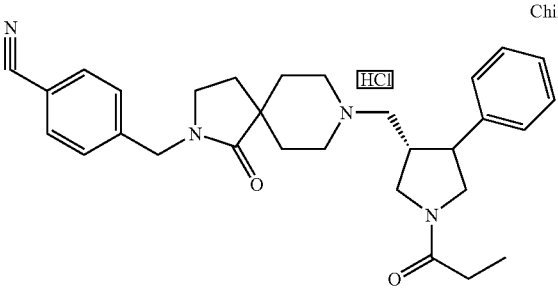 Chiral | 4-[1-Oxo-8-((3S,4S)-4-phenyl-1-propionyl-pyrrolidin-3-ylmethyl)-2,8-diaza-spiro[4.5]dec-2-ylmethyl]-benzonitrile hydrochloride | 521.11 |
| 201 | 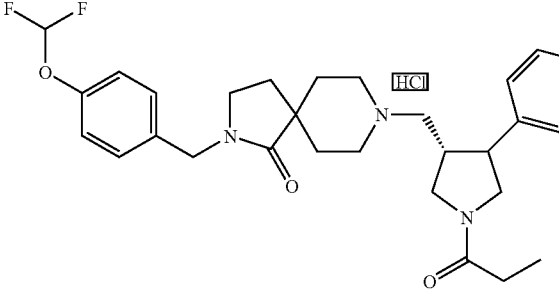 Chiral | 2-(4-Difluoromethoxy-benzyl)-8-((3S,4S)-4-phenyl-1-propionyl-pyrrolidin-3-ylmethyl)-2,8-diaza-spiro[4.5]decan-1-one hydrochloride | 562.1 |
| 202 | 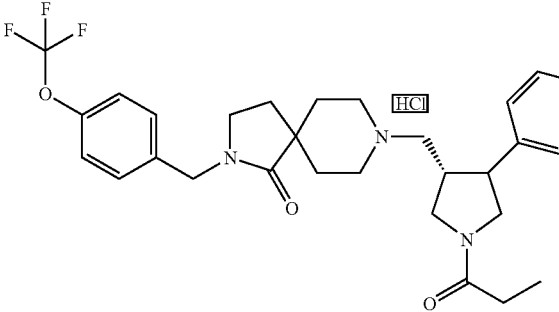 Chiral | 8-((3S,4S)-4-Phenyl-1-propionyl-pyrrolidin-3-ylmethyl)-2-(4-trifluoromethoxy-benzyl)-2,8-diaza-spiro[4.5]decan-1-one hydrochloride | 580.09 |

TABLE 8-continued

| CPD # | STRUCTURE | | COMPOUND NAME | MOL WT |
|---|---|---|---|---|
| 203 | 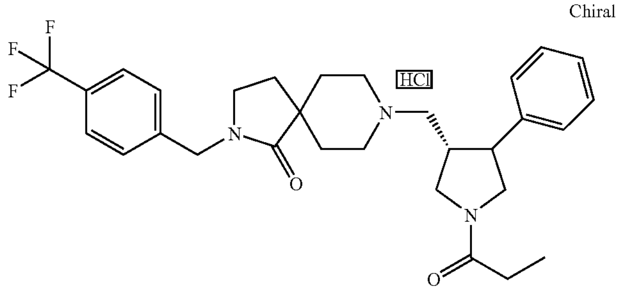 | Chiral | 8-((3S,4S)-4-Phenyl-1-propionyl-pyrrolidin-3-ylmethyl)-2-(4-trifluoromethyl-benzyl)-2,8-diaza-spiro[4.5]decan-1-one hydrochloride | 564.1 |
| 204 | 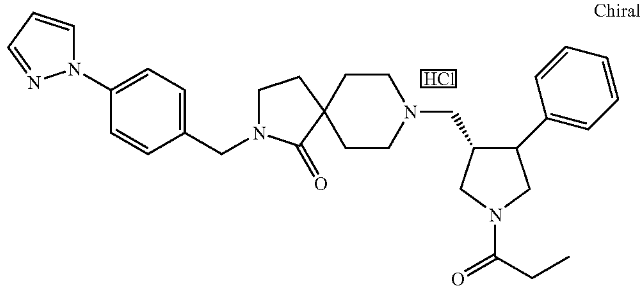 | Chiral | 8-((3S,4S)-4-Phenyl-1-propionyl-pyrrolidin-3-ylmethyl)-2-(4-pyrazol-1-yl-benzyl)-2,8-diaza-spiro[4.5]decan-1-one hydrochloride | 562.16 |

Example 14

The following assay methods are suitable for evaluating the compounds of the invention.

Chemokine Binding assay: Membranes (1 μg/well) from human embryonic kidney (HEK-293) cells expressing human CCR5 were incubated with 0.1 nM $^{125}$I-labeled MIP-1α (Amersham) in the presence of varying concentrations of a test compound (10000-0.01 nM) in buffer (50 mM Hepes, pH 7.3/5 mM MgCl$_2$/1 mM CaCl$_2$/0.5% BSA) for 90 min at room temperature. Reaction mixtures (100 μL) were filtered through Multiscreen GFB filters (Millipore) and washed six times with cold wash buffer (50 mM Hepes, pH 7.3/0.5 M NaCl, 0.1% BSA). Bound $^{125}$I-MIP-1α was quantitated by liquid scintillation counting. The nonspecific binding of $^{125}$I-labeled MIP-1α to the membrane was determined based on the radioactivity from the wells added with 100 nM non-radiolabeled MIP-1α. IC$_{50}$ and K$_D$ values were calculated by using GRAPHPAD PRISM software (Intuitive Software for Science, San Diego).

HIV-1 Replication in PBMC Cultures: Isolated PBMCs were stimulated in vitro with 5 μg/ml phytohemaglutinin and 50 units/ml IL-2 for 3 days. The cells were resuspended at 4×10$^6$/ml in complete medium (RPMI, 10% FBS/50 units/ml IL-2), seeded into 96-well plates (2×10$^5$/well), incubated with inhibitor for 1 h at 37° C., and infected in triplicate with 25-100 tissue culture 50% infective dose (TCID$_{50}$) per well of the R5 HIV-1$_{JR-FL}$ strain for 3-4 h. The cells were washed twice in PBS to remove residual virus and cultured in the presence of inhibitor for 4-6 days. HIV-1 replication was determined by the presence of viral RT activity in harvested supernatant fluid. The IC$_{50}$ values for the virus were determined by using GRAPHPAD PRISM software.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound according to formula (I):

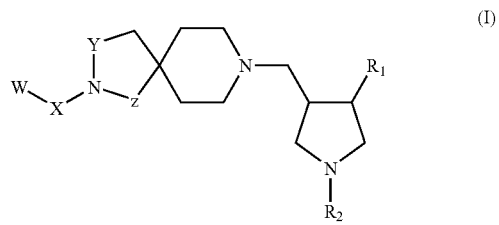

(I)

or a pharmaceutically acceptable salt thereof, wherein

X, Y and Z are each independently CH$_2$, C=O or CR$_3$R$_4$;

W is H, optionally substituted C$_{1-10}$ alkyl, optionally substituted C$_{2-10}$ alkenyl, optionally substituted C$_{2-10}$ alkynyl, optionally substituted C$_{6-12}$ aryl, optionally substituted 3 to 10 membered heterocycle, optionally substituted C$_{6-12}$ aralkyl or optionally substituted 3 to 10 membered heteroaralkyl;

R$_1$ is H, optionally substituted C$_{1-10}$ alkyl, optionally substituted C$_{2-10}$ alkenyl, optionally substituted C$_{2-10}$ alkynyl, optionally substituted C$_{6-12}$ aryl, optionally substituted 3 to 10 membered heterocycle, optionally substituted C$_{6-12}$ aralkyl or optionally substituted 3 to 10 membered heteroaralkyl;

R$_2$ is H,

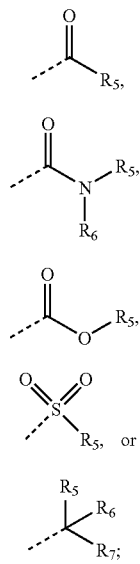

R₃ and R₄ are each independently H, optionally substituted $C_{1-10}$ alkyl, optionally substituted $C_{2-10}$ alkenyl, optionally substituted $C_{2-10}$ alkynyl, or optionally substituted $C_{6-12}$ aryl;

R₅, R₆ and R₇ are each independently H, optionally substituted $C_{1-10}$ alkyl, optionally substituted $C_{2-10}$ alkenyl, optionally substituted $C_{2-10}$ alkynyl, optionally substituted $C_{6-12}$ aryl, optionally substituted 3 to 10 membered heterocycle, optionally substituted $C_{6-12}$ aralkyl or optionally substituted 3 to 10 membered heteroaralkyl; or R₅ and R₆ can be taken together to form an optionally substituted 3 to 10 membered heterocycle.

2. A compound according to claim 1, wherein

X, Y and Z are each independently chosen from $CH_2$, C=O or $CR_3R_4$;

W is chosen from H, $C_{1-6}$ alkyl, $C_{6-12}$ aryl, 3 to 10 membered heterocycle, $C_{6-12}$ aralkyl or $C_{3-10}$ heteroaralkyl;

R₁ is chosen from H, $C_{1-6}$ alkyl, $C_{6-12}$ aryl, 3 to 10 membered heterocycle, $C_{6-12}$ aralkyl or $C_{3-10}$ heteroaralkyl;

R₂ is chosen from H or

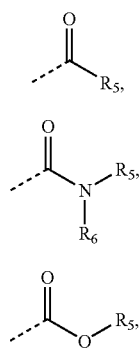

R₃ and R₄ are each independently chosen from H, $C_{1-6}$ alkyl or $C_{6-12}$ aryl;

R₅ is chosen from H, $C_{1-10}$ alkyl, $C_{6-12}$ aryl, 3 to 10 membered heterocycle, $C_{6-12}$ aralkyl or 3 to 10 membered heteroaralkyl, and R₆ is H or $C_{1-10}$ alkyl, or R₅ and R₆ can be taken together to form a 3 to 10 membered heterocycle; and R₇ is H or $C_{1-10}$ alkyl.

3. A compound according to claim 1, wherein said compound is of formula (Ia):

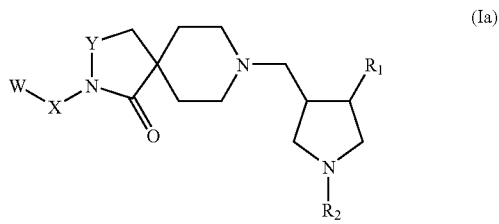

or a pharmaceutically acceptable salt thereof.

4. A compound according to claim 1, wherein said compound is of formula (Ib):

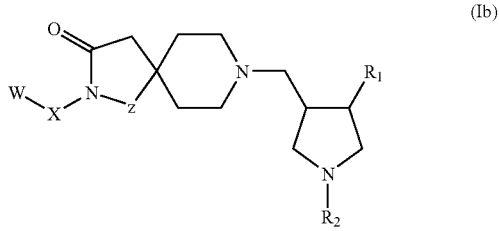

or a pharmaceutically acceptable salt thereof.

5. A compound according to claim 1, wherein said compound is of formula (Ic):

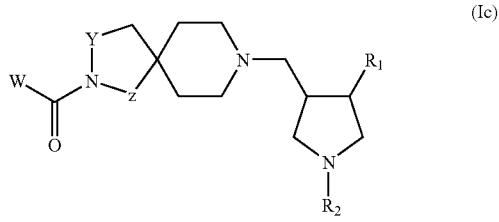

or pharmaceutically acceptable salt thereof.

6. A compound according to claim 1, wherein said compound is of formula (Id):

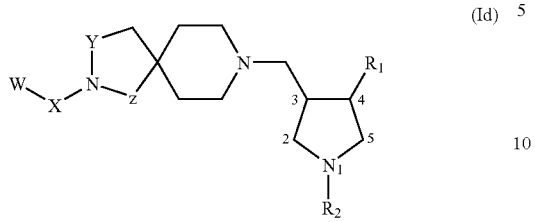

(Id)

or pharmaceutically acceptable salt thereof.

7. A compound according to claim 1, wherein W is optionally substituted $C_{6-12}$ aryl or optionally substituted 3 to 10 membered heterocycle.

8. A compound according to claim 1, wherein W is optionally substituted $C_{6-12}$ aryl.

9. A compound according to claim 1, wherein W is optionally substituted 3 to 10 membered heterocycle.

10. A compound according to claim 1, wherein W is phenyl, phenyl substituted with halogen, phenyl substituted with Br, phenyl substituted with F, phenyl substituted with Cl, phenyl substituted with a $C_{1-3}$ alkoxy, phenyl substituted with methoxy, phenyl substituted with $SO_2C_{1-3}$ alkyl, phenyl substituted with methanesulfonyl, phenyl substituted with difluoromethoxy, phenyl substituted with trifluoromethoxy, phenyl substituted with trifluoromethyl, phenyl substituted with CN, phenyl substituted with pyrrazoyl, phenyl substituted in the para (p) position, or pyridinyl.

11. A compound according to claim 1, wherein $R_1$ is optionally substituted $C_{6-12}$ aryl.

12. A compound according to claim 1, wherein $R_1$ is phenyl.

13. A compound according to claim 1, wherein $R_2$ is

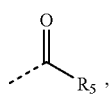

(II)

and $R_5$ is pyridinyl, furanyl, thiophene, methyl, ethyl, isopropyl, cyclopropyl, cyclobutyl, cyclopentyl, cyclohexyl, cycloheptyl, 4,4-difluorocyclohexyl, $CH_2$-cyclopropyl, $CH_2$-cyclobutyl, $CH_2$-cyclopentyl, $CH_2$-cyclohexyl, phenyl, phenyl substituted with at least one methyl, phenyl substituted with at least one halogen, phenyl substituted with at least one Cl, phenyl substituted with at least one Br, phenyl substituted with at least one F, phenyl substituted with at least one methoxy, benzyl, benzyl substituted with at least one methyl, benzyl substituted with at least one halogen, benzyl substituted with at least one Cl, benzyl substituted with at least one Br, or benzyl substituted with at least one F, benzyl substituted with at least one methoxy.

14. A compound according to claim 1, wherein $R_2$ is

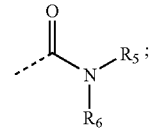

(III)

$R_5$ is cyclopropyl, cyclopentyl, phenyl
$R_6$ is H;
$R_5$ and $R_6$ are methyl; and
$R_5$ and $R_6$ are taken together to form a morpholine, a pyrrolidine, or a 3,3-difluoropyrrolidine.

15. A compound according to claim 1, wherein $R_2$ is

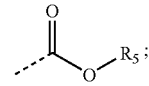

(IV)

and
$R_5$ is methyl, ethyl, isopropyl, cyclopentyl, cyclohexyl and tert-butyl.

16. A compound according to claim 1, wherein $R_2$ is

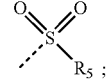

(V)

and
$R_5$ is ethyl, isopropyl, cyclopropyl and phenyl.

17. A compound according to claim 1, wherein $R_2$ is

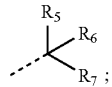

(VI)

wherein:
$R_5$, $R_6$ and $R_7$ are each H; or
$R_5$ is isopropyl, cyclopropyl, cyclohexyl, tetrahydropyrane, 4,4-difluorocyclohexyl, phenyl and $R_6$ and $R_7$ are H; or
$R_5$ and $R_6$ are methyl and $R_7$ are H.

18. A compound according to claim 1, wherein $R_3$ is H or $C_{1-10}$ alkyl.

19. A compound according to claim 1, wherein $R_3$ is H.

20. A compound according to claim 1, wherein said compound is selected from:
3-(RS)-[2-(4-Bromo-benzyl)-1-oxo-2,8-diaza-spiro[4.5]dec-8-ylmethyl]-4-(SR)-phenylpyrrolidine-1-carboxylic acid tert-butyl ester
8-(1-Benzoyl-4-(SR)-phenylpyrrolidin-3-(RS)-ylmethyl)-2-(4-bromo-benzyl)-2,8-diaza-spiro[4.5]decan-1-one
2-(4-Bromobenzyl)-8-(4-(SR)-phenylpyrrolidin-3-(RS)-ylmethyl)-2,8-diaza-spiro[4.5]decan-1-one 3-(RS)-[2-(4-Bromobenzyl)-3-oxo-2,8-diaza-spiro[4.5]
dec-8-ylmethyl]-4-(SR)-phenylpyrrolidine-1-carboxylic acid tert-butyl ester 2-(4-Bromobenzyl)-8-(4-(SR)-phenyl-1-phenylacetylpyrrolidin-3-(RS)-ylmethyl)-2,8-diaza-spiro[4.5]decan-1-one 3-(RS)-[2-(4-Methanesulfonylbenzyl)-1-oxo-2,8-diazaspiro[4.5]dec-8-ylmethyl]-4-(SR)-phenylpyrrolidine-1-carboxylic acid tert-butyl ester 3-(RS)-[2-(4-Methoxybenzyl)-1-oxo-2,8-diaza-spiro[4.5]
dec-8-ylmethyl]-4-(SR)-phenylpyrrolidine-1-carboxylic acid tert-butyl ester 8-(1-Acetyl-4-(SR)-phenylpyrrolidin-3-(RS)-ylmethyl)-2-(4-bromobenzyl)-2,8-diaza-spiro[4.5]decan-1-one 2-(4-Bromobenzyl)-8-(1-cyclopropanecarbonyl-4-(SR)-phenylpyrrolidin-3-(RS)-ylmethyl)-2,8-diaza-spiro[4.5]decan-1-one 2-(4-Bromobenzyl)-8-(1-isobutyryl-4-(SR)-phenylpyrrolidin-3-(RS)-ylmethyl)-2,8-diaza-spiro[4.5]decan-1-one 2-(4-Bromobenzyl)-8-[1-(3-methyl-butyryl)-4-(SR)-phenylpyrrolidin-3-(RS)-ylmethyl]-2,8-diaza-spiro[4.5]decan-1-one 2-(4-Bromobenzyl)-8-[1-(2-chloro-benzoyl)-4-(SR)-phenylpyrrolidin-3-(RS)-ylmethyl]-2,8-diaza-spiro[4.5]decan-1-one 2-(4-Bromobenzyl)-8-[1-(2-methoxybenzoyl)-4-(SR)-phenylpyrrolidin-3-(RS)-ylmethyl]-2,8-diaza-spiro[4.5]decan-1-one 2-(4-Bromobenzyl)-8-[4-(SR)-phenyl-1-(pyridine-2-carbonyl)-pyrrolidin-3-(RS)-ylmethyl]-2,8-diaza-spiro[4.5]decan-1-one 2-(4-Bromobenzyl)-8-[1-(3-chlorobenzoyl)-4-(SR)-phenylpyrrolidin-3-(RS)-ylmethyl]-2,8-diaza-spiro[4.5]decan-1-one 2-(4-Bromobenzyl)-8-[1-(3-methoxybenzoyl)-4-(SR)-phenylpyrrolidin-3-(RS)-ylmethyl]-2,8-diaza-spiro[4.5]decan-1-one 2-(4-Bromobenzyl)-8-[4-(SR)-phenyl-1-(pyridine-3-carbonyl)-pyrrolidin-3-(RS)-ylmethyl]-2,8-diaza-spiro[4.5]decan-1-one 2-(4-Bromobenzyl)-8-[1-(4-chlorobenzoyl)-4-(SR)-phenyl-pyrrolidin-3-(RS)-ylmethyl]-2,8-diaza-spiro[4.5]decan-1-one 2-(4-Bromobenzyl)-8-[1-(4-methoxybenzoyl)-4-(SR)-phenylpyrrolidin-3-(RS)-ylmethyl]-2,8-diaza-spiro[4.5]decan-1-one 2-(4-Bromobenzyl)-8-[4-(SR)-phenyl-1-(pyridine-4-carbonyl)-pyrrolidin-3-(RS)-ylmethyl]-2,8-diaza-spiro[4.5]decan-1-one 2-(4-Bromobenzyl)-8-[1-(3,4-dichlorobenzoyl)-4-(SR)-phenylpyrrolidin-3-(RS)-ylmethyl]-2,8-diaza-spiro[4.5]decan-1-one 2-(4-Bromobenzyl)-8-[1-(3,4-dimethoxybenzoyl)-4-(SR)-phenylpyrrolidin-3-(RS)-ylmethyl]-2,8-diaza-spiro[4.5]decan-1-one 2-(4-Bromobenzyl)-8-{1-[2-(2-chlorophenyl)-acetyl]-4-(SR)-phenylpyrrolidin-3-(RS)-ylmethyl}-2,8-diaza-spiro[4.5]decan-1-one 2-(4-Bromobenzyl)-8-{1-[2-(2-methoxyphenyl)-acetyl]-4-(SR)-phenylpyrrolidin-3-(RS)-ylmethyl}-2,8-diaza-spiro[4.5]decan-1-one 2-(4-Bromobenzyl)-8-{1-[2-(3-chlorophenyl)-acetyl]-4-(SR)-phenylpyrrolidin-3-(RS)-ylmethyl}-2,8-diaza-spiro[4.5]decan-1-one 2-(4-Bromo-benzyl)-8-{1-[2-(3-methoxy-phenyl)-acetyl]-4-(SR)-phenyl-pyrrolidin-3-(RS)-ylmethyl}-2,8-diaza-spiro[4.5]decan-1-one 2-(4-Bromobenzyl)-8-[4-(SR)-phenyl-1-(2-pyridin-3-yl-acetyl)-pyrrolidin-3-(RS)-ylmethyl]-2,8-diaza-spiro[4.5]decan-1-one 2-(4-Bromobenzyl)-8-{1-[2-(4-methoxyphenyl)-acetyl]-4-(SR)-phenylpyrrolidin-3-(RS)-ylmethyl}-2,8-diaza-spiro[4.5]decan-1-one 2-(4-Bromobenzyl)-8-{1-[2-(3,4-dichlorophenyl)-acetyl]-4-(SR)-phenylpyrrolidin-3-(RS)-ylmethyl}-2,8-diaza-spiro[4.5]decan-1-one 2-(4-Bromobenzyl)-8-[4-(SR)-phenyl-1-(tetrahydro-pyran-4-carbonyl)-pyrrolidin-3-(RS)-ylmethyl]-2,8-diaza-spiro[4.5]decan-1-one 2-(4-Bromobenzyl)-8-(1-cyclopentanecarbonyl-4-(SR)-phenyl-pyrrolidin-3-(RS)-ylmethyl)-2,8-diaza-spiro[4.5]decan-1-one 2-(4-Bromobenzyl)-8-(1-cyclobutanecarbonyl-4-(SR)-phenyl-pyrrolidin-3-(RS)-ylmethyl)-2,8-diaza-spiro[4.5]decan-1-one 2-(4-Bromobenzyl)-8-(1-cycloheptanecarbonyl-4-(SR)-phenylpyrrolidin-3-(RS)-ylmethyl)-2,8-diaza-spiro[4.5]decan-1-one 2-(4-Bromobenzyl)-8-[1-(2-cyclohexyl-acetyl)-4-(SR)-phenylpyrrolidin-3-(RS)-ylmethyl]-2,8-diaza-spiro[4.5]decan-1-one 2-(4-Bromobenzyl)-8-[1-(2-cyclopentyl-acetyl)-4-(SR)-phenylpyrrolidin-3-(RS)-ylmethyl]-2,8-diaza-spiro[4.5]decan-1-one 2-(4-Bromobenzyl)-8-[1-(furan-2-carbonyl)-4-(SR)-phenylpyrrolidin-3-(RS)-ylmethyl]-2,8-diaza-spiro[4.5]decan-1-one 2-(4-Bromobenzyl)-8-[1-(2-ethyl-butyryl)-4-(SR)-phenylpyrrolidin-3-(RS)-ylmethyl]-2,8-diaza-spiro[4.5]decan-1-one 2-(4-Bromobenzyl)-8-[4-(SR)-phenyl-1-(thiophene-2-carbonyl)-pyrrolidin-3-(RS)-ylmethyl]-2,8-diaza-spiro[4.5]decan-1-one 2-(4-Bromobenzyl)-8-{1-[2-(3,4-dimethoxyphenyl)-acetyl]-4-(SR)-phenylpyrrolidin-3-(RS)-ylmethyl}-2,8-diaza-spiro[4.5]decan-1-one 2-(4-Bromobenzyl)-8-(1-cyclohexanecarbonyl-4-(SR)-phenylpyrrolidin-3-(RS)-ylmethyl)-2,8-diaza-spiro[4.5]decan-1-one 2-(4-Bromobenzyl)-8-[4-(SR)-phenyl-1-(3-phenyl-propionyl)-pyrrolidin-3-(RS)-ylmethyl]-2,8-diaza-spiro[4.5]decan-1-one 2-(4-Methoxybenzyl)-8-(4-(SR)-phenylpyrrolidin-3-(RS)-ylmethyl)-2,8-diaza-spiro[4.5]decan-1-one 2-(4-Methanesulfonylbenzyl)-8-(4-(SR)-phenylpyrrolidin-3-(RS)-ylmethyl)-2,8-diaza-spiro[4.5]decan-1-one 2-(4-Bromobenzyl)-8-[1-(2-cyclopropyl-acetyl)-4-(SR)-phenylpyrrolidin-3-(RS)-ylmethyl]-2,8-diaza-spiro[4.5]decan-1-one 8-(1-Acetyl-4-(SR)-phenylpyrrolidin-3-(RS)-ylmethyl)-2-(4-methoxybenzyl)-2,8-diaza-spiro[4.5]decan-1-one 2-(4-Methoxybenzyl)-8-(4-(SR)-phenyl-1-propionyl-pyrrolidin-3-(RS)-ylmethyl)-2,8-diaza-spiro[4.5]decan-1-one 8-[1-(2-Methoxy-acetyl)-4-(SR)-phenylpyrrolidin-3-(RS)-ylmethyl]-2-(4-methoxybenzyl)-2,8-diaza-spiro[4.5]decan-1-one 2-(4-Methoxybenzyl)-8-[1-(3-methoxypropionyl)-4-(SR)-phenylpyrrolidin-3-(RS)-ylmethyl]-2,8-diaza-spiro[4.5]decan-1-one 8-(1-Cyclopropanecarbonyl-4-(SR)-phenylpyrrolidin-3-(RS)-ylmethyl)-2-(4-methoxy-benzyl)-2,8-diaza-spiro[4.5]decan-1-one 8-(1-Cyclobutanecarbonyl-4-(SR)-phenylpyrrolidin-3-(RS)-ylmethyl)-2-(4-methoxybenzyl)-2,8-diaza-spiro[4.5]decan-1-one 8-(1-Cyclopentanecarbonyl-4-(SR)-phenylpyrrolidin-3-(RS)-ylmethyl)-2-(4-methoxybenzyl)-2,8-diaza-spiro[4.5]decan-1-one 8-(1-Cyclohexanecarbonyl-4-(SR)-phenylpyrrolidin-3-(RS)-ylmethyl)-2-(4-methoxybenzyl)-2,8-diaza-spiro[4.5]decan-1-one 8-(1-Cycloheptanecarbonyl-4-(SR)-phenylpyrrolidin-3-(RS)-ylmethyl)-2-(4-methoxybenzyl)-2,8-diaza-spiro[4.5]decan-1-one 2-(4-Methoxybenzyl)-8-[4-(SR)-phenyl-1-(tetrahydro-pyran-4-carbonyl)-pyrrolidin-3-(RS)-ylmethyl]-2,8-diaza-spiro[4.5]decan-1-one 8-[1-(2-Cyclopropyl-acetyl)-4-(SR)-phenylpyrrolidin-3-(RS)-ylmethyl]-2-(4-methoxybenzyl)-2,8-diaza-spiro[4.5]decan-1-one 8-[1-(2-Cyclopentyl-acetyl)-4-(SR)-phenylpyrrolidin-3-(RS)-ylmethyl]-2-(4-methoxybenzyl)-2,8-diaza-spiro[4.5]decan-1-one 8-[1-(2-Cyclohexyl-acetyl)-4-(SR)-phenylpyrrolidin-3-(RS)-ylmethyl]-2-(4-methoxybenzyl)-2,8-diaza-spiro[4.5]decan-1-one 8-(1-Isobutyryl-4-(SR)-phenylpyrrolidin-3-(RS)-ylmethyl)-2-(4-methoxybenzyl)-2,8-diaza-spiro[4.5]decan-1-one 2-(4-Methoxybenzyl)-8-[1-(3-methyl-butyryl)-4-(SR)-phenylpyrrolidin-3-(RS)-ylmethyl]-2,8-diaza-spiro[4.5]decan-1-one 8-[1-(2-Ethyl-butyryl)-4-(SR)-phenylpyrrolidin-3-(RS)-ylmethyl]-2-(4-methoxybenzyl)-2,8-diaza-spiro[4.5]decan-1-one 8-[1-(2-Chlorobenzoyl)-4-(SR)-phenylpyrrolidin-3-(RS)-ylmethyl]-2-(4-methoxybenzyl)-2,8-diaza-spiro[4.5]decan-1-one 8-[1-(2,6-Dichlorobenzoyl)-4-(SR)-phenylpyrrolidin-3-(RS)-ylmethyl]-2-(4-methoxybenzyl)-2,8-diaza-spiro[4.5]decan-1-one 8-[1-(2-Methoxybenzoyl)-4-(SR)-phenylpyrrolidin-3-(RS)-ylmethyl]-2-(4-methoxybenzyl)-2,8-diaza-spiro[4.5]decan-1-one 2-(4-Methoxybenzyl)-8-[4-(SR)-phenyl-1-(pyridine-2-carbonyl)-pyrrolidin-3-(RS)-ylmethyl]-2,8-diaza-spiro[4.5]decan-1-one 8-[1-(2-Fluorobenzoyl)-4-(SR)-phenylpyrrolidin-3-(RS)-ylmethyl]-2-(4-methoxybenzyl)-2,8-diaza-spiro[4.5]decan-1-one 2-(4-Methoxybenzyl)-8-[1-(2-methylbenzoyl)-4-(SR)-phenylpyrrolidin-3-(RS)-ylmethyl]-2,8-diaza-spiro[4.5]decan-1-one 2-(4-Methoxybenzyl)-8-[4-(SR)-phenyl-1-(pyridine-3-carbonyl)-pyrrolidin-3-(RS)-ylmethyl]-2,8-diaza-spiro[4.5]decan-1-one 2-(4-Methoxybenzyl)-8-[4-(SR)-phenyl-1-(pyridine-4-carbonyl)-pyrrolidin-3-(RS)-ylmethyl]-2,8-diaza-spiro[4.5]decan-1-one 8-[1-(Furan-2-carbonyl)-4-(SR)-phenylpyrrolidin-3-(RS)-ylmethyl]-2-(4-methoxybenzyl)-2,8-diaza-spiro[4.5]decan-1-one 2-(4-Methoxybenzyl)-8-[4-(SR)-phenyl-1-(thiophene-2-carbonyl)-pyrrolidin-3-(RS)-ylmethyl]-2,8-diaza-spiro[4.5]decan-1-one 8-(1-Acetyl-4-(SR)-phenylpyrrolidin-3-(RS)-ylmethyl)-2-(4-methanesulfonylbenzyl)-2,8-diaza-spiro[4.5]decan-1-one 2-(4-Methanesulfonylbenzyl)-8-(4-(SR)-phenyl-1-propionyl-pyrrolidin-3-(RS)-ylmethyl)-2,8-diaza-spiro[4.5]decan-1-one 2-(4-Methanesulfonylbenzyl)-8-[1-(2-methoxy-acetyl)-4-(SR)-phenylpyrrolidin-3-(RS)-ylmethyl]-2,8-diaza-spiro[4.5]decan-1-one 2-(4-Methanesulfonylbenzyl)-8-[1-(3-methoxy-propionyl)-4-(SR)-phenylpyrrolidin-3-(RS)-ylmethyl]-2,8-diaza-spiro[4.5]decan-1-one 8-(1-Cyclopropanecarbonyl-4-(SR)-phenylpyrrolidin-3-(RS)-ylmethyl)-2-(4-methanesulfonylbenzyl)-2,8-diaza-spiro[4.5]decan-1-one 8-(1-Cyclobutanecarbonyl-4-(SR)-phenylpyrrolidin-3-(RS)-ylmethyl)-2-(4-methanesulfonylbenzyl)-2,8-diaza-spiro[4.5]decan-1-one 8-(1-Cyclopentanecarbonyl-4-(SR)-phenylpyrrolidin-3-(RS)-ylmethyl)-2-(4-methanesulfonylbenzyl)-2,8-diaza-spiro[4.5]decan-1-one 8-(1-Cyclohexanecarbonyl-4-(SR)-phenylpyrrolidin-3-(RS)-ylmethyl)-2-(4-methanesulfonylbenzyl)-2,8-diaza-spiro[4.5]decan-1-one 8-(1-Cycloheptanecarbonyl-4-(SR)-phenylpyrrolidin-3-(RS)-ylmethyl)-2-(4-methanesulfonylbenzyl)-2,8-diaza-spiro[4.5]decan-1-one 8-[1-(2-Cyclopropyl-acetyl)-4-(SR)-phenylpyrrolidin-3-(RS)-ylmethyl]-2-(4-methanesulfonylbenzyl)-2,8-diaza-spiro[4.5]decan-1-one 8-[1-(2-Cyclopentyl-acetyl)-4-(SR)-phenylpyrrolidin-3-(RS)-ylmethyl]-2-(4-methanesulfonylbenzyl)-2,8-diaza-spiro[4.5]decan-1-one 8-[1-(2-Cyclohexyl-acetyl)-4-(SR)-phenylpyrrolidin-3-(RS)-ylmethyl]-2-(4-methanesulfonylbenzyl)-2,8-diaza-spiro[4.5]decan-1-one 8-(1-Isobutyryl-4-(SR)-phenylpyrrolidin-3-(RS)-ylmethyl)-2-(4-methanesulfonylbenzyl)-2,8-diaza-spiro[4.5]decan-1-one 2-(4-Methanesulfonylbenzyl)-8-[1-(3-methyl-butyryl)-4-(SR)-phenylpyrrolidin-3-(RS)-ylmethyl]-2,8-diaza-spiro[4.5]decan-1-one 8-[1-(2-Ethyl-butyryl)-4-(SR)-phenylpyrrolidin-3-(RS)-ylmethyl]-2-(4-methanesulfonylbenzyl)-2,8-diaza-spiro[4.5]decan-1-one 8-[1-(2-Chlorobenzoyl)-4-(SR)-phenylpyrrolidin-3-(RS)-ylmethyl]-2-(4-methanesulfonylbenzyl)-2,8-diaza-spiro[4.5]decan-1-one 8-[1-(2,6-Dichlorobenzoyl)-4-(SR)-phenylpyrrolidin-3-(RS)-ylmethyl]-2-(4-methanesulfonylbenzyl)-2,8-diaza-spiro[4.5]decan-1-one 2-(4-Methanesulfonylbenzyl)-8-[1-(2-methoxybenzoyl)-4-(SR)-phenylpyrrolidin-3-(RS)-ylmethyl]-2,8-diaza-spiro[4.5]decan-1-one 2-(4-Methanesulfonylbenzyl)-8-[4-(SR)-phenyl-1-(pyridine-2-carbonyl)-pyrrolidin-3-(RS)-ylmethyl]-2,8-diaza-spiro[4.5]decan-1-one 8-[1-(2-Fluorobenzoyl)-4-(SR)-phenylpyrrolidin-3-(RS)-ylmethyl]-2-(4-methanesulfonylbenzyl)-2,8-diaza-spiro[4.5]decan-1-one 2-(4-Methanesulfonylbenzyl)-8-[1-(2-methylbenzoyl)-4-(SR)-phenylpyrrolidin-3-(RS)-ylmethyl]-2,8-diaza-spiro[4.5]decan-1-one 2-(4-Methanesulfonylbenzyl)-8-[4-(SR)-phenyl-1-(pyridine-3-carbonyl)-pyrrolidin-3-(RS)-ylmethyl]-2,8-diaza-spiro[4.5]decan-1-one 2-(4-Methanesulfonylbenzyl)-8-[4-(SR)-phenyl-1-(pyridine-4-carbonyl)-pyrrolidin-3-(RS)-ylmethyl]-2,8-diaza-spiro[4.5]decan-1-one
8-[1-(Furan-2-carbonyl)-4-(SR)-phenylpyrrolidin-3-(RS)-ylmethyl]-2-(4-methanesulfonylbenzyl)-2,8-diaza-spiro[4.5]decan-1-one
2-(4-Methanesulfonylbenzyl)-8-[4-(SR)-phenyl-1-(thiophene-2-carbonyl)-pyrrolidin-3-(RS)-ylmethyl]-2,8-diaza-spiro[4.5]decan-1-one
8-(1-Benzenesulfonyl-4-(SR)-phenylpyrrolidin-3-((RS)-ylmethyl)-2-(4-bromobenzyl)-2,8-diaza-spiro[4.5]decan-1-one
3-((RS)-[2-(4-Bromobenzyl)-1-oxo-2,8-diaza-spiro[4.5]dec-8-ylmethyl]-4-(SR)-phenyl-pyrrolidine-1-carboxylic acid phenylamide
8-(1-Benzyl-4-(SR)-phenylpyrrolidin-3-((RS)-ylmethyl)-2-(4-bromobenzyl)-2,8-diaza-spiro[4.5]decan-1-one
2-(4-Bromobenzyl)-8-(1-cyclohexylmethyl-4-(SR)-phenylpyrrolidin-3-((RS)-ylmethyl)-2,8-diaza-spiro[4.5]decan-1-one
(3S,4S)-3-[2-(4-Bromo-benzyl)-1-oxo-2,8-diaza-spiro[4.5]dec-8-ylmethyl]-4-phenyl-pyrrolidine-1-carboxylic acid tert-butyl ester
2-(4-Bromo-benzyl)-8-((3R,4S)-4-phenyl-pyrrolidin-3-ylmethyl)-2,8-diaza-spiro[4.5]decan-1-one
8-((3S,4S)-1-Acetyl-4-phenyl-pyrrolidin-3-ylmethyl)-2-(4-bromo-benzyl)-2,8-diaza-spiro[4.5]decan-1-one
2-(4-Bromo-benzyl)-8-((3S,4S)-1-cyclopropanecarbonyl-4-phenyl-pyrrolidin-3-ylmethyl)-2,8-diaza-spiro[4.5]decan-1-one
2-(4-Bromo-benzyl)-8-[(3S,4S)-1-(2-cyclopropyl-acetyl)-4-phenyl-pyrrolidin-3-ylmethyl]-2,8-diaza-spiro[4.5]decan-1-one
2-(4-Bromo-benzyl)-8-[(3S,4S)-4-phenyl-1-(tetrahydropyran-4-carbonyl)-pyrrolidin-3-ylmethyl]-2,8-diaza-spiro[4.5]decan-1-one
2-(4-Bromo-benzyl)-8-[(3S,4S)-1-(2-chloro-benzoyl)-4-phenyl-pyrrolidin-3-ylmethyl]-2,8-diaza-spiro[4.5]decan-1-one
2-(4-Bromo-benzyl)-8-[(3S,4S)-1-(2-methoxy-benzoyl)-4-phenyl-pyrrolidin-3-ylmethyl]-2,8-diaza-spiro[4.5]decan-1-one
2-(4-Bromo-benzyl)-8-[(3S,4S)-4-phenyl-1-(pyridine-3-carbonyl)-pyrrolidin-3-ylmethyl]-2,8-diaza-spiro[4.5]decan-1-one
2-(4-Bromo-benzyl)-8-{(3S,4S)-1-[2-(3,4-dichloro-phenyl)-acetyl]-4-phenyl-pyrrolidin-3-ylmethyl}-2,8-diaza-spiro[4.5]decan-1-one
(3S,4S)-3-[2-(4-Methoxy-benzyl)-1-oxo-2,8-diaza-spiro[4.5]dec-8-ylmethyl]-4-phenyl-pyrrolidine-1-carboxylic acid tert-butyl ester
2-(4-Methoxy-benzyl)-8-((3R,4S)-4-phenyl-pyrrolidin-3-ylmethyl)-2,8-diaza-spiro[4.5]decan-1-one
8-((3S,4S)-1-Acetyl-4-phenyl-pyrrolidin-3-ylmethyl)-2-(4-methoxy-benzyl)-2,8-diaza-spiro[4.5]decan-1-one
2-(4-Methoxy-benzyl)-8-((3S,4S)-4-phenyl-1-propionyl-pyrrolidin-3-ylmethyl)-2,8-diaza-spiro[4.5]decan-1-one
8-[(3S,4S)-1-(2-Methoxy-acetyl)-4-phenyl-pyrrolidin-3-ylmethyl]-2-(4-methoxy-benzyl)-2,8-diaza-spiro[4.5]decan-1-one
8-((3S,4S)-1-Isobutyryl-4-phenyl-pyrrolidin-3-ylmethyl)-2-(4-methoxy-benzyl)-2,8-diaza-spiro[4.5]decan-1-one
8-((3S,4S)-1-Cyclopropanecarbonyl-4-phenyl-pyrrolidin-3-ylmethyl)-2-(4-methoxy-benzyl)-2,8-diaza-spiro[4.5]decan-1-one
8-[(3S,4S)-1-(2-Cyclopropyl-acetyl)-4-phenyl-pyrrolidin-3-ylmethyl]-2-(4-methoxy-benzyl)-2,8-diaza-spiro[4.5]decan-1-one
2-(4-Methoxy-benzyl)-8-[(3S,4S)-4-phenyl-1-(tetrahydro-pyran-4-carbonyl)-pyrrolidin-3-ylmethyl]-2,8-diaza-spiro[4.5]decan-1-one
8-[(3S,4S)-1-(4,4-Difluoro-cyclohexanecarbonyl)-4-phenyl-pyrrolidin-3-ylmethyl]-2-(4-methoxy-benzyl)-2,8-diaza-spiro[4.5]decan-1-one
8-[(3S,4S)-1-(2-Chloro-benzoyl)-4-phenyl-pyrrolidin-3-ylmethyl]-2-(4-methoxy-benzyl)-2,8-diaza-spiro[4.5]decan-1-one
8-[(3S,4S)-1-(2-Fluoro-benzoyl)-4-phenyl-pyrrolidin-3-ylmethyl]-2-(4-methoxy-benzyl)-2,8-diaza-spiro[4.5]decan-1-one
2-(4-Methoxy-benzyl)-8-[(3S,4S)-4-phenyl-1-(pyrimidine-5-carbonyl)-pyrrolidin-3-ylmethyl]-2,8-diaza-spiro[4.5]decan-1-one tri
8-[(3S,4S)-1-(4,6-Dimethyl-pyrimidine-5-carbonyl)-4-phenyl-pyrrolidin-3-ylmethyl]-2-(4-methoxy-benzyl)-2,8-diaza-spiro[4.5]decan-1-one tri
(3S,4S)-3-[2-(4-Methanesulfonyl-benzyl)-1-oxo-2,8-diaza-spiro[4.5]dec-8-ylmethyl]-4-phenyl-pyrrolidine-1-carboxylic acid tert-butyl ester
2-(4-Methanesulfonyl-benzyl)-8-((3R,4S)-4-phenyl-pyrrolidin-3-ylmethyl)-2,8-diaza-spiro[4.5]decan-1-one
8-((3S,4S)-1-Acetyl-4-phenyl-pyrrolidin-3-ylmethyl)-2-(4-methanesulfonyl-benzyl)-2,8-diaza-spiro[4.5]decan-1-one
2-(4-Methanesulfonyl-benzyl)-8-((3S,4S)-4-phenyl-1-propionyl-pyrrolidin-3-ylmethyl)-2,8-diaza-spiro[4.5]decan-1-one
8-((3S,4S)-1-Isobutyryl-4-phenyl-pyrrolidin-3-ylmethyl)-2-(4-methanesulfonyl-benzyl)-2,8-diaza-spiro[4.5]decan-1-one
8-((3S,4S)-1-Cyclopentanecarbonyl-4-phenyl-pyrrolidin-3-ylmethyl)-2-(4-methanesulfonyl-benzyl)-2,8-diaza-spiro[4.5]decan-1-one
8-((3S,4S)-1-Cyclopropanecarbonyl-4-phenyl-pyrrolidin-3-ylmethyl)-2-(4-methanesulfonyl-benzyl)-2,8-diaza-spiro[4.5]decan-1-one
8-[(3S,4S)-1-(2-Cyclopropyl-acetyl)-4-phenyl-pyrrolidin-3-ylmethyl]-2-(4-methanesulfonyl-benzyl)-2,8-diaza-spiro[4.5]decan-1-one
8-[(3S,4S)-1-(4,4-Difluoro-cyclohexanecarbonyl)-4-phenyl-pyrrolidin-3-ylmethyl]-2-(4-methanesulfonyl-benzyl)-2,8-diaza-spiro[4.5]decan-1-one
2-(4-Methanesulfonyl-benzyl)-8-[(3S,4S)-4-phenyl-1-(pyridine-3-carbonyl)-pyrrolidin-3-ylmethyl]-2,8-diaza-spiro[4.5] decan-1-one
2-(4-Methanesulfonyl-benzyl)-8-[(3S,4S)-4-phenyl-1-(pyrimidine-5-carbonyl)-pyrrolidin-3-ylmethyl]-2,8-diaza-spiro[4.5]decan-1-one tri
8-[(3S,4S)-1-(4,6-Dimethyl-pyrimidine-5-carbonyl)-4-phenyl-pyrrolidin-3-ylmethyl]-2-(4-methanesulfonyl-benzyl)-2,8-diaza-spiro[4.5]decan-1-one tri
8-[(3S,4S)-1-(2-Chloro-benzoyl)-4-phenyl-pyrrolidin-3-ylmethyl]-2-(4-methanesulfonyl-benzyl)-2,8-diaza-spiro[4.5]decan-1-one
8-[(3S,4S)-1-(2-Fluoro-benzoyl)-4-phenyl-pyrrolidin-3-ylmethyl]-2-(4-methanesulfonyl-benzyl)-2,8-diaza-spiro[4.5] decan-1-one
(3S,4S)-3-[2-(4-Methoxy-benzyl)-3-oxo-2,8-diaza-spiro[4.5]dec-8-ylmethyl]-4-phenyl-pyrrolidine-1-carboxylic acid tert-butyl ester
2-(4-Methoxy-benzyl)-8-((3R,4S)-4-phenyl-pyrrolidin-3-ylmethyl)-2,8-diaza-spiro[4.5]decan-3-one 8-((3S,4S)-1-Isobutyryl-4-phenyl-pyrrolidin-3-ylmethyl)-2-(4-methoxy-benzyl)-2,8-diaza-spiro[4.5]decan-3-one 8-((3S,4S)-1-Cyclopropanecarbonyl-4-phenyl-pyrrolidin-3-ylmethyl)-2-(4-methoxy-benzyl)-2,8-diaza-spiro[4.5]decan-3-one 8-[(3S,4S)-1-(2-Cyclopropyl-acetyl)-4-phenyl-pyrrolidin-3-ylmethyl]-2-(4-methoxy-benzyl)-2,8-diaza-spiro[4.5]decan-3-one (3S,4S)-3-[2-(4-Methanesulfonyl-benzyl)-3-oxo-2,8-diaza-spiro[4.5]dec-8-ylmethyl]-4-phenyl-pyrrolidine-1-carboxylic acid tert-butyl ester 2-(4-Methanesulfonyl-benzyl)-8-((3R,4S)-4-phenyl-pyrrolidin-3-ylmethyl)-2,8-diaza-spiro[4.5]decan-3-one 8-((3S,4S)-1-Isobutyryl-4-phenyl-pyrrolidin-3-ylmethyl)-2-(4-methanesulfonyl-benzyl)-2,8-diaza-spiro[4.5]decan-3-one 8-((3S,4S)-1-Cyclopropanecarbonyl-4-phenyl-pyrrolidin-3-ylmethyl)-2-(4-methanesulfonyl-benzyl)-2,8-diaza-spiro[4.5]decan-3-one 8-[(3S,4S)-1-(2-Cyclopropyl-acetyl)-4-phenyl-pyrrolidin-3-ylmethyl]-2-(4-methanesulfonyl-benzyl)-2,8-diaza-spiro[4.5]decan-3-one 2-(4-Bromo-benzyl)-8-((3S,4S)-4-phenyl-1-propionyl-pyrrolidin-3-ylmethyl)-2,8-diaza-spiro[4.5]decan-1-one 2-(4-Methanesulfonyl-benzyl)-8-[(3S,4S)-4-phenyl-1-(tetrahydro-pyran-4-carbonyl)-pyrrolidin-3-ylmethyl]-2,8-diaza-spiro[4.5]decan-1-one 8-((3S,4S)-1-Ethanesulfonyl-4-phenyl-pyrrolidin-3-ylmethyl)-2-(4-methoxy-benzyl)-2,8-diaza-spiro[4.5]decan-1-one 2-(4-Methoxy-benzyl)-8-[(3S,4S)-4-phenyl-1-(propane-2-sulfonyl)-pyrrolidin-3-ylmethyl]-2,8-diaza-spiro[4.5]decan-1-one 8-((3S,4S)-1-Cyclopropanesulfonyl-4-phenyl-pyrrolidin-3-ylmethyl)-2-(4-methoxy-benzyl)-2,8-diaza-spiro[4.5]decan-1-one 8-((3S,4S)-1-Ethanesulfonyl-4-phenyl-pyrrolidin-3-ylmethyl)-2-(4-methanesulfonyl-benzyl)-2,8-diaza-spiro[4.5]decan-1-one 2-(4-Methanesulfonyl-benzyl)-8-[(3S,4S)-4-phenyl-1-(propane-2-sulfonyl)-pyrrolidin-3-ylmethyl]-2,8-diaza-spiro[4.5]decan-1-one 8-((3S,4S)-1-Cyclopropanesulfonyl-4-phenyl-pyrrolidin-3-ylmethyl)-2-(4-methanesulfonyl-benzyl)-2,8-diaza-spiro[4.5]decan-1-one 8-((3S,4S)-1-Cyclopentanesulfonyl-4-phenyl-pyrrolidin-3-ylmethyl)-2-(4-methanesulfonyl-benzyl)-2,8-diaza-spiro[4.5]decan-1-one 2-(4-Methoxy-benzyl)-8-[(3S,4S)-1-(morpholine-4-carbonyl)-4-phenyl-pyrrolidin-3-ylmethyl]-2,8-diaza-spiro[4.5]decan-1-one (3S,4S)-3-[2-(4-Methoxy-benzyl)-1-oxo-2,8-diaza-spiro[4.5]dec-8-ylmethyl]-4-phenyl-pyrrolidine-1-carboxylic acid dimethylamide 2-(4-Methoxy-benzyl)-8-[(3S,4S)-4-phenyl-1-(pyrrolidine-1-carbonyl)-pyrrolidin-3-ylmethyl]-2,8-diaza-spiro[4.5]decan-1-one 8-[(3S,4S)-1-(3,3-Difluoro-pyrrolidine-1-carbonyl)-4-phenyl-pyrrolidin-3-ylmethyl]-2-(4-methoxy-benzyl)-2,8-diaza-spiro[4.5]decan-1-one (3S,4S)-3-[2-(4-Methoxy-benzyl)-1-oxo-2,8-diaza-spiro[4.5]dec-8-ylmethyl]-4-phenyl-pyrrolidine-1-carboxylic acid cyclopropylamide (3S,4S)-3-[2-(4-Methoxy-benzyl)-1-oxo-2,8-diaza-spiro[4.5]dec-8-ylmethyl]-4-phenyl-pyrrolidine-1-carboxylic acid cyclopentylamide 2-(4-Methanesulfonyl-benzyl)-8-[(3S,4S)-1-(morpholine-4-carbonyl)-4-phenyl-pyrrolidin-3-ylmethyl]-2,8-diaza-spiro[4.5]decan-1-one (3S,4S)-3-[2-(4-Methanesulfonyl-benzyl)-1-oxo-2,8-diaza-spiro[4.5]dec-8-ylmethyl]-4-phenyl-pyrrolidine-1-carboxylic acid dimethylamide 2-(4-Methanesulfonyl-benzyl)-8-[(3S,4S)-4-phenyl-1-(pyrrolidine-1-carbonyl)-pyrrolidin-3-ylmethyl]-2,8-diaza-spiro[4.5]decan-1-one 8-[(3S,4S)-1-(3,3-Difluoro-pyrrolidine-1-carbonyl)-4-phenyl-pyrrolidin-3-ylmethyl]-2-(4-methanesulfonyl-benzyl)-2,8-diaza-spiro[4.5]decan-1-one (3S,4S)-3-[2-(4-Methanesulfonyl-benzyl)-1-oxo-2,8-diaza-spiro[4.5]dec-8-ylmethyl]-4-phenyl-pyrrolidine-1-carboxylic acid cyclopropylamide (3S,4S)-3-[2-(4-Methanesulfonyl-benzyl)-1-oxo-2,8-diaza-spiro[4.5]dec-8-ylmethyl]-4-phenyl-pyrrolidine-1-carboxylic acid cyclopentylamide 2-(4-Methoxy-benzyl)-8-((3R,4S)-1-methyl-4-phenyl-pyrrolidin-3-ylmethyl)-2,8-diaza-spiro[4.5]decan-1-one 8-((3S,4S)-1-Isopropyl-4-phenyl-pyrrolidin-3-ylmethyl)-2-(4-methoxy-benzyl)-2,8-diaza-spiro[4.5]decan-1-one 8-((3S,4S)-1-Isobutyl-4-phenyl-pyrrolidin-3-ylmethyl)-2-(4-methoxy-benzyl)-2,8-diaza-spiro[4.5]decan-1-one 8-((3S,4S)-1-Cyclopropylmethyl-4-phenyl-pyrrolidin-3-ylmethyl)-2-(4-methoxy-benzyl)-2,8-diaza-spiro[4.5]decan-1-one 2-(4-Methoxy-benzyl)-8-[(3S,4S)-4-phenyl-1-(tetrahydro-pyran-4-ylmethyl)-pyrrolidin-3-ylmethyl]-2,8-diaza-spiro[4.5]decan-1-one 8-[(3S,4S)-1-(4,4-Difluoro-cyclohexylmethyl)-4-phenyl-pyrrolidin-3-ylmethyl]-2-(4-methoxy-benzyl)-2,8-diaza-spiro[4.5]decan-1-one 2-(4-Methanesulfonyl-benzyl)-8-((3R,4S)-1-methyl-4-phenyl-pyrrolidin-3-ylmethyl)-2,8-diaza-spiro[4.5]decan-1-one 8-((3S,4S)-1-Isopropyl-4-phenyl-pyrrolidin-3-ylmethyl)-2-(4-methanesulfonyl-benzyl)-2,8-diaza-spiro[4.5]decan-1-one 8-((3S,4S)-1-Isobutyl-4-phenyl-pyrrolidin-3-ylmethyl)-2-(4-methanesulfonyl-benzyl)-2,8-diaza-spiro[4.5]decan-1-one 8-((3S,4S)-1-Cyclopropylmethyl-4-phenyl-pyrrolidin-3-ylmethyl)-2-(4-methanesulfonyl-benzyl)-2,8-diaza-spiro[4.5]decan-1-one 2-(4-Methanesulfonyl-benzyl)-8-[(3S,4S)-4-phenyl-1-(tetrahydro-pyran-4-ylmethyl)-pyrrolidin-3-ylmethyl]-2,8-diaza-spiro[4.5]decan-1-one 8-[(3S,4S)-1-(4,4-Difluoro-cyclohexylmethyl)-4-phenyl-pyrrolidin-3-ylmethyl]-2-(4-methanesulfonyl-benzyl)-2,8-diaza-spiro[4.5]decan-1-one (3S,4S)-3-[2-(4-Methoxy-benzyl)-1-oxo-2,8-diaza-spiro[4.5]dec-8-ylmethyl]-4-phenyl-pyrrolidine-1-carboxylic acid methyl ester (3S,4S)-3-[2-(4-Methoxy-benzyl)-1-oxo-2,8-diaza-spiro[4.5]dec-8-ylmethyl]-4-phenyl-pyrrolidine-1-carboxylic acid ethyl ester (3S,4S)-3-[2-(4-Methoxy-benzyl)-1-oxo-2,8-diaza-spiro[4.5]dec-8-ylmethyl]-4-phenyl-pyrrolidine-1-carboxylic acid isopropyl ester (3S,4S)-3-[2-(4-Methoxy-benzyl)-1-oxo-2,8-diaza-spiro[4.5]dec-8-ylmethyl]-4-phenyl-pyrrolidine-1-carboxylic acid cyclopentyl ester (3S,4S)-3-[2-(4-Methoxy-benzyl)-1-oxo-2,8-diaza-spiro[4.5]dec-8-ylmethyl]-4-phenyl-pyrrolidine-1-carboxylic acid cyclohexyl ester (3S,4S)-3-[2-(4-Methanesulfonyl-benzyl)-1-oxo-2,8-diaza-spiro[4.5]dec-8-ylmethyl]-4-phenyl-pyrrolidine-1-carboxylic acid methyl ester (3S,4S)-3-[2-(4-Methanesulfonyl-benzyl)-1-oxo-2,8-diaza-spiro[4.5]dec-8-ylmethyl]-4-phenyl-pyrrolidine-1-carboxylic acid ethyl ester (3S,4S)-3-[2-(4-Methanesulfonyl-benzyl)-1-oxo-2,8-diaza-spiro[4.5]dec-8-ylmethyl]-4-phenyl-pyrrolidine-1-carboxylic acid isopropyl ester (3S,4S)-3-[2-(4-Methanesulfonyl-benzyl)-1-oxo-2,8-diaza-spiro[4.5]dec-8-ylmethyl]-4-phenyl-pyrrolidine-1-carboxylic acid cyclopentyl ester (3S,4S)-3-[2-(4-Methanesulfonyl-benzyl)-1-oxo-2,8-diaza-spiro[4.5]dec-8-ylmethyl]-4-phenyl-pyrrolidine-1-carboxylic acid cyclohexyl ester 8-[(3S,4S)-1-(2-Cyclopropyl-acetyl)-4-phenyl-pyrrolidin-3-ylmethyl]-2-(4-fluoro-benzyl)-2,8-diaza-spiro[4.5]decan-1-one 2-(4-Chloro-benzyl)-8-[(3S,4S)-1-(2-cyclopropyl-acetyl)-4-phenyl-pyrrolidin-3-ylmethyl]-2,8-diaza-spiro[4.5]decan-1-one 4-{8-[(3S,4S)-1-(2-Cyclopropyl-acetyl)-4-phenyl-pyrrolidin-3-ylmethyl]-1-oxo-2,8-diaza-spiro[4.5]dec-2-ylmethyl}-benzonitrile 8-[(3S,4S)-1-(2-Cyclopropyl-acetyl)-4-phenyl-pyrrolidin-3-ylmethyl]-2-(4-difluoromethoxy-benzyl)-2,8-diaza-spiro[4.5]decan-1-one 8-[(3S,4S)-1-(2-Cyclopropyl-acetyl)-4-phenyl-pyrrolidin-3-ylmethyl]-2-(4-trifluoromethoxy-benzyl)-2,8-diaza-spiro[4.5]decan-1-one 8-[(3S,4S)-1-(2-Cyclopropyl-acetyl)-4-phenyl-pyrrolidin-3-ylmethyl]-2-(4-trifluoromethyl-benzyl)-2,8-diaza-spiro[4.5]decan-1-one 8-[(3S,4S)-1-(2-Cyclopropyl-acetyl)-4-phenyl-pyrrolidin-3-ylmethyl]-2-(4-pyrazol-1-yl-benzyl)-2,8-diaza-spiro[4.5]decan-1-one 2-(4-Fluoro-benzyl)-8-((3S,4S)-4-phenyl-1-propionyl-pyrrolidin-3-ylmethyl)-2,8-diaza-spiro[4.5]decan-1-one 2-(4-Chloro-benzyl)-8-((3S,4S)-4-phenyl-1-propionyl-pyrrolidin-3-ylmethyl)-2,8-diaza-spiro[4.5]decan-1-one 4-[1-Oxo-8-((3S,4S)-4-phenyl-1-propionyl-pyrrolidin-3-ylmethyl)-2,8-diaza-spiro[4.5]dec-2-ylmethyl]-benzonitrile 2-(4-Difluoromethoxy-benzyl)-8-((3S,4S)-4-phenyl-1-propionyl-pyrrolidin-3-ylmethyl)-2,8-diaza-spiro[4.5]decan-1-one 8-((3S,4S)-4-Phenyl-1-propionyl-pyrrolidin-3-ylmethyl)-2-(4-trifluoromethoxy-benzyl)-2,8-diaza-spiro[4.5]decan-1-one 8-((3S,4S)-4-Phenyl-1-propionyl-pyrrolidin-3-ylmethyl)-2-(4-trifluoromethyl-benzyl)-2,8-diaza-spiro[4.5]decan-1-one 8-((3S,4S)-4-Phenyl-1-propionyl-pyrrolidin-3-ylmethyl)-2-(4-pyrazol-1-yl-benzyl)-2,8-diaza-spiro[4.5]decan-1-one and pharmaceutically acceptable salts thereof.

21. A compound according to claim 20, wherein said compound is in the form of pharmaceutically acceptable salt.

22. A compound according to claim 21, wherein said compound is in the form of a hydrochloride salt.

23. A compound according to claim 1, wherein said compound is in the form of the (3R,4R)-diastereomer.

24. A compound according to claim 1, wherein said compound is in the form of the (3S,4R)-diastereomer.

25. A compound according to claim 1, wherein said compound is in the form of the (3R,4S)-diastereomer.

26. A compound according to claim 1, wherein said compound is in the form of the (3S,4S)-diastereomer.

27. A compound according to claim 1, wherein said compound is in the form of the (+) diastereoisomer having a diastereoisomeric excess of 99%.

28. A compound according to claim 1, wherein said compound is in the form of the (+) diastereoisomer having a diastereoisomeric excess of 95%.

29. A compound according to claim 1, wherein said compound is in the form of the (+) diastereoisomer having a diastereoisomeric excess of 90%.

30. A compound according to claim 1, wherein said compound is in the form of the (−) diastereoisomer having a diastereoisomeric excess of 99%.

31. A compound according to claim 1, wherein said compound is in the form of the (−) diastereoisomer having a diastereoisomeric excess of 95%.

32. A compound according to claim 1, wherein said compound is in the form of the (−) diastereoisomer having a diastereoisomeric excess of 90%.

33. A compound according to claim 1, wherein said compound is in the form of the (−) diastereoisomer having a diastereoisomeric excess of the form where C-3 and C-4 substituents are in the trans configuration as shown in the following formulas:

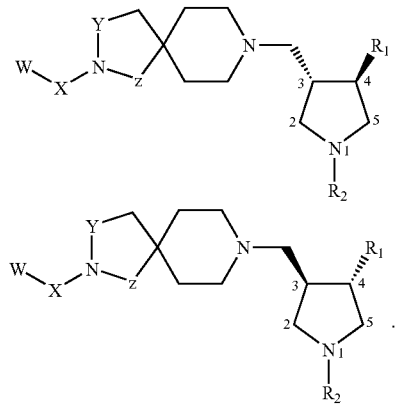

34. A compound according to claim 1, wherein said compound is in the form of the (+) diastereoisomer having a diastereoisomeric excess of the form where C-3 and C-4 substituents are in the trans configuration as shown in the following formulas:

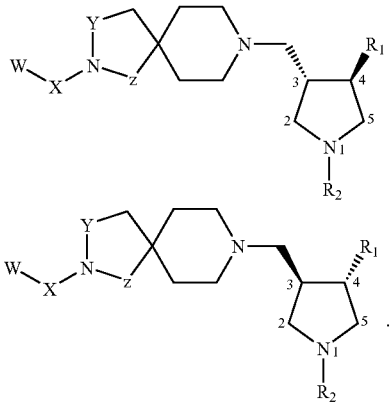

35. A pharmaceutical composition comprising a therapeutically effective amount of at least one compound according to claim 1 and at least one pharmaceutically acceptable carrier or excipient.

36. A pharmaceutical composition comprising a therapeutically effective amount of at least one compound according to claim 20 and at least one pharmaceutically acceptable carrier or excipient.

37. A compound according to claim 1, wherein said optionally substituted $C_{1-10}$ alkyl groups, optionally substituted $C_{2-10}$ alkenyl groups, and optionally substituted $C_{2-10}$ alkynyl groups are, in each case, unsubstituted or substituted by one or more substituents selected from halogen, cyano, nitro, oxo, amino, COOH, COO—$C_{1-4}$ alkyl, CO—$C_{1-4}$ alkyl, and phenyl;

wherein said optionally substituted $C_{6-12}$ aryl groups are, in each case, unsubstituted or substituted by one or more substituents selected from halogen, cyano, nitro, oxo, amino, $C_{1-4}$ alkyl, $C_{1-4}$ alkoxy, halogenated $C_{1-4}$ alkyl, halogenated $C_{1-4}$ alkoxy, COOH, COO—$C_{1-4}$ alkyl, CO—$C_{1-4}$ alkyl, $C_{1-4}$ alkyl-S—, halogenated $C_{1-4}$ alkyl-S—, benzyloxy, and pyrazolyl;

wherein said optionally substituted $C_{6-12}$ aralkyl groups are, in each case, unsubstituted or substituted one or more substituents selected from halogen, cyano, nitro, oxo, amino, $C_{1-4}$ alkyl, $C_{1-4}$ alkoxy, halogenated $C_{1-4}$ alkyl, halogenated $C_{1-4}$ alkoxy, COOH, COO—$C_{1-4}$ alkyl, CO—$C_{1-4}$ alkyl, $C_{1-4}$ alkyl-S—, halogenated $C_{1-4}$ alkyl-S—, benzyloxy, and pyrazolyl; and wherein said optionally substituted 3 to 10 membered heterocycle groups and said optionally substituted 3 to 10 membered heteroaralkyl groups are, in each case, unsubstituted or substituted one or more substituents selected from halogen, cyano, nitro, oxo, amino, $C_{1-4}$ alkyl, $C_{1-4}$ alkoxy, halogenated $C_{1-4}$ alkyl, halogenated $C_{1-4}$ alkoxy, COOH, COO—$C_{1-4}$ alkyl, CO—$C_{1-4}$ alkyl, $C_{1-4}$ alkyl-S—, halogenated $C_{1-4}$ alkyl-S—, benzyloxy, and pyrazolyl.

38. A compound according to claim 1, wherein:

said optionally substituted $C_{1-10}$ alkyl groups are, in each case, selected from methyl, ethyl, propyl, isopropyl, butyl, isobutyl, sec-butyl, tert-butyl, pentyl, isopentyl, neopentyl, tert-pentyl, hexyl, isohexyl, neohexyl and cyclohexyl, which in each case are unsubstituted or optionally substituted one or more times by halogen, cyano, nitro, oxo, amino, COOH, COO—$C_{1-4}$ alkyl, CO—$C_{1-4}$ alkyl, and/or phenyl;

said optionally substituted $C_{2-10}$ alkenyl groups are, in each case, selected from allyl, vinyl, acetylenyl, ethylenyl, propenyl, isopropenyl butenyl, isobutenyl, hexenyl, butadienyl, pentenyl, pentadienyl, hexenyl, hexadienyl, hexatrienyl, heptenyl, heptadienyl, heptatrienyl, octenyl, octadienyl, octatrienyl, and octatetraenyl, which in each case are unsubstituted or optionally substituted one or more times by, for example, halogen, cyano, nitro, oxo, amino, COOH, COO—$C_{1-4}$ alkyl, CO—$C_{1-4}$ alkyl, and/or phenyl;

said optionally substituted $C_{2-10}$ alkynyl groups are, in each case, selected from propynyl, butynyl, pentynyl, hexynyl, cyclohexenyl and cyclohexdienyl, which in each case are unsubstituted or optionally substituted one or more times by, for example, halogen, cyano, nitro, oxo, amino, COOH, COO—$C_{1-4}$ alkyl, CO—$C_{1-4}$ alkyl, and/or phenyl;

said optionally substituted $C_{6-12}$ aryl groups are, in each case, selected from phenyl, tolyl, dimethylphenyl, aminophenyl, anilinyl, naphthyl, anthryl, phenanthryl or biphenyl, which in each case is unsubstituted or substituted one or more times by halogen, cyano, nitro, oxo, amino, $C_{1-4}$ alkyl, $C_{1-4}$ alkoxy, halogenated $C_{1-4}$ alkyl, halogenated $C_{1-4}$ alkoxy, COOH, COO—$C_{1-4}$ alkyl, CO—$C_{1-4}$ alkyl, $C_{1-4}$ alkyl-S—, halogenated $C_{1-4}$ alkyl-S—, benzyloxy, and/or pyrazolyl;

said optionally substituted $C_{6-12}$ aralkyl groups are, in each case, selected from benzyl, benzhydryl, trityl, phenethyl, 3-phenylpropyl, 2-phenylpropyl, 4-phenylbutyl and naphthylmethyl, which in each case is unsubstituted or substituted one or more times by halogen, cyano, nitro, oxo, amino, $C_{1-4}$ alkyl, $C_{1-4}$ alkoxy, halogenated $C_{1-4}$ alkyl, halogenated $C_4$ alkoxy, COOH, COO—$C_{1-4}$ alkyl, CO—$C_{1-4}$ alkyl, $C_{1-4}$ alkyl-S—, halogenated $C_{1-4}$ alkyl-S—, benzyloxy, and/or pyrazolyl; and said optionally substituted 3 to 10 membered heterocycle groups are, in each case, selected from azepinyl, aziridinyl, azetyl, azetidinyl, diazepinyl, dithiadiazinyl, dioxazepinyl, dioxolanyl, dithiazolyl, furanyl, isooxazolyl, isothiazolyl, imidazolyl, morpholinyl, morpholino, oxetanyl, oxadiazolyl, oxiranyl, oxazinyl, oxazolyl, piperazinyl, pyrazinyl, pyridazinyl, pyrimidinyl, piperidyl, piperidino, pyridyl, pyranyl, pyrazolyl, pyrrolyl, pyrrolidinyl, thiatriazolyl, tetrazolyl, thiadiazolyl, triazolyl, thiazolyl, thienyl, tetrazinyl, thiadiazinyl, triazinyl, thiazinyl, thiopyranyl furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl and pyridopyrimidinyl, which in each case is unsubstituted or substituted one or more times by halogen, cyano, nitro, oxo, amino, $C_{1-4}$ alkyl, $C_{1-4}$ alkoxy, halogenated $C_{1-4}$ alkyl, halogenated $C_{1-4}$ alkoxy, COOH, COO—$C_{1-4}$ alkyl, CO—$C_{1-4}$ alkyl, $C_{1-4}$ alkyl-S—, halogenated $C_{1-4}$ alkyl-S—, benzyloxy, and/or pyrazolyl.

39. A compound according to claim 1, wherein said compound is in the form of pharmaceutically acceptable salt.

40. A compound according to claim 39, wherein said compound is in the form of a hydrochloride salt.

* * * * *

UNITED STATES PATENT AND TRADEMARK OFFICE
CERTIFICATE OF CORRECTION

PATENT NO. : 7,288,548 B2  Page 1 of 1
APPLICATION NO. : 10/937880
DATED : October 30, 2007
INVENTOR(S) : Chan Chun Kong et al.

It is certified that error appears in the above-identified patent and that said Letters Patent is hereby corrected as shown below:

Column 151, line 50, reads "is chosen from H" should read -- is H --
Column 152, line 13, reads "independently chosen from H," should read
-- independently H, --
Column 152, line 15, reads "is chosen from H," should read -- is H, --
Column 154, line 27, reads "and tert-butyl." should read -- or tert-butyl. --
Column 154, line 38, reads "and phenyl." should read -- or phenyl. --
Column 154, line 52, reads "are H." should read -- is H. --
Column 164, line 7, reads "of pharmaceutically" should read -- of a pharmaceutically --
Column 165, line 54, begin new line after "pyazolyl; and"
Column 165, line 58, reads "thiopyranyl furoisoxazolyl" should read -- thiopyranyl, furoisoxazolyl --
Column 166, line 43, reads "halogenated $C_4$ alkoxy," should read -- halogenated $C_{1-4}$ alkoxy --

Signed and Sealed this

Sixth Day of January, 2009

JON W. DUDAS
*Director of the United States Patent and Trademark Office*